United States Patent
Calzone

(10) Patent No.: US 11,319,376 B2
(45) Date of Patent: May 3, 2022

(54) COMBINATION OF GLUCAGON RECEPTOR ANTAGONISTS AND PI3K PATHWAY INHIBITORS FOR THE TREATMENT OF CANCER

(71) Applicant: REMD Biotherapeutics, Inc., Camarillo, CA (US)

(72) Inventor: Frank J Calzone, Westlake Village, CA (US)

(73) Assignee: REMD Biotherapeutics, Inc., Camarillo, CA (US)

(*) Notice: Subject to any disclaimer, the term of this patent is extended or adjusted under 35 U.S.C. 154(b) by 277 days.

(21) Appl. No.: 16/322,964

(22) PCT Filed: Aug. 3, 2017

(86) PCT No.: PCT/US2017/045390
§ 371 (c)(1),
(2) Date: Feb. 3, 2019

(87) PCT Pub. No.: WO2018/027084
PCT Pub. Date: Feb. 8, 2018

(65) Prior Publication Data
US 2019/0169300 A1 Jun. 6, 2019

Related U.S. Application Data

(60) Provisional application No. 62/370,642, filed on Aug. 3, 2016.

(51) Int. Cl.
| | |
|---|---|
| *A61P 35/00* | (2006.01) |
| *A61K 31/4375* | (2006.01) |
| *A61K 31/4439* | (2006.01) |
| *A61K 31/4545* | (2006.01) |
| *A61K 31/517* | (2006.01) |
| *A61K 31/519* | (2006.01) |
| *A61K 31/5377* | (2006.01) |
| *C07K 16/28* | (2006.01) |
| *A61K 39/395* | (2006.01) |
| *A61K 39/00* | (2006.01) |

(52) U.S. Cl.
CPC ...... *C07K 16/2869* (2013.01); *A61K 31/4375* (2013.01); *A61K 31/4439* (2013.01); *A61K 31/4545* (2013.01); *A61K 31/517* (2013.01); *A61K 31/519* (2013.01); *A61K 31/5377* (2013.01); *A61K 39/3955* (2013.01); *A61P 35/00* (2018.01); *A61K 2039/505* (2013.01); *A61K 2039/541* (2013.01); *A61K 2039/545* (2013.01); *C07K 2317/21* (2013.01); *C07K 2317/73* (2013.01); *C07K 2317/76* (2013.01); *C07K 2317/92* (2013.01)

(58) Field of Classification Search
CPC . C07K 16/2869; A61P 35/00; A61K 31/4375; A61K 31/4439; A61K 31/4545; A61K 31/517; A61K 31/519; A61K 31/5377; A61K 39/3955
USPC ....................................................... 424/135.1
See application file for complete search history.

(56) References Cited

U.S. PATENT DOCUMENTS

| | | |
|---|---|---|
| 2011/0223160 A1 | 9/2011 | Yan et al. |
| 2012/0059005 A1 | 3/2012 | Baselga et al. |

FOREIGN PATENT DOCUMENTS

| | | |
|---|---|---|
| WO | 2008036341 | 3/2008 |
| WO | 2015189698 | 12/2015 |

OTHER PUBLICATIONS

Fritsch et al., "Characterization of the Novel and Specific PI3K Inhibitor NVP-BYL719 and Development of the Patient Stratification Strategy for Clinical Trials", Molecular Cancer Therapeutics, 13(5): 1117-1129, Mar. 7, 2014.
Geuna et al., "Complications of hyperglycaemia with PI3K-AKT-mTOR inhibitors in patients with advanced solid tumours on Phase I clinical trials", British Journal of Cancer, 113(11): 1541-1547, Nov. 10, 2015.
Okamoto et al., "Glucagon receptor inhibition normalizes blood glucose in severe insulin-resistant mice", PNAS USA, 114(10): 2753-2758, Jan. 23, 2017.
PCT Written Opinion of the International Search Authority, Jan. 26, 2018.
Smith et al., "Effects of acutely inhibiting PI3K isoforms and mTOR on regulation of glucose metabolism in vivo", Biochemical Journal, 442(1): 161-169, Jan. 27, 2012.
Ward et al., "Metabolic Reprogramming: A Cancer Hallmark Even Warburg Did Not Anticipate", Cancer Cell, 21(3): 297-308, Mar. 20, 2012.

*Primary Examiner* — Yan Xiao
(74) *Attorney, Agent, or Firm* — Craig A Crandall, APC; Craig A Crandall

(57) ABSTRACT

The present disclosure relates to combination therapy methods of treating a subject having cancer, comprising administering to the subject a) an effective amount of a pharmaceutical composition comprising a phosphatidylinositol 3-kinase (PI3K) pathway inhibitor, or a pharmaceutically acceptable salt thereof, and b) an effective amount of a pharmaceutical composition comprising a glucagon receptor antagonist.

13 Claims, 4 Drawing Sheets
Specification includes a Sequence Listing.

COMBINATION OF GLUCAGON RECEPTOR ANTAGONISTS AND PI3K PATHWAY INHIBITORS FOR THE TREATMENT OF CANCER

RELATED PATENT APPLICATIONS

This application is a U.S. National Stage Application pursuant to 35 U.S.C. § 371 of PCT/US2017/045390, filed Aug. 3, 2017, which claims benefit of U.S. Provisional Application No. 62/370,642, filed Aug. 3, 2016, each incorporated by reference in their entirety.

TECHNICAL FIELD

Phosphatidylinositol 3-kinases (PI3Ks) are lipid kinases that play central role in regulation of cellular metabolism, cell cycle, apoptosis, DNA repair, senescence, angiogenesis, and motility (Cantley L C, Science, 296 (5573): 1655-1657, 2002). PI3K signaling regulates a wide range of cellular processes including protein synthesis, cell survival, proliferation, differentiation, senescence, motility, angiogenesis and metabolism. Upon generation of second messengers (PIP3, PI 3,4-bisphosphate), the PI3K signaling impinges on a diverse array of pleckstrin homology (PH) domain-containing intracellular signaling proteins, and indirectly triggers a cascade of events that culminates in activation of multiple effector kinase pathways, including the AKT, mTOR, ERK1/2, p38 MAPK, NFκB, and JNK/SAPK pathways and ultimately result in survival and growth of normal cells (Id). Although the activity of PI3Ks is tightly regulated in normal cells by internal signals such as PTEN (phosphatase and tensin homolog deleted from chromosome 10), it has been recognized that deregulation of the PI3K signaling pathway is associated with development in one-third of human cancers (Arteaga C L, Curr Top Microbiol Immunol., 347:189-208, 2010; Liu P, Nat Rev Drug Discov., 8(8):627-644, 2009). Genetic aberrations that drive the PI3K pathway in cancer include gene amplification of PI3Ks, loss of the regulatory activity of PTEN, and activating mutations of receptor tyrosine kinases (RTKs) such as EGFR and HER2 (Engelman J A, Nat Rev Cancer., 9(8):550-562, 2009).

Two PI3K isoforms (PIK3α and PI3Kβ) are essential to mediating the actions of insulin that control overall body metabolism including glucose homeostasis and lipogenesis (Wei et al., Vaccine 33, 7401-7407, 2015). In the liver, activation of the insulin receptor (IR) by insulin stimulates the utilization and storage of glucose as glycogen and lipid while repressing gluconeogenesis. Insulin signaling also regulates glucose uptake and utilization in peripheral tissues such muscle and adipose tissue. Defective insulin signaling has been linked to type 1 diabetes (T1 D), type 2 diabetes (T2D) and other metabolic syndromes (Moller and Kaufman, Annual review of medicine 56, 45-62, 2005). In addition to insulin, peripheral cell metabolism is controlled by the actions of and insulin-like growth factors (IGF1, IGF2) through binding to the insulin-like growth factor receptor 1 (LeRoith and Yakar, Nat Clin Pract End Met 3, 302-310, 2007).

In peripheral tissues, the PI3Ks pathway inhibitors (PI3Ki) have emerged as viable targets for novel anti-cancer therapy. Successful drug design has yielded three classes of potent and selective small molecule inhibitors that have progressed from advanced preclinical testing to different stages of clinical development. In the last few years, several classes of potent and selective small molecule PI3K pathway inhibitors have been developed, and at least fifteen compounds have progressed into clinical trials as new anticancer drugs (Akinleye et al. Journal of Hematology & Oncology, 6:88, 2013). Unfortunately, the clinical benefits have been disappointing to date due to low target coverage, and many PI3K pathway inhibitors demonstrate considerable toxicities in animal studies and have not advanced to clinical evaluation because of this pharmaceutical limitation.

Hyperglycemia, hyperinsulinemia, insulin resistance and body weight loss are a dose limiting toxicity observed in subjects treated with PI3Ki's (Smith, G. C., et al., Biochem J, 442(1):161-9, 2012). For example, 1) hyperglycemia overrides the metabolic action of PI3Ki in tumors by increasing glucose utilization and aerobic glycolysis, thus promoting tumor glucose uptake which drives cell growth and replication irrespective of PI3K inhibition (Ward et al., Cancer Cell. 21(3):297-308, 2012), 2) hyperinsulinemia antagonizes PI3Ki by stimulating tumor IR and IGF1R hybrid receptor signaling; and 3) the T1 D-like symptoms induced by PI3Ki are dose limiting and severely limit tumor target coverage (Fritsch, C., et al., Mol Cancer Ther, 2014. 13(5):1117-29, 2014). The toxicology observed with PI3K inhibitors is not normalized by drugs used to manage diabetes (e.g., treatment of CD-17 scid mice with GSK690693 potently induces hyperglycemia. This effect was not prevented or reduce by several drug used to treat clinical diabetes including rosiglitazone maleate, vildagliptin, metformin, and Exendin-4; see Crouthamel et al., Clin Cancer Res, 15:217-225, 2009). Hyperglycemia induced by AKT inhibitors (a direct PI3K target) can be partially resolved by fasting in rodents, but hyperinsulinemia is not reduced. High PI3K coverage would thus appear to be unachievable in oncology since it is assumed that glucose cannot be regulated without insulin signaling.

Circulating glucose and metabolic homeostasis are regulated by the, equally important, opposing actions of insulin and glucagon (Unger and Cherrington, J Clin Invest., 122: 4-12, 2012). Activation of the hepatic glucagon receptor (GCGR) is directly responsible for decreased hepatic glucose uptake, increased hepatic glycogenolysis, increased hepatic gluconeogenesis, increased ketogenesis, and decreased glycogen synthesis, all of which increase circulating glucose (Unger and Orci, Lancet, 1:14-16, 1975). The main target organ of glucagon is the liver where GCGR is expressed at uniquely high levels. Activation of GCGR in hepatocytes stimulates the synthesis and the biochemical activity of key enzymes for glycogenolysis and gluconeogenesis resulting in increased hepatic glucose output. GCGR is expressed at much lower levels in other vital organs (e.g. small intestine, heart, brain, etc). However, receptor activity in these organs is much less important in the regulation of circulating glucose. It has been demonstrated that targeting glucagon production or function using isolated antagonistic antigen binding proteins that specifically bind to and antagonize the human GCGR are capable of controlling and lowering blood glucose, and improving glucose tolerance, in T2D models (see, e.g., U.S. Pat. No. 7,947,809 (Yan, et al)); and capable of normalizing blood glucose and hemoglobin A1c levels in the complete absence of insulin therapy, in type 1 diabetes (T1 D) models (see, e.g., PCT WO 2015/189698 (Hai and Shi)). In view of the fact that several prominent features of T2D and T1 D, including hyperglycemia, hyperinsulinemia, body weight loss, increased insulin resistance and decreased insulin production, are associated with treatment of cancers using PI3K pathway inhibitors, research efforts to develop novel treatments for cancer, e.g., ovarian and breast cancer, could benefit greatly from studies evaluating the effects of such antagonistic antigen binding proteins to effectively treat subjects who have, or who have been diagnosed with cancer.

The disclosures of all publications, patents, patent applications and published patent applications referred to herein are hereby incorporated herein by reference in their entirety.

DISCLOSURE OF THE INVENTION

The present disclosure is based in part on the inventor's unique insight that the clinical benefits of PI3K pathway inhibitors have been disappointing due not only to low target coverage, but due to an apparent metabolic reprogramming induced by treatment of patients with PI3K pathway inhibitors. The present inventors propose that GCGR inhibition in diabetic and non-diabetic cancer subjects for the purpose of preventing such metabolic reprogramming should potentiate the efficacy of PI3K pathway inhibitors in one or more of the following ways: 1) the growth promoting effects of excess glucose on the tumors would be decreased; 2) the reduction in PI3K induced hyperglycemia and hyperinsulinemia would reduce antagonism towards PI3K pathway inhibitors; 3) glucose normalization should extend the MTD enabling increased PI3K target coverage; and 4) GCGR blockage may potentiate PI3K inhibition of insulin signaling in the liver by increasing PTEN activity.

Thus, in one aspect, the present disclosure provides combination therapy methods of treating a subject having cancer, comprising administering to the subject a) an effective amount of a pharmaceutical composition comprising a phosphatidylinositol 3-kinase (PI3K) pathway inhibitor, or a pharmaceutically acceptable salt thereof and b) an effective amount of a pharmaceutical composition comprising a glucagon receptor antagonist. In various embodiments, the combination therapy methods comprise administering an effective amount of a pharmaceutical composition comprising a PI3K pathway inhibitor, or a pharmaceutically acceptable salt thereof, and a glucagon receptor antagonist antibody.

In various embodiments, the PI3K pathway inhibitor is a PI3K inhibitor selected from the group consisting of a PI3K alpha inhibitor, a PI3K beta inhibitor, a PI3K gamma inhibitor, a PI3K delta inhibitor, and a pan-PI3K isoform inhibitor. In various embodiments, the PI3K inhibitor is selected from the group consisting of: GDC-0941 (Genentech), BKM120 (NVP-BKM120)(Novartis), XL147 (Sanofi), PX-866 (Oncothyreon), BAY806946 (Bayer), CH5132799 (Chugai), BYL719 (NVP-BYL719)(Novartis), MLN1117 (Millennium), AZD8186 (Astra-Zeneca), SAR260301 (Sanofi), GSK2636771 (Glaxo Smith Kline), GS-1101 (Gilead), AMG 319 (Amgen), GS-9820 (Gilead), IPI-145 (Infinity), GDC-0032 (Genentech), and GDC-0084 (Genentech). In various embodiments, the PI3K inhibitor is BYL719.

In various embodiments, the PI3K pathway inhibitor is an insulin-like growth factor receptor 1 (IGFR1) small molecule tyrosine kinase inhibitor or monoclonal antibody. In various embodiments, the PI3K pathway inhibitor is an IGFR1 tyrosine kinase inhibitor selected from the group consisting of BMS 754807 (BMS), INSM-18 (Insmed/UCSF), OSI-906 (linsitinib)(Osi Pharmaceuticals), XL-228 (Exelixis), GSK 1904529A (GSK), ABDP (AZ), A-928605 (Abbott), AXL1717 (PPP) (Alexar), KW-2450 (Kyowa Kirin), NVP-ADW742 (Novartis), NVP-AEW541 (Novartis), AG-1024 (Merck), BMS-536924 (BMS), BMS-554417 (BMS), and BVP-51004 (Biovitrum). In various embodiments, the PI3K pathway inhibitor is an IGFR1 monoclonal antibody selected from the group consisting of: MK 0646 (dalotuzumab) (Merck), AMG 479 (ganitumumab) (Amgen), A12 (cixutumumab) (ImClone), CP 751,871 (figitumumab) (Pfizer), AVE1642 (Sanofi-Aventis), Sch717454 (robatumumab) (Schering-Merck), R 1507 (Roche), B11B022 (Biogen Idec), h10H5 (Genentech), MEDI-573 (Medimmune), and B1836845 (Boehringer-Ingleheim).

In various embodiments, the PI3K pathway inhibitor is an AKT kinase inhibitor selected from the group consisting of: miltefosine, perifosine, PF-04691502, CCT128930, A-674563, MK-2206 (Merck), RX-0201, PBI-05204, AZD5363 (Astra-Zeneca), AKTi-1/2, AT7867, AT13148, GDC-0068(Ipatasertib)(Genentech), TIC10, SC79, GSK690693, GSK2110183 and GSK2141795 (Glaxo Smith Kline).

In various embodiments, the PI3K pathway inhibitor is an mTOR inhibitor selected from the group consisting of: sirolimus, RAD001 (everolimus)(Novartis), CCI-779 (temsirolimus)(Wyeth-Pfizer), ABT578, SAR543, ascomycin, ridaforolimus, AP23573 (deforolimus)(Ariad/Merck), AP23841, KU-0063794, INK-128, EX2044, EX3855, EX7518, MK-8669, AZD08055, MLN0128, AZD2014, CC-223 and OSI027.

In various embodiments, the PI3K pathway inhibitor is a pan PI3K/mTOR inhibitor selected from the group consisting of: NVP-BEZ235 (Novartis), NVP-BGT226 (Novartis), XL765 (Sanofi), GSK1059615 (Glaxo Smith Kline), and GDC-0980 (Genentech).

In various embodiments, the glucagon receptor antagonist is an isolated antagonistic antigen binding protein that specifically binds to the human glucagon receptor. In various embodiments, the isolated antagonistic antigen binding protein comprises an antibody selected from the group consisting of a fully human antibody, a humanized antibody, a chimeric antibody, a monoclonal antibody, a polyclonal antibody, a recombinant antibody, an antigen-binding antibody fragment, a Fab, a Fab', a Fab$_2$, a Fab'$_2$, a IgG, a IgM, a IgA, a IgE, a scFv, a dsFv, a dAb, a nanobody, a unibody, and a diabody. In various embodiments, the antibody is a fully human monoclonal antibody.

In various embodiments, the isolated antibody or antigen-binding antibody fragment specifically binds to a human glucagon receptor with a dissociation constant ($K_D$) of at least about $1\times10^{-7}$ M, at least about $1\times10^{-8}$ M, at least about $1\times10^{-9}$ M, at least about $1\times10^{-10}$ M, at least about $1\times10^{-11}$ M, or at least about $1\times10^{-12}$ M.

In various embodiments, the isolated antagonistic antigen binding protein comprises an antibody which comprises the amino acid sequence encoding the heavy chain variable region of SEQ ID NO: 2 and the amino acid sequence encoding the light chain variable region of SEQ ID NO: 3. In various embodiments, the isolated antagonistic antigen binding protein comprises an antibody which comprises the amino acid sequence encoding the heavy chain variable region of SEQ ID NO: 4 and the amino acid sequence encoding the light chain variable region of SEQ ID NO: 5. In various embodiments, the isolated antagonistic antigen binding protein comprises an antibody which comprises the amino acid sequence encoding the heavy chain variable region of SEQ ID NO: 6 and the amino acid sequence encoding the light chain variable region of SEQ ID NO: 7. In various embodiments, the isolated antagonistic antigen binding protein comprises an antibody which comprises the amino acid sequence encoding the heavy chain of SEQ ID NO: 8 and the amino acid sequence encoding the light chain of SEQ ID NO: 9.

In various embodiments, the cancer selected from the group consisting of: B cell lymphoma; a lung cancer (small cell lung cancer and non-small cell lung cancer); a bronchus cancer; a colorectal cancer; a prostate cancer; a breast cancer; a pancreas cancer; a stomach cancer; an ovarian cancer; a urinary bladder cancer; a brain or central nervous system cancer; a peripheral nervous system cancer; an esophageal cancer; a cervical cancer; a melanoma; a uterine or endometrial cancer; a cancer of the oral cavity or pharynx; a liver cancer; a kidney cancer; a biliary tract cancer; a small bowel or appendix cancer; a salivary gland cancer; a thyroid gland cancer; an adrenal gland cancer; an osteosarcoma; a chondrosarcoma; a liposarcoma; a testes cancer; and a malignant fibrous histiocytoma; a skin cancer; a head and neck cancer; lymphomas; sarcomas; multiple myeloma; and leukemias. In various embodiments, the subject previously responded to treatment with an anti-cancer therapy, but, upon cessation of therapy, suffered relapse (hereinafter "a recurrent cancer"). In various embodiments, the subject has a cancer that is resistant or refractory to treatment using the PI3K pathway inhibitor alone, using another anti-cancer agent alone, or using the PI3K pathway inhibitor in combination with another anti-cancer agent.

In various embodiments, the combination therapy methods comprise administering the PI3K pathway inhibitor and glucagon receptor antagonist simultaneously, either in the same pharmaceutical composition or in separate pharmaceutical compositions. In various embodiments, the PI3K pathway inhibitor composition and the glucagon receptor antagonist composition are administered sequentially, i.e., the PI3K pathway inhibitor composition is administered either prior to or after the administration of the glucagon receptor antagonist composition. In various embodiments, the administration of the PI3K pathway inhibitor composition and the glucagon receptor antagonist composition are concurrent, i.e., the administration period of the PI3K pathway inhibitor composition and that of the glucagon receptor antagonist composition overlap with each other. In various embodiments, the administrations of the PI3K pathway inhibitor composition and the glucagon receptor antagonist composition are non-concurrent, e.g., in various embodiments the administration of the PI3K pathway inhibitor composition is terminated before the glucagon receptor antagonist composition is administered, and in various embodiments the administration of the glucagon receptor antagonist composition is terminated before the PI3K pathway inhibitor composition is administered.

In various embodiments, the methods may further comprise one or more additional therapies selected from the group consisting of: administration of anti-obesity agents (including appetite suppressants), anti-diabetic agents, anti-hyperglycemic agents, lipid lowering agents, anti-hypertensive agents, immunotherapy, chemotherapy, small molecule kinase inhibitor targeted therapy, surgery, radiation therapy, and stem cell transplantation.

In another aspect, the present disclosure relates to a pharmaceutical composition comprising a PI3K pathway inhibitor and/or a glucagon receptor antagonist, with one or more pharmaceutically acceptable carrier(s). In various embodiments, the pharmaceutical compositions are formulated to be administered via a route selected from the group consisting of: subcutaneous injection, intraperitoneal injection, intramuscular injection, intrasternal injection, intravenous injection, intraarterial injection, intrathecal injection, intraventricular injection, intraurethral injection, intracranial injection, intrasynovial injection and via infusions.

MODE(S) FOR CARRYING OUT THE INVENTION

Figure 1:
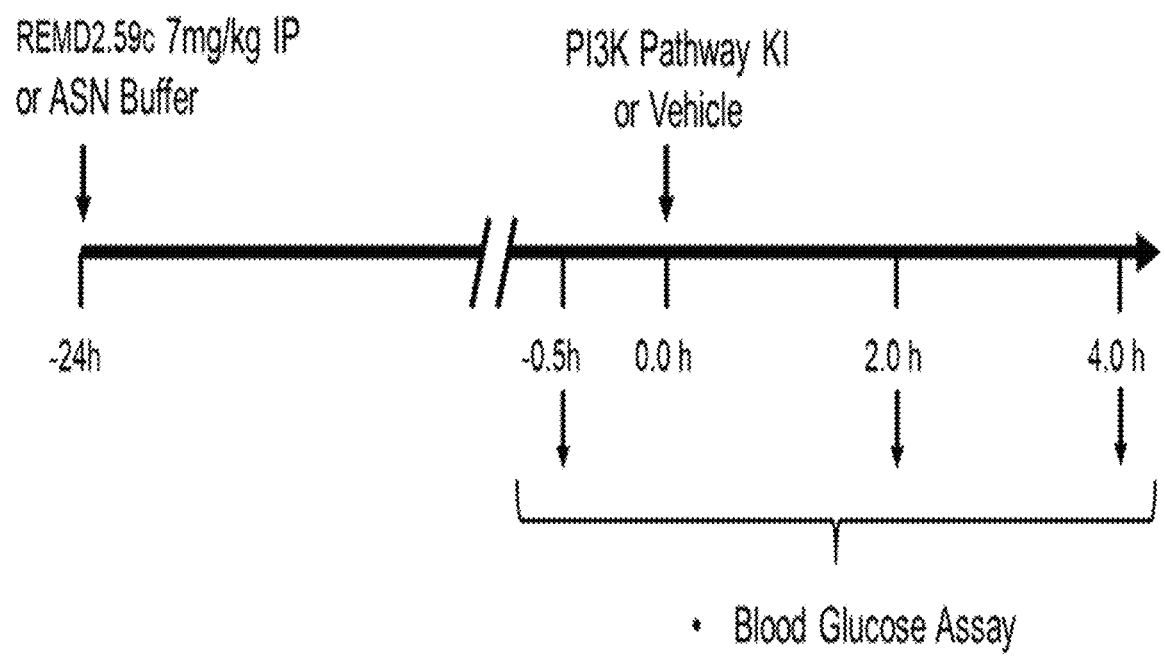
FIG. 1 is a schematic representation of the dosing and sampling protocol used to determine the effects of REMD2.59c pretreatment on the induction of hyperglycemia by PI3K/Akt pathway inhibitors in C57BL/6 fed mice.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those commonly used and well known in the art. The methods and techniques of the present disclosure are generally performed according to conventional methods well known in the art and as described in various general and more specific references that are cited and discussed throughout the present specification unless otherwise indicated. See, e.g., Green and Sambrook, Molecular Cloning: A Laboratory Manual, 4th ed., Cold Spring Harbor Laboratory Press, Cold Spring Harbor, N.Y. (2012), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of subjects.

Definitions

As used herein, "treatment" is an approach for obtaining beneficial or desired clinical results. For purposes of this invention, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, and remission (whether partial or total). Also encompassed by "treatment" is a reduction of pathological consequence of a proliferative disease. The methods of the invention contemplate any one or more of these aspects of treatment.

The term "effective amount" or "therapeutically effective amount" as used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective amount can be administered in one or more administrations.

"Adjuvant setting" refers to a clinical setting in which an individual has had a history of cancer, and generally (but not necessarily) been responsive to therapy, which includes, but is not limited to, surgery (such as surgical resection), radiotherapy, and chemotherapy. However, because of their history of the cancer, these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated.

The terms "patient," "individual," and "subject" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the patient can be a human (e.g., adult male, adult female, adolescent male, adolescent female, male child, female child) under the care of a physician or other health worker in a hospital, psychiatric care facility, as an outpatient, or other clinical context.

"Pharmaceutical composition" refers to a composition suitable for pharmaceutical use in a human. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

The phrase "administering" or "cause to be administered" refers to the actions taken by a medical professional (e.g., a physician), or a person controlling medical care of a patient, that control and/or permit the administration of the agent(s)/compound(s) at issue to the patient. Causing to be administered can involve diagnosis and/or determination of an appropriate therapeutic regimen, and/or prescribing particular agent(s)/compounds for a patient. Such prescribing can include, for example, drafting a prescription form, annotating a medical record, and the like. Where administration is described herein, "causing to be administered" is also contemplated.

As used herein, the terms "co-administration", "co-administered" and "in combination with", referring to the isolated glucagon receptor antagonists and PI3K pathway inhibitors of the present disclosure, is intended to mean, and does refer to and include the following: simultaneous administration of such combination of isolated glucagon receptor antagonist and PI3K pathway inhibitors to a subject in need of treatment, when such components are formulated together into a single dosage form which releases said components at substantially the same time to said subject; substantially simultaneous administration of such combination of isolated glucagon receptor antagonist and PI3K pathway inhibitors to a subject in need of treatment, when such components are formulated apart from each other into separate dosage forms which are taken at substantially the same time by said subject, whereupon said components are released at substantially the same time to said subject; sequential administration of such combination of isolated glucagon receptor antagonist and PI3K pathway inhibitors to a subject in need of treatment, when such components are formulated apart from each other into separate dosage forms which are taken at consecutive times by said subject with a significant time interval between each administration, whereupon said components are released at substantially different times to said subject; and sequential administration of such combination of isolated glucagon receptor antagonist and PI3K pathway inhibitors to a subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

As used herein, the terms "fixed dose" and "single formulation" refer to a single pharmaceutical composition formulated to deliver an amount, which is jointly therapeutically effective for the treatment of cancer, of both therapeutic agents to a patient. The single vehicle is designed to deliver an amount of each of the agents, along with any pharmaceutically acceptable carriers or excipients. In various embodiments, the vehicle is a tablet, capsule, pill, or a patch. In various embodiments, the vehicle is a solution or a suspension.

As used herein, The term "non-fixed combination" means that the active ingredients are both administered to a patient as separate entities either simultaneously, concurrently or sequentially with no specific time limits, wherein such administration provides therapeutically effective levels of the active ingredients to the patient. The latter also applies to cocktail therapy, e.g., the administration of three or more active ingredients.

"Resistant or refractory cancer" refers to tumor cells or cancer that do not respond to previous anti-cancer therapy including, e.g., PI3K inhibitor therapy, chemotherapy, surgery, radiation therapy, stem cell transplantation, and immunotherapy. Tumor cells can be resistant or refractory at the beginning of treatment, or they may become resistant or refractory during treatment. Refractory tumor cells include tumors that do not respond at the onset of treatment or respond initially for a short period but fail to respond to treatment. Refractory tumor cells also include tumors that respond to treatment with anticancer therapy but fail to respond to subsequent rounds of therapies. For purposes of this invention, refractory tumor cells also encompass tumors that appear to be inhibited by treatment with anticancer therapy but recur up to five years, sometimes up to ten years or longer after treatment is discontinued. The anticancer therapy can employ chemotherapeutic agents alone, radiation alone, targeted therapy alone, surgery alone, or combinations thereof. For ease of description and not limitation, it will be understood that the refractory tumor cells are interchangeable with resistant tumor.

As used herein, the term "immunotherapy" refers to cancer treatments which include, but are not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints) such as CTLA-4, PD-1, OX-40, CD137, GITR, LAGS, TIM-3, and VISTA; treatment using bispecific T cell engaging antibodies (BiTE®) such as blinatumomab: treatment involving administration of biological response modifiers such as IL-2, IL-12, IL-15, IL-21, GM-CSF, IFN-α, IFN-β and IFN-γ; treatment using therapeutic vaccines such as sipuleucel-T; treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic); treatment using TALL-104 cells; and treatment using immunostimulatory agents such as Toll-like receptor (TLR) agonists CpG and imiquimod.

The terms "peptide" "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric. In certain embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "therapeutic protein" refers to proteins, polypeptides, antibodies, peptides or fragments or variants thereof, having one or more therapeutic and/or biological activities. Therapeutic proteins encompassed by the invention include but are not limited to, proteins, polypeptides, peptides, antibodies, and biologics. (The terms peptides, proteins, and polypeptides are used interchangeably herein.) It is specifically contemplated that the term "Therapeutic protein" encompasses antibodies and fragments and variants thereof.

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular section of a polypeptide can be designated by amino acid residue number such as amino acids 80 to 119, or by the actual residue at that site such as Ser80 to Ser119. A particular polypeptide or polynucleotide sequence also can be described by explaining how it differs from a reference sequence.

Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

Alanine (A), Serine (S), and Threonine (T)
Aspartic acid (D) and Glutamic acid (E)
Asparagine (N) and Glutamine (Q)
Arginine (R) and Lysine (K)
Isoleucine (I), Leucine (L), Methionine (M), and Valine (V)
Phenylalanine (F), Tyrosine (Y), and Tryptophan (W)

A "non-conservative amino acid substitution" refers to the substitution of a member of one of these classes for a member from another class. In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8);

glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. Exemplary amino acid substitutions are set forth in Table 1.

TABLE 1

| Original Residues | Exemplary Substitutions | Preferred Substitutions |
|---|---|---|
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a polypeptide that correspond to amino acid residues important for activity or structure in similar polypeptides. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three-dimensional structure. In certain embodiments, one skilled in the art may choose to not make radical changes to amino acid residues predicted to be on the surface of the polypeptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "polypeptide fragment" and "truncated polypeptide" as used herein refers to a polypeptide that has an amino-terminal and/or carboxy-terminal deletion as compared to a corresponding full-length protein. In certain embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In certain embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant" and "polypeptide mutant" as used herein refers to a polypeptide that comprises an amino acid sequence wherein one or more amino acid residues are inserted into, deleted from and/or substituted into the amino acid sequence relative to another polypeptide sequence. In certain embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Variants of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. In certain embodiments, the % identity is selected from, e.g., at least 60%, at least 65%, at least 70%, at least 75%, at least 80%, at least 85%, at least 90%, at least 95%, or at least 99% or more sequence identity to a given sequence. In certain embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In certain embodiments, the % homology is selected from, e.g., at least 60%, at least 65%, at least 70%, at least 75%, at least 80%, at least 85%, at least 90%, at least 95%, or at least 99% or more sequence homology to a given sequence. In certain embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. (Id).

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. A substantially pure polypeptide or protein will typically comprise about 50%, 60%, 70%, 80% or 90% W/W of a protein sample, more usually about 95%, and e.g., will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

An "antigen binding and antagonizing protein" is a protein comprising a portion that binds to an antigen and, optionally, a scaffold or framework portion that allows the antigen binding portion to adopt a conformation that promotes binding of the isolated antagonistic antigen binding protein to the antigen. Examples of antigen binding and antagonizing proteins include antibodies, antibody fragments (e.g., an antigen binding portion of an antibody), antibody derivatives, and antibody analogs. The isolated antagonistic antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the isolated antagonistic antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129

(2003); Roque et al., Biotechnol. Prog. 20:639-654 (2004). In addition, peptide antibody mimetics ("PAMs") can be used, as well as scaffolds based on antibody mimetics utilizing fibronection components as a scaffold.

An isolated antagonistic antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

An "antibody" refers to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

In a full-length antibody, each heavy chain is comprised of a heavy chain variable region (abbreviated herein as HCVR or $V_H$) and a heavy chain constant region. The heavy chain constant region is comprised of three domains, $C_{H1}$, $C_{H2}$ and $C_{H3}$ (and in some instances, $C_{H4}$). Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: $FR_1$, $CDR_1$, $FR_2$, $CDR_2$, $FR_3$, $CDR_3$, $FR_4$. The extent of the framework region and CDRs has been defined. The sequences of the framework regions of different light or heavy chains are relatively conserved within a species, such as humans. The framework region of an antibody, that is the combined framework regions of the constituent light and heavy chains, serves to position and align the CDRs in three-dimensional space. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

Antibodies exist as intact immunoglobulins or as a number of well characterized fragments. Such fragments include Fab fragments, Fab' fragments, $Fab_2$, $F(ab')_2$ fragments, single chain Fv proteins ("scFv") and disulfide stabilized Fv proteins ("dsFv"), that bind to the target antigen. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. While various antibody fragments are defined in terms of the digestion of an intact antibody, one of skill will appreciate that such fragments may be synthesized de novo either chemically or by utilizing recombinant DNA methodology. Thus, as used herein, the term antibody encompasses e.g., monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, $F(ab')_2$ fragments, antibody fragments that exhibit the desired biological activity, disulfide-linked Fvs (sdFv), intrabodies, and epitope-binding fragments or antigen binding fragments of any of the above.

A Fab fragment is a monovalent fragment having the $V_L$, $V_H$, $C_L$ and $C_{H1}$ domains; a $F(ab')_2$ fragment is a bivalent fragment having two Fab fragments linked by a disulfide bridge at the hinge region; a Fd fragment has the $V_H$ and C.sub.H1 domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, U.S. application Pub. Ser. No. 05/0,202,512, 04/0,202,995, 04/0,038,291, 04/0,009,507, 03/0,039,958, Ward et al., Nature 341:544-546 (1989)).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., Science 242:423-26 (1988) and Huston et al., 1988, Proc. Natl. Acad. Sci. USA 85:5879-83 (1988)). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48 (1993), and Poljak et al., Structure 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

An isolated antagonistic antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

An isolated antagonistic antigen binding protein of the present disclosure, including an antibody, "specifically binds" to an antigen, such as the human glucagon receptor if it binds to the antigen with a high binding affinity as determined by a dissociation constant (Kd, or corresponding Kb, as defined below) value of $10^{-7}$ M or less. An isolated antagonistic antigen binding protein that specifically binds to the human glucagon receptor may be able to bind to glucagon receptors from other species as well with the same or different affinities.

An "epitope" is the portion of a molecule that is bound by an isolated antagonistic antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding and antagonizing protein).

The term "blood glucose level", or "level of blood glucose" shall mean blood glucose concentration. In certain embodiments, a blood glucose level is a plasma glucose level. Plasma glucose may be determined in accordance with, e.g., Etgen et al., Metabolism, 49(5): 684-688, 2000) or calculated from a conversion of whole blood glucose concentration in accordance with D'Orazio et al., Clin. Chem. Lab. Med., 44(12):1486-1490, 2006.

The term "normal glucose levels" refers to mean plasma glucose values in humans of less than about 100 mg/dL for fasting levels, and less than about 145 mg/dL for 2-hour post-prandial levels or 125 mg/dL for a random glucose. The term "elevated blood glucose level" or "elevated levels of blood glucose" shall mean an elevated blood glucose level such as that found in a subject demonstrating clinically inappropriate basal and postprandial hyperglycemia or such as that found in a subject in oral glucose tolerance test (oGTT), with "elevated levels of blood glucose" being greater than about 100 mg/dL when tested under fasting conditions, and greater than about 200 mg/dL when tested at 1 hour.

The terms "glucagon inhibitor", "glucagon suppressor" and "glucagon antagonist" are used interchangeably. Each is a molecule that detectably inhibits glucagon signaling. The inhibition caused by an inhibitor need not be complete so long as the inhibition is detectable using an assay that is recognized and understood in the art as being determinative of glucagon signaling inhibition.

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variation.

Reference to "about" a value or parameter herein includes (and describes) variations that are directed to that value or parameter per se. For example, description referring to "about X" includes description of "X".

PI3K Pathway Inhibitors
Phosphatidylinositol 3-Kinase (PI3K) Inhibitors

PI3Ks are a family of lipid kinases that lie upstream of complex, intricate, interconnected intracellular signaling networks, and that transduce signals from transmembrane receptors such as RTKs and G-protein coupled receptors (GPCRs) to the cytoplasm—through production of phosphorylated lipids—to regulate key cellular processes including proliferation, differentiation, senescence, motility, and survival (Liu P, Nat Rev Drug Discov., 8(8):627-644, 2009). PI3Ks are enzymes of approximately 200-300 kDa in molecular weight. In human, three distinct classes of PI3Ks (I-III) have been identified and that differ on basis of their structural characteristics, substrate specificities, and nature of lipid end-products. The class I enzymes consist of heterodimers having a regulatory (p85) domain and a catalytic (p110) subunit, of which there are four isoforms: p110α, p110β, p110Δ, and p110γ. The α isoform and β isoform are ubiquitously expressed; α is linked upstream mainly to receptor tyrosine kinases, whereas β can mediate signals from both G-protein-coupled receptors and from receptor tyrosine kinases. The Δ isoform and γ isoform are expressed primarily in lymphocytes and play important roles in the regulation of immune responses. Class I PI3Ks are heterodimers and further divided into 2 subfamilies, IA and IB. Class IA PI3Ks are the most studied and frequently implicated in cancer (Courtney K, J Clin Oncol., 28(6):1075-1083, 2010). PI3K inhibitors are divided into three classes, pan-class 1, isoform-selective PI3K inhibitors, and dual PI3K/mTOR inhibitors, based on pharmacokinetic properties and isoform selectivity for the ATP binding site of PI3Ks (Vadas O, et al, Sci Signal., 4(195), 2011).

The PI3K inhibitors contemplated for use in the pharmaceutical compositions and combination therapies of the present disclosure may be any compound or compounds described in the art as capable of inhibiting PI3K. In various embodiments, the pharmaceutical composition of the present disclosure comprises a PI3K inhibitor selected from the group consisting of: a PI3K alpha inhibitor, a PI3K beta inhibitor, a PI3K gamma inhibitor, a PI3K delta inhibitor, and a pan-PI3K isoform inhibitor, or a pharmaceutically acceptable salt thereof.

Non-limiting examples of PI3K inhibitors contemplated for use include: LY-294002, Wortmannin, BEZ235 (NVP-BEZ235), GDC-0941 (Genentech), PI-103, BKM120 (NVP-BKM120)(Novartis), CAL-101 (GS-1101), IC-87114, GSK2636771, TG 100713, BYL719 (NVP-BYL719)(Novartis), PI3K/HDAC inhibitor 1, 3-Methyladenine, YM201636, NVP-BGT226, BAY80-6946, PF-04691502, PKI-402, CH5132799 (Chugai), GDC-0980 (RG7422), NU 7026, NU 7441 (KU-57788), AS-252424, AS-604850, AS-041164, CAY10505, GSK2126458, A66, PF-05212384 (PKI-587), PIK-294, PIK-293, XL765, PIK-93, AZD6482, AS-605240, GSK1059615, TG100-115, PIK-75, PIK-90, TGX-115, TGX-221, XL147 (Sanofi), ZSTK474, quercetin, tetrodotoxin citrate, thioperamide maleate, PI103, (−)-degiielin, OSU03012, tandutinib, GSK690693, KU-55933, MK-2206, perifosine, triciribine, PI 828, WII-P 154, compound 15e,17-P-hydroxywortmannin, Pp 121, PX-478, PX-866, PX-867, WAY-266176, WAY-266175, SF1126, 07412, LC-486068, and LME00084. In various embodiments, the PI3K inhibitor is selected from the group consisting of: GDC-0941 (Genentech), BKM120 (NVP-BKM120)(Novartis), XL147 (Sanofi), PX-866 (Oncothyreon), BAY806946 (Bayer), CH5132799 (Chugai), BYL719 (NVP-BYL719)(Novartis), MLN1117 (Millennium), AZD8186 (Astra-Zeneca), SAR260301 (Sanofi), GSK2636771 (Glaxo Smith Kline), GS-1101 (Gilead), AMG 319 (Amgen), GS-9820 (Gilead), IPI-145 (Infinity), GDC-0032 (Genentech), and GDC-0084 (Genentech).

BYL719 (NVP-BYL719)(Novartis) is an isoform selective PIK3 kinase inhibitor that inhibits both wild-type and mutant enzyme (Furet, P., et al., Bioorganic & Medicinal Chemistry Letters, 23(13):3741-3748, 2013). The quantitative relationship between circulating NVP-BYL719 concentration, PI3KCA coverage, hyperglycemia, hyperinsulinemia, weight loss, and tumor growth inhibition has been defined in a comprehensive pharmacological study (Fritsch, C., et al., Mol Cancer Ther, 13(5):1117-29, 2014).

In various embodiments of the present disclosure, the PI3K inhibitor is BYL719 (PubChem CID 56649450). In various embodiments of the present disclosure, the PI3K inhibitor is BKM120 (PubChem CID 16654980). In various embodiments of the present disclosure, the PI3K inhibitor is MK2206 (PubChem CID 24964624).

Additional examples of PI3K inhibitors, or a pharmaceutically acceptable salt thereof are described in, e.g., U.S. Pat. Nos. 9,150,579; 9,335,320; 8,980,259; 7,173,029; 7,037,915; 6,608,056; 6,608,053; 6,838,457; 6,770,641; 6,653,320; 6,403,588; 7,750,002; 7,872,003; US 2014/0235630; US 2015/0141426; US 2016/0039793; US 2015/0342951; US 2015/0265616; US 2004/0092561; US 2003/0149074; US 2011/0230476, US 2009/0312319, US 2011/0281866, US 2011/0269779, US 2010/0249099, US 2011/0009405; WO 2006/046035; WO 2007/042806; WO 2007/042810; WO 2004/017950; WO 2004/007491; WO 2004/006916; WO 2003/037886; WO2012146667, WO2012135009, WO2012140419; WO 2007/044729 and WO 2010/029082, each herein incorporated by reference in its entirety.

IR/IGFR1 Tyrosine Kinase Inhibitors—IGFR1 Monoclonal Antibodies

The critical role of IGF signaling in initiating and promoting tumor progression has resulted in it becoming an attractive target for cancer therapy. Various strategies have been used to target components of this system both in vitro and in vivo, some of which have advanced to clinical use. The general aim of these approaches is to interfere with the function of IGF system components by methods including small interfering RNA, antisense oligonucleotides, antisense RNA, triple helix-forming oligodeoxynucleotides, specific kinase inhibitors, single chain antibodies and fully humanized anti-IGF1R monoclonal antibodies (Heidegger et al, Cancer Biol Ther, 11(8), 701-707, 2011). The two most thoroughly investigated strategies for IGF1R inhibition are small-molecule tyrosine kinase inhibitors and monoclonal antibodies, both of which have various advantages and display different activity profiles. Studies have concentrated on modulating IGF1R tyrosine kinase activity by targeting its intracellular kinase domain.

A variety of IGF1R small-molecule tyrosine kinase inhibitors and monoclonal antibodies are known in the art. Non-limiting examples of such IGF1R inhibitors contemplated for use include: BMS 754807; OSI-906 (linsitinib); figitumumab (CP-751871); NT52; INSM-18; NVP-AEW541; NVP-ADW742; aIR3; IGF1R scFv-Fc; 486/STOP; 950/STOP; N-(2-methoxy-5-chlorophenyl)-N'-(2-methylquinolin-4-yl)-urea; BMS-754807; IGF-IRi; AG1024; R1507; AXL-1717; picropodophyllotoxin; PQ401; dalotuzumab; A-928605; KW-2450; BMS-536924; IMC-Al2; CP-751871; n-(5-chloro-2-methoxyphenyl)-N'-(2-methoxyquinolin-4-yl)-urea; TAE226; BMS-554417; MK-0646; BMS-536924; MAE87; XL 228; AGL 2263; I-OMe-AG538; AG538; OSI-868; BMS-754807; ADW742; NVP-ADW642; R1507; MK-0646; A928605; MAB391; BMS-536942; IMC-Al2; rhIGFBP3, ANT-429, ATL-1101, BVP-51004, JV-1-38, pegvisomant, A-928605, and picropodophyliin (PPP) (CAS 477-47-4).

In various embodiments, the PI3K pathway inhibitor is an IGFR1 tyrosine kinase inhibitor selected from the group consisting of BMS 754807 (BMS), INSM-18 (Insmed/UCSF), OSI-906 (linsitinib)(Osi Pharmaceuticals), XL-228 (Exelixis), GSK 1904529A (GSK), ABDP (AZ), A-928605 (Abbott), AXL1717 (PPP) (Alexar), KW-2450 (Kyowa Kirin), NVP-ADW742 (Novartis), NVP-AEW541 (Novartis), AG-1024 (Merck), BMS-536924 (BMS), BMS-554417 (BMS), and BVP-51004 (Biovitrum).

In various embodiments, the PI3K pathway inhibitor is an IGFR1 monoclonal antibody selected from the group consisting of: MK 0646 (dalotuzumab) (Merck), AMG 479 (ganitumumab) (Amgen), A12 (cixutumumab) (ImClone), CP 751,871 (figitumumab) (Pfizer), AVE1642 (Sanofi-Aventis), Sch717454 (robatumumab) (Schering-Merck), R 1507 (Roche), BIIB022 (Biogen Idec), h10H5 (Genentech), MEDI-573 (Medimmune), and B1836845 (Boehringer-Ingleheim).

Additional examples of IGF1R inhibitors are described in U.S. Pat. Nos. 8,895,008; 8,580,254; 8,318,159; 8,168,409; 7,985,842; 7,638,621; 7,638,605; 7,605,272; 7,538,195, 7,521,453; 7,432,244; and 6,071,891 (each herein incorporated by reference); and U.S. Patent Application Publication Nos. 2015/0274829; 20150259422; 2015/0183860; 2013/0287763; 20130236457; 2012/0208721; 2010/0047243; 2010/0028342; 2009/0099229; 2009/0099133; 2009/0054508; 2008/0025990; 2008/0161278; 2008/0152649; 2007/0185319; 2007/0275922; 2007/0129399; 2007/0123491; 2005/0054638; and 2004/0213792, each herein incorporated by reference in its entirety.

AKT Kinase Inhibitors

AKT/protein kinase B (PKB) has been shown to be a widely expressed Ser/Thr protein kinase whose persistent activation leads to human oncogenesis. AKT is believed to assert its effect on cancer by suppressing apoptosis and enhancing both angiogenesis and proliferation (Toker et al. (2006) Cancer Res. 66(8):3963-3966). AKT is overexpressed in many forms of human cancer including, but not limited to, colon (Zinda et al (2001) Clin. Cancer Res. 7:2475), ovarian (Cheng et al (1992) Proc. Natl. Acad. Sci. USA 89:9267), brain (Haas Kogan et al (1998) Curr. Biol. 8:1195), lung (Brognard et al (2001) Cancer Res. 61:3986), pancreatic (Bellacosa et al (1995) Int. J. Cancer 64:280-285; Cheng et al (1996) Proc. Natl. Acad. Sci. 93:3636-3641), prostate (Graff et al (2000) J. Biol. Chem. 275:24500) and gastric carcinomas (Staal et al (1987) Proc. Natl. Acad. Sci. USA 84:5034-5037).

There has been significant interest in AKT for its structural and functional properties as well as its implications in the area of cancer therapy. The AKT family consists of three members, AKT1 (PKBα), AKT2 (PKBβ), and AKT3 (PKBγ); that are structurally very similar (>85% sequence homology). Each isoform consists of an N-terminal pleckstrin homology (PH) domain, a central catalytic domain, and a C-terminal regulatory tail. Inhibition of AKT activity has been shown to suppress cell growth and induce apoptosis in tumor cell lines derived from various organs possessing constitutively activated AKT. Certain AKT kinase inhibitors are known as ATP-competitive inhibitors, for their ability to compete with ATP for binding to the active site of AKT. Certain AKT kinase inhibitors known as allosteric inhibitors do not bind to the active site of AKT. Also, AKT kinase inhibitors can be pan-AKT inhibitors, wherein the inhibitor can inhibit the activity of two or more of AKT1, AKT2 and AKT3. AKT kinase inhibitors can be selective AKT inhibitors, wherein the inhibitor can inhibit the activity of one of AKT1, AKT2 and AKT3, without inhibiting the activity of the other two.

In various embodiments, the PI3K pathway inhibitor is an AKT kinase inhibitor selected from the group consisting of: miltefosine, perifosine, PF-04691502, CCT128930, A-674563, MK-2206 (Merck), RX-0201, PBI-05204, AZD5363 (Astra-Zeneca), AKTi-1/2, AT7867, AT13148, GDC-0068(Ipatasertib)(Genentech), TIC10, SC79, GSK690693, GSK2110183 and GSK2141795 (Glaxo Smith Kline).

Additional examples of AKT inhibitors are described in U.S. Pat. Nos. 9,156,853; 9,150,549; and 8,481,503; U.S. Patent Application Publication Nos. 2016/0153049; 20150064171; 2014/0275106; and 2013/0287763 and WO 2011/055115, WO 2008/070134, WO 2008/070016 and WO 2008/070041 each herein incorporated by reference in its entirety.

mTOR Inhibitors

The mammalian target of Rapamycin, mTOR, is a cell-signaling protein that regulates the response of tumor cells to nutrients and growth factors, as well as controlling tumor blood supply through effects on Vascular Endothelial Growth Factor, VEGF. mTOR functions as a catalytic subunit for two distinct molecular complexes, mTOR complex 1 (mTORC1) and mTOR complex 2 (mTORC2). Inhibitors of mTOR starve cancer cells and shrink tumors by inhibiting the effect of mTOR. There are two important effects as mTOR inhibitors bind to the mTOR kinase. First, mTOR is a downstream mediator of the PI3K/AKT pathway. The PI3K/AKT pathway is thought to be over-activated in numerous cancers and may account for the widespread response from various cancers to mTOR inhibitors. It has been shown that mTOR inhibition can induce upstream insulin-like growth factor 1 receptor (IGF1R) signaling resulting in AKT activation in cancer cells. The over-activation of the upstream pathway would normally cause mTOR kinase to be over-activated as well. However, in the presence of mTOR inhibitors, this process is blocked. The blocking effect prevents mTOR from signaling to downstream pathways that control cell growth. The second major effect of mTOR inhibition is antiangiogenesis via the lowering of VEGF levels.

There are two broad categories of available mTOR inhibitors: the allosteric inhibitors, which are derivatives of rapamycin and commonly referred to as "rapalogs" (mTORC1 inhibitors), and the novel small molecule mTOR inhibitors. In various embodiments, the PI3K pathway inhibitor is an mTOR inhibitor selected from the group consisting of: sirolimus, RAD001 (everolimus)(Novartis), CCI-779 (temsirolimus)(Wyeth-Pfizer), ABT578, SAR543, ascomycin, ridaforolimus, AP23573 (deforolimus)(Ariad/Merck), AP23841, KU-0063794, INK-128, EX2044, EX3855, EX7518, MK-8669, AZD8055, MLN0128, AZD2014, CC-223 and OSI-027.

In various embodiments, the PI3K pathway inhibitor is a pan PI3K/mTOR inhibitor selected from the group consisting of: NVP-BEZ235 (Novartis), NVP-BGT226 (Novartis), XL765 (Sanofi), GSK1059615 (Glaxo Smith Kline), and GDC-0980 (Genentech).

Glucagon Receptor and Antigen Binding and Antagonizing Proteins

Glucagon is a 29 amino acid hormone processed from its pre-pro-form in the pancreatic alpha cells by cell specific expression of prohormone convertase 2 (PC2), a neuroendocrine-specific protease involved in the intracellular maturation of prohormones and proneuropeptides (Furuta et al., J. Biol. Chem. 276: 27197-27202 (2001)). In vivo, glucagon is a major counter-regulatory hormone for insulin actions. During fasting, glucagon secretion increases in response to falling glucose levels. Increased glucagon secretion stimulates glucose production by promoting hepatic glycogenolysis and gluconeogenesis (Dunning and Gerich, Endocrine Reviews, 28:253-283 (2007)). Thus glucagon counterbalances the effects of insulin in maintaining normal levels of glucose in animals.

The biological effects of glucagon are mediated through the binding and subsequent activation of a specific cell surface receptor, the glucagon receptor. The glucagon receptor (GCGR) is a member of the secretin subfamily (family B) of G-protein-coupled receptors. The human GCGR is a 477 amino acid sequence GPCR and the amino acid sequence of GCGR is highly conserved across species (Mayo et al, Pharmacological Rev., 55:167-194, (2003)). The glucagon receptor is predominantly expressed in the liver, where it regulates hepatic glucose output, on the kidney, and on islet β-cells, reflecting its role in gluconeogenesis. The activation of the glucagon receptors in the liver stimulates the activity of adenyl cyclase and phosphoinositol turnover which subsequently results in increased expression of gluconeogenic enzymes including phosphoenolpyruvate carboxykinase (PEPCK), fructose-1,6-bisphosphatase (FBPase-1), and glucose-6-phosphatase (G-6-Pase). In addition, glucagon signaling activates glycogen phosphorylase and inhibits glycogen synthase. Studies have shown that higher basal glucagon levels and lack of suppression of postprandial glucagon secretion contribute to diabetic conditions in humans (Muller et al., N Eng J Med 283: 109-115 (1970)). As such, methods of controlling and lowering blood glucose by targeting glucagon production or function using a GCGR antagonist have been explored.

In various embodiments, the antigen binding and antagonizing proteins of the present disclosure may be selected to bind to membrane-bound glucagon receptors as expressed on cells, and inhibit or block glucagon signaling through the glucagon receptor. In various embodiments, the antigen binding and antagonizing proteins of the present disclosure specifically bind to the human glucagon receptor. In various embodiments, the antigen binding and antagonizing proteins binding to the human glucagon receptor may also bind to the glucagon receptors of other species. The polynucleotide and polypeptide sequences for several species of glucagon receptor are known (see, e.g., U.S. Pat. No. 7,947,809, herein incorporated by reference in its entirety for its specific teaching of polynucleotide and polypeptide sequences of a human, rat, mouse and cynomolgus glucagon receptor). In various embodiments of the present disclosure, the antigen binding and antagonizing proteins specifically bind the human glucagon receptor having the amino acid sequence set forth in SEQ ID NO: 1:

Glucagon Receptor Human (Homo sapiens) amino acid sequence (Accession Number AAI04855)
(SEQ ID NO: 1)
MPPCQPQRPLLLLLLLLACQPQVPSAQVMDFLFEKWKLYGDQCHHNLSLL

PPPTELVCNRTFDKYSCWPDTPANTTANISCPWYLPWHHKVQHRFVFKRC

GPDGQWVRGPRGQPWRDASQCQMDGEEIEVQKEVAKMYSSFQVMYTVGYS

LSLGALLLALAILGGLSKLHCTRNAIHANLFASFVLKASSVLVIDGLLRT

RYSQKIGDDLSVSTWLSDGAVAGCRVAAVFMQYGIVANYCWLLVEGLYLH

NLLGLATLPERSFFSLYLGIGWGAPMLFVVPWAVVKCLFENVQCWTSNDN

MGFWWILRFPVFLAILINFFIFVRIVQLLVAKLRARQMHHTDYKFRLAKS

TLTLIPLLGVHEVVFAFVTDEHAQGTLRSAKLFFDLFLSSFQGLLVAVLY

CFLNKEVQSELRRRWHRWRLGKVLWEERNTSNHRASSSPGHGPPSKELQF

GRGGGSQDSSAETPLAGGLPRLAESPF

In various embodiments, the antigen binding and antagonizing proteins of the present disclosure specifically bind glucagon receptors which have at least 70%, at least 75%, at least 80%, at least 85%, at least 90%, at least 95%, at least 96%, at least 97%, at least 98%, or at least 99% identity (as calculated using methods known in the art and described herein) to the glucagon receptors described in the cited references are also included in the present disclosure.

The antigen binding and antagonizing proteins of the present disclosure function to block the interaction between glucagon and its receptor, thereby inhibiting the glucose elevating effects of glucagon. As such, the use of the antigen binding and antagonizing proteins of the present disclosure are an effective means of achieving normal levels of glucose, thereby ameliorating, or preventing one or more symptoms of, or long term complications caused by diabetes including, but not limited to, hyperglycemia, hyperglucanemia, and hyperinsulinemia.

Methods of generating antibodies that bind to antigens such as the human glucagon receptor are known to those skilled in the art. For example, a method for generating a monoclonal antibody that binds specifically to a targeted antigen polypeptide may comprise administering to a mouse an amount of an immunogenic composition comprising the targeted antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the targeted antigen polypeptide. Once obtained, a hybridoma can be propagated in a cell culture, optionally in culture conditions where the hybridoma-derived cells produce the monoclonal antibody that binds specifically to targeted antigen polypeptide. The monoclonal antibody may be purified from the cell culture. A variety of different techniques are then available for testing an antigen/antibody interaction to identify particularly desirable antibodies.

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. (U.S.A.), 90: 2551-2555, 1993; Jakobovits et al., Nature, 362: 255-258, 1993; Lonberg et al., U.S. Pat. No. 5,545,806; and Surani et al., U.S. Pat. No. 5,545,807.

Antibodies can be engineered in numerous ways. They can be made as single-chain antibodies (including small modular immunopharmaceuticals or SMIPs™), Fab and F(ab')2 fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al., Science, 240:1041-1043, 1988; Liu et al., Proc. Natl. Acad. Sci. (U.S.A.), 84:3439-3443, 1987; Liu et al., J. Immunol., 139:3521-3526, 1987; Sun et al., Proc. Natl. Acad. Sci. (U.S.A.), 84:214-218, 1987; Nishimura et al., Canc. Res., 47:999-1005, 1987; Wood et al., Nature, 314:446-449, 1985; and Shaw et al., J. Natl Cancer Inst., 80:1553-1559, 1988).

Methods for humanizing antibodies have been described in the art. In some embodiments, a humanized antibody has one or more amino acid residues introduced from a source that is nonhuman, in addition to the nonhuman CDRs. Humanization can be essentially performed following the method of Winter and co-workers (Jones et al., Nature, 321:522-525, 1986; Riechmann et al., Nature, 332:323-327, 1988; Verhoeyen et al., Science, 239:1534-1536, 1988), by substituting hypervariable region sequences for the corresponding sequences of a human antibody. Accordingly, such "humanized" antibodies are chimeric antibodies (U.S. Pat. No. 4,816,567) wherein substantially less than an intact human variable region has been substituted by the corresponding sequence from a nonhuman species. In practice, humanized antibodies are typically human antibodies in which some hypervariable region residues and possibly some framework region residues are substituted by residues from analogous sites in rodent antibodies.

U.S. Pat. No. 5,693,761 to Queen et al, discloses a refinement on Winter et al. for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable region sequences are compared to a particular mouse sequence and the percentage identity between correspondent framework residues is calculated. The human variable region with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6A of any CDR residue.

In other approaches, the importance of particular framework amino acid residues is determined experimentally once a low-avidity humanized construct is obtained, by reversion of single residues to the mouse sequence and assaying antigen binding as described by Riechmann et al, 1988. Another example approach for identifying important amino acids in framework sequences is disclosed by U.S. Pat. No. 5,821,337 to Carter et al, and by U.S. Pat. No. 5,859,205 to Adair et al. These references disclose specific Kabat residue positions in the framework, which, in a humanized antibody may require substitution with the correspondent mouse amino acid to preserve avidity.

Another method of humanizing antibodies, referred to as "framework shuffling", relies on generating a combinatorial library with nonhuman CDR variable regions fused in frame into a pool of individual human germline frameworks (Dall'Acqua et al., Methods, 36:43, 2005). The libraries are then screened to identify clones that encode humanized antibodies which retain good binding.

The choice of human variable regions, both light and heavy, to be used in making the humanized antibodies is very important to reduce antigenicity. According to the so-called "best-fit" method, the sequence of the variable region of a rodent antibody is screened against the entire library of known human variable-domain sequences. The human sequence that is closest to that of the rodent is then accepted as the human framework region (framework region) for the humanized antibody (Sims et al., J. Immunol., 151:2296, 1993; Chothia et al., J. Mol. Biol., 196:901, 1987). Another method uses a particular framework region derived from the consensus sequence of all human antibodies of a particular subgroup of light or heavy chain variable regions. The same framework may be used for several different humanized antibodies (Carter et al., Proc. Natl. Acad. Sci. (U.S.A.), 89:4285, 1992; Presta et al., J. Immunol., 151:2623, 1993).

The choice of nonhuman residues to substitute into the human variable region can be influenced by a variety of factors. These factors include, for example, the rarity of the amino acid in a particular position, the probability of interaction with either the CDRs or the antigen, and the probability of participating in the interface between the light and heavy chain variable domain interface. (See, for example, U.S. Pat. Nos. 5,693,761, 6,632,927, and 6,639,055). One method to analyze these factors is through the use of three-dimensional models of the nonhuman and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, nonhuman residues can be selected and substituted for human variable region residues in order to achieve the desired antibody characteristic, such as increased affinity for the target antigen(s).

Methods for making fully human antibodies have been described in the art. By way of example, a method for producing an anti-GCGR antibody or antigen binding antibody fragment thereof comprises the steps of synthesizing a library of human antibodies on phage, screening the library with GCGR or an antibody binding portion thereof, isolating phage that bind GCGR, and obtaining the antibody from the phage. By way of another example, one method for preparing the library of antibodies for use in phage display techniques comprises the steps of immunizing a non-human animal comprising human immunoglobulin loci with GCGR or an antigenic portion thereof to create an immune response, extracting antibody-producing cells from the immunized animal; isolating RNA encoding heavy and light chains of antibodies of the disclosure from the extracted cells, reverse transcribing the RNA to produce cDNA, amplifying the cDNA using primers, and inserting the cDNA into a phage display vector such that antibodies are expressed on the phage. Recombinant anti-GCGR antibodies of the disclosure may be obtained in this way.

Again, by way of example, recombinant human anti-GCGR antibodies of the disclosure can also be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology, 9:1370-1372 (1991); Hay et al., Hum. Antibod. Hybridomas, 3:81-85, 1992; Huse et al., Science, 246:1275-1281, 1989; McCafferty et al., Nature, 348:552-554, 1990; Griffiths et al., EMBO J., 12:725-734, 1993; Hawkins et al., J. Mol. Biol., 226:889-896, 1992; Clackson et al., Nature, 352:624-628, 1991; Gram et al., Proc. Natl. Acad. Sci. (U.S.A.), 89:3576-3580, 1992; Garrad et al., Bio/Technology, 9:1373-1377, 1991; Hoogenboom et al., Nuc. Acid Res., 19:4133-4137, 1991; and Barbas et al., Proc. Natl. Acad. Sci. (U.S.A.), 88:7978-7982, 1991), all incorporated herein by reference.

Human antibodies are also produced by immunizing a non-human, transgenic animal comprising within its genome some or all of human immunoglobulin heavy chain and light chain loci with a human IgE antigen, e.g., a XenoMouse™ animal (Abgenix, Inc./Amgen, Inc.—Fremont, Calif.). XenoMouse™ mice are engineered mouse strains that comprise large fragments of human immunoglobulin heavy chain and light chain loci and are deficient in mouse antibody production. See, e.g., Green et al., Nature Genetics, 7:13-21, 1994 and U.S. Pat. Nos. 5,916,771, 5,939,598, 5,985,615, 5,998,209, 6,075,181, 6,091,001, 6,114,598, 6,130,364, 6,162,963 and 6,150,584. XenoMouse™ mice produce an adult-like human repertoire of fully human antibodies and generate antigen-specific human antibodies. In some embodiments, the XenoMouse™ mice contain approximately 80% of the human antibody V gene repertoire through introduction of megabase sized, germline configuration fragments of the human heavy chain loci and kappa light chain loci in yeast artificial chromosome (YAC). In other embodiments, XenoMouse™ mice further contain approximately all of the human lambda light chain locus. See Mendez et al., Nature Genetics, 15:146-156, 1997; Green and Jakobovits, J. Exp. Med., 188:483-495, 1998; and WO 98/24893.

In various embodiments, the isolated antagonistic antigen binding protein of the present disclosure utilize an antibody or antigen binding antibody fragment thereof is a polyclonal antibody, a monoclonal antibody or antigen-binding fragment thereof, a recombinant antibody, a diabody, a chimerized or chimeric antibody or antigen-binding fragment thereof, a humanized antibody or antigen-binding fragment thereof, a fully human antibody or antigen-binding fragment thereof, a CDR-grafted antibody or antigen-binding fragment thereof, a single chain antibody, an Fv, an Fd, an Fab, an Fab', or an F(ab')$_2$, and synthetic or semi-synthetic antibodies.

In various embodiments, the isolated antagonistic antigen binding protein of the present disclosure utilize an antibody or antigen-binding fragment that binds to an immune-checkpoint protein antigen with a dissociation constant ($K_D$) of, e.g., at least about $1\times10^{-7}$ M, at least about $1\times10^{-8}$ M, at least about $1\times10^{-9}$ M, at least about $1\times10^{-10}$ M, at least about $1\times10^{-11}$ M, or at least about $1\times10^{-12}$ M. In various embodiments, the isolated antagonistic antigen binding protein of the present disclosure utilize an antibody or antigen-binding fragment that binds to an immune-checkpoint protein antigen with a dissociation constant ($K_D$) in the range of, e.g., at least about $1\times10^{-7}$ M to at least about $1\times10^{-8}$ M, at least about $1\times10^{-8}$ M to at least about $1\times10^{-9}$ M, at least about $1\times10^{-9}$ M to at least about $1\times10^{-10}$ M, at least about $1\times10^{-10}$ M to at least about $1\times10^{-11}$ M, or at least about $1\times10^{-11}$ M to at least about $1\times10^{-12}$ M.

Antibodies to the glucagon receptor have been described in, e.g., U.S. Pat. Nos. 5,770,445, 7,947,809, 7,968,686, 8,545,847, 8,771,696 and 9,657,099; European patent application EP2074149A2; EP patent EP0658200B1; U.S. patent publications 2009/0041784; 2009/0252727; 2013/0344538 and 2014/0335091; and PCT publication WO2008/036341. In various embodiments of the present invention, the isolated antagonistic antigen binding protein is an anti-GCGR ("antagonistic") antibody or antigen-binding fragment which comprises the polynucleotide and polypeptide sequences set forth in, e.g., U.S. Pat. Nos. 7,947,809, and 8,158,759, each herein incorporated by reference in its entirety for its specific teaching of polynucleotide and polypeptide sequences of various anti-GCGR antibodies or antigen-binding fragments.

In various embodiments of the present disclosure the antibody may be an anti-GCGR antibody that has the same or higher antigen-binding affinity as that of the antibody comprising the heavy chain variable region sequence as set forth in SEQ ID NO: 2. In various embodiments, the antibody may be an anti-GCGR antibody which binds to the same epitope as the antibody comprising the heavy chain variable region sequence as set forth in SEQ ID NO: 2. In various embodiments, the antibody is an anti-GCGR antibody which competes with the antibody comprising the heavy chain variable region sequence as set forth in SEQ ID NO: 2. In various embodiments, the antibody may be an anti-GCGR antibody which comprises at least one (such as two or three) CDRs of the heavy chain variable region sequence as set forth in SEQ ID NO: 2. In various embodiments, the antibody may be an anti-GCGR antibody which comprises the heavy chain variable region sequence as set forth in SEQ ID NO: 2. In various embodiments, the antibody may be an anti-GCGR antibody which comprises the heavy chain variable region sequence as set forth in SEQ ID NO: 2:

```
                                              (SEQ ID NO: 2)
QVQLVESGGGVVQPGRSLRLSCAASGFTFSSYGMHWVRQAPGKGLEWVAV

MWYDGSNKDYVDSVKGRFTISRDNSKNTLYLQMNRLRAEDTAVYYCAREK

DHYDILTGYN YYYGLDVWGQGTTVTVSS
```

In various embodiments of the present disclosure the antibody may be an anti-GCGR antibody that has the same or higher antigen-binding affinity as that of the antibody comprising the light chain variable region sequence as set forth in SEQ ID NO: 3. In various embodiments, the antibody may be an anti-GCGR antibody which binds to the same epitope as the antibody comprising the light chain variable region sequence as set forth in SEQ ID NO: 3. In various embodiments, the antibody is an anti-GCGR antibody which competes with the antibody comprising the light chain variable region sequence as set forth in SEQ ID NO: 3. In various embodiments, the antibody may be an anti-GCGR antibody which comprises at least one (such as two or three) CDRs of the light chain variable region sequence as set forth in SEQ ID NO: 3. In various embodiments, the antibody may be an anti-GCGR antibody which comprises the light chain variable region sequence as set forth in SEQ ID NO: 3. In various embodiments, the antibody may be an anti-GCGR antibody which comprises the light chain variable region sequence as set forth in SEQ ID NO: 3:

```
                                              (SEQ ID NO: 3)
DIQMTQSPSSLSASVGDRVTITCRASQGIRNDLGWYQQKPGKAPKRLIYA

ASSLQSGVPSRFSGSGSGTEFTLTISSVQPEDFVTYYCLQHNSNPLTFGG

GTKVEIK
```

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 2 or 3.

In various embodiments of the present disclosure the antibody may be an anti-GCGR antibody that has the same or higher antigen-binding affinity as that of the antibody comprising the heavy chain variable region sequence as set forth in SEQ ID NO: 4. In various embodiments, the antibody may be an anti-GCGR antibody which binds to the same epitope as the antibody comprising the heavy chain variable region sequence as set forth in SEQ ID NO: 4. In various embodiments, the antibody is an anti-GCGR antibody which competes with the antibody comprising the heavy chain variable region sequence as set forth in SEQ ID NO: 4. In various embodiments, the antibody may be an anti-GCGR antibody which comprises at least one (such as two or three) CDRs of the heavy chain variable region sequence as set forth in SEQ ID NO: 4. In various embodiments, the antibody may be an anti-GCGR antibody which comprises the heavy chain variable region sequence as set forth in SEQ ID NO: 4. In various embodiments, the antibody may be an anti-GCGR antibody which comprises the heavy chain variable region sequence as set forth in SEQ ID NO: 4:

(SEQ ID NO: 4)
QVQLVESGGGVVQPGRSLRLSCAASGFTFSSYGMHWVRQAPGKGLEWVAV

MWYDGSNKDYVDSVKGRFTISRDNSKNTLYLQMNSLRAEDTAVYYCAREK

DHYDILTGYNYYYGLDVWGQGTTVTVSS

In various embodiments of the present disclosure the antibody may be an anti-GCGR antibody that has the same or higher antigen-binding affinity as that of the antibody comprising the light chain variable region sequence as set forth in SEQ ID NO: 5. In various embodiments, the antibody may be an anti-GCGR antibody which binds to the same epitope as the antibody comprising the light chain variable region sequence as set forth in SEQ ID NO: 5. In various embodiments, the antibody is an anti-GCGR antibody which competes with the antibody comprising the light chain variable region sequence as set forth in SEQ ID NO: 5. In various embodiments, the antibody may be an anti-GCGR antibody which comprises at least one (such as two or three) CDRs of the light chain variable region sequence as set forth in SEQ ID NO: 5. In various embodiments, the antibody may be an anti-GCGR antibody which comprises the light chain variable region sequence as set forth in SEQ ID NO: 5. In various embodiments, the antibody may be an anti-GCGR antibody which comprises the light chain variable region sequence as set forth in SEQ ID NO: 5:

(SEQ ID NO: 5)
DIQMTQSPSSLSASVGDRVTITCRASQGIRNDLGWYQQKPGKAPKRLIYA

ASSLQSGVPSRFSGSGSGTEFTLTISSLQPEDFVTYYCLQHNSNPLTFGG

GTKVEIK

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 4 or 5.

In various embodiments of the present disclosure the antibody may be an anti-GCGR antibody that has the same or higher antigen-binding affinity as that of the antibody comprising the heavy chain variable region sequence as set forth in SEQ ID NO: 6. In various embodiments, the antibody may be an anti-GCGR antibody which binds to the same epitope as the antibody comprising the heavy chain variable region sequence as set forth in SEQ ID NO: 6. In various embodiments, the antibody is an anti-GCGR antibody which competes with the antibody comprising the heavy chain variable region sequence as set forth in SEQ ID NO: 6. In various embodiments, the antibody may be an anti-GCGR antibody which comprises at least one (such as two or three) CDRs of the heavy chain variable region sequence as set forth in SEQ ID NO: 6. In various embodiments, the antibody may be an anti-GCGR antibody which comprises the heavy chain variable region sequence as set forth in SEQ ID NO: 6. In various embodiments, the antibody may be an anti-GCGR antibody which comprises the heavy chain variable region sequence as set forth in SEQ ID NO: 6:

(SEQ ID NO: 6)
QVQLVESGGGVVQPGRSLRLSCAASGFTFSSYGMHWVRQAPGKGLEWVAV

MWYDGSNKDYVDSVKGRFTISRDNSKNTLYLQMNRLRAEDTAVYYCAREK

DHYDILTGYNYYYGLDVWGQGTTVTVSS

In various embodiments of the present disclosure the antibody may be an anti-GCGR antibody that has the same or higher antigen-binding affinity as that of the antibody comprising the light chain variable region sequence as set forth in SEQ ID NO: 7. In various embodiments, the antibody may be an anti-GCGR antibody which binds to the same epitope as the antibody comprising the light chain variable region sequence as set forth in SEQ ID NO: 7. In various embodiments, the antibody is an anti-GCGR antibody which competes with the antibody comprising the light chain variable region sequence as set forth in SEQ ID NO: 7. In various embodiments, the antibody may be an anti-GCGR antibody which comprises at least one (such as two or three) CDRs of the light chain variable region sequence as set forth in SEQ ID NO: 7. In various embodiments, the antibody may be an anti-GCGR antibody which comprises the light chain variable region sequence as set forth in SEQ ID NO: 7. In various embodiments, the antibody may be an anti-GCGR antibody which comprises the light chain variable region sequence as set forth in SEQ ID NO: 7:

(SEQ ID NO: 7)
DIQMTQSPSSLSASVGDRVTITCRASQGIRNDLGWYQQKPGKAPKRLIYA

ASSLESGVPSRFSGSGSGTEFTLTISSVQPEDFVTYYCLQHNSNPLTFGG

GTKVEIK

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 6 or 7.

In various embodiments of the present disclosure the antibody may be an anti-GCGR antibody that has the same or higher antigen-binding affinity as that of the chimeric antibody comprising the heavy chain sequence as set forth in SEQ ID NO: 8. In various embodiments, the antibody may be an anti-GCGR antibody which binds to the same epitope as the antibody comprising the heavy chain sequence as set forth in SEQ ID NO: 8. In various embodiments, the antibody is an anti-GCGR antibody which competes with the antibody comprising the heavy chain sequence as set forth in SEQ ID NO: 8. In various embodiments, the antibody may be an anti-GCGR antibody which comprises at least one (such as two or three) CDRs of the heavy chain sequence as set forth in SEQ ID NO: 8. In various embodiments, the antibody may be an anti-GCGR antibody which comprises the heavy chain sequence as set forth in SEQ ID NO: 8. In various embodiments, the antibody may be an anti-GCGR antibody which comprises the heavy chain sequence as set forth in SEQ ID NO: 8:

(SEQ ID NO: 8)
MEFGLSWVFLVALLRGVQCQVQLVESGGGVVQPGRSLRLSCAASGFTFSS

YGMHWVRQAPGKGLEWVAVMWYDGSNKDYVDSVKGRFTISRDNSKNTLYL

QMNRLRAEDTAVYYCAREKDHYDILTGYNYYYGLDVWGQGTTVTVSSAKT

TPPSVYPLAPGSAAQTNSMVTLGCLVKGYFPEPVTVIWNSGSLSSGVHTF

PAVLQSDLYTLSSSVTVPSSTWPSETVTCNVAHPASSTKVDKKIVPRDCG

CKPCICTVPEVSSVFIFPPKPKDVLTITLTPKVTCVVVDISKDDPEVQFS

WFVDDVEVHTAQTQPREEQFNSTFRSVSELPIMHQDWLNGKEFKCRVNSA

AFPAPIEKTISKTKGRPKAPQVYTIPPPKEQMAKDKVSLTCMITDFFPED

ITVEWQWNGQPAENYKNTQPIMDTDGSYFVYSKLNVQKSNWEAGNTFTCS

VLHEGLHNHHTEKSLSHSPGK

In various embodiments of the present disclosure the antibody may be an anti-GCGR antibody that has the same or higher antigen-binding affinity as that of the chimeric antibody comprising the light chain sequence as set forth in SEQ ID NO: 9. In various embodiments, the antibody may be an anti-GCGR antibody which binds to the same epitope as the antibody comprising the light chain sequence as set forth in SEQ ID NO: 9. In various embodiments, the antibody is an anti-GCGR antibody which competes with the antibody comprising the light chain sequence as set forth in SEQ ID NO: 9. In various embodiments, the antibody may be an anti-GCGR antibody which comprises at least one (such as two or three) CDRs of the light chain sequence as set forth in SEQ ID NO: 9. In various embodiments, the antibody may be an anti-GCGR antibody which comprises the light chain sequence as set forth in SEQ ID NO: 9. In various embodiments, the antibody may be an anti-GCGR antibody which comprises the light chain sequence as set forth in SEQ ID NO: 9:

(SEQ ID NO: 9)
MDMRVPAQLLGLLLLWFPGARCDIQMTQSPSSLSASVGDRVTITCRASQG

IRNDLGWYQQKPGKAPKRLIYAASSLESGVPSRFSGSGSGTEFTLTISSV

QPEDFVTYYCLQHNSNPLTFGGGTKVEIKRADAAPTVSIFPPSSEQLTSG

GASVVCFLNNFYPKDINVKWKIDGSERQNGVLNSWTDQDSKDSTYSMSST

LTLTKDEYERHNSYTCEATHKTSTSPIVKSFNRNEC

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 8 or 9. In various embodiments, the antibody is an chimeric anti-GCGR antibody which comprises the heavy chain sequence set forth in SEQ ID NO: 8 and the light chain sequence set forth in SEQ ID NO: 9 (hereinafter "REMD2.59C").

In various embodiments of the present disclosure the antibody may be an anti-GCGR antibody which comprises a heavy chain variable region sequence selected from SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 and SEQ ID NO: 27, and a light chain variable region sequence selected from SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, and SEQ ID NO: 45. In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 10-27 or SEQ ID NOS: 28-45.

Examples of Anti-GCGR Antibodies

| HCVR | LCVR |
| --- | --- |
| SEQ ID NO: 2 | SEQ ID NO: 3 |
| SEQ ID NO: 4 | SEQ ID NO: 5 |
| SEQ ID NO: 6 | SEQ ID NO: 7 |
| SEQ ID NO: 10 | SEQ ID NO: 28 |
| SEQ ID NO: 11 | SEQ ID NO: 29 |
| SEQ ID NO: 12 | SEQ ID NO: 30 |
| SEQ ID NO: 13 | SEQ ID NO: 31 |
| SEQ ID NO: 14 | SEQ ID NO: 32 |
| SEQ ID NO: 15 | SEQ ID NO: 33 |
| SEQ ID NO: 16 | SEQ ID NO: 34 |
| SEQ ID NO: 17 | SEQ ID NO: 35 |
| SEQ ID NO: 18 | SEQ ID NO: 36 |
| SEQ ID NO: 19 | SEQ ID NO: 37 |
| SEQ ID NO: 20 | SEQ ID NO: 38 |
| SEQ ID NO: 21 | SEQ ID NO: 39 |
| SEQ ID NO: 22 | SEQ ID NO: 40 |
| SEQ ID NO: 23 | SEQ ID NO: 41 |
| SEQ ID NO: 24 | SEQ ID NO: 42 |
| SEQ ID NO: 25 | SEQ ID NO: 43 |
| SEQ ID NO: 26 | SEQ ID NO: 44 |
| SEQ ID NO: 27 | SEQ ID NO: 45 |

An isolated anti-GCGR antibody, antibody fragment, or antibody derivative of the present disclosure can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In various embodiments, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lanitto et al., Methods Mol. Biol. 178:303-16 (2002).

In various embodiments, an isolated antigen binding protein of the present disclosure comprises the constant light chain kappa region as set forth in SEQ ID NO: 46, or a fragment thereof. In various embodiments, an isolated antigen binding protein of the present disclosure comprises the constant light chain lambda region as set forth in SEQ ID NO: 47, or a fragment thereof. In various embodiments, an isolated antigen binding protein of the present disclosure comprises a IgG2 heavy chain constant region set forth in SEQ ID NO: 48, or a fragment thereof.

In various embodiments, an isolated antagonistic antigen binding protein of the present disclosure is an fully anti-GCGR antibody which comprises the heavy chain sequence as set forth in SEQ ID NO: 49 and the light chain as set forth in SEQ ID NO: 50 (hereinafter "REMD-477").

In various embodiments of the present disclosure, the isolated antagonistic antigen binding protein is a hemibody. A "hemibody" is an immunologically-functional immunoglobulin construct comprising a complete heavy chain, a complete light chain and a second heavy chain Fc region paired with the Fc region of the complete heavy chain. A linker can, but need not, be employed to join the heavy chain Fc region and the second heavy chain Fc region. In various embodiments, the hemibody is a monovalent antigen binding protein comprising (i) an intact light chain, and (ii) a heavy chain fused to an Fc region (e.g., an IgG2 Fc region). Methods for preparing hemibodies are described in, e.g., U.S. patent application 2012/0195879, herein incorporated by reference in its entirety herein for purposes of teaching the preparation of such hemibodies.

In various embodiments, the glucagon receptor antagonist or modulator is a small molecule. In various embodiments, the methods comprise the use of glucagon receptor antagonists or modulators, as described in U.S. Pat. Nos. 8,907,103, 8,445,538, 8,361,959, 9,045,389, 8,623,818, 7,138,529, 8,748,624, 8,232,413, 8,470,773, 8,324,384, 8,809,579, 8,318,667, 8,735,604, 789,472, 7,935,713, 7,803,951, 7,687,534, and 8,436,015, U.S. Patent Application Nos. 20140135400, 20110281795, 20130012493, and 20130012434, and PCT Application Nos. WO2010019828, WO2003051357, WO2015066252, WO2003053938, WO2004/069158, WO2005/121097, and WO2007/015999. In various embodiments, the methods comprise the use of a glucagon receptor modulator as described in U.S. Pat. Nos. 8,084,489, 7,816,557, 7,807,702, 8,691,856, 7,863,329, 8,076,374, 7,696,248, 7,989,457, 8,809,342, 8,507,533 and 8,927,577. In various embodiments, the methods comprise the use of a glucagon receptor antagonist selected from LY2409021, MK-0893, GRA1, LGD-6972, PF-06291874 and Bat 27-9955.

In various embodiments, the glucagon receptor antagonist is an anti-GCGR antibody and the PI3K pathway inhibitor is BYL719 (PI3Kα selective). In various embodiments, the glucagon receptor antagonist is an anti-GCGR antibody and the PI3K pathway inhibitor is GSK2636771 (PI3Kβ selective). In various embodiments, the glucagon receptor antagonist is an anti-GCGR antibody and the PI3K pathway inhibitor is a combination of BYL719 and GSK2636771. In various embodiments, the glucagon receptor antagonist is an anti-GCGR antibody and the PI3K pathway inhibitor is NVP-BKM120 (pan-specific). In various embodiments, the glucagon receptor antagonist is an anti-GCGR antibody and the PI3K pathway inhibitor is a pan AKT inhibitor selected from GSK690693 and MK-2206. In various embodiments, the glucagon receptor antagonist is an anti-GCGR antibody and the PI3K pathway inhibitor is RAD001 (mTORC1 inhibitor). In various embodiments, the glucagon receptor antagonist is an anti-GCGR antibody and the PI3K pathway inhibitor is Ganitumab (IGF1R monoclonal antibody). In various embodiments, the glucagon receptor antagonist is an anti-GCGR antibody and the PI3K pathway inhibitor is linsitinib (IGF1R+IR kinase inhibitor). In various embodiments, the glucagon receptor antagonist is an anti-GCGR antibody and the PI3K pathway inhibitor is MEDI 573 (IGF1+IGF2 monoclonal Ab).

Cancer

Cancer is group of diseases involving abnormal cell growth with the potential to spread or invade other parts of the body. Abnormal growths that form a discrete tumor mass, i.e., do not contain cysts or liquid areas, are defined as solid tumors. Solid tumors may be benign (not cancer), or malignant (cancer). Different types of solid tumors are named for the type of cells that form them. Examples of solid tumors are sarcomas, carcinomas, and lymphomas. Cancers derived from either of the two blood cell linages, myeloid and lymphoid, are defined as hematological malignancies. Such malignancies are also referred to as blood cancers or liquid tumors. Examples of liquid tumors include multiple myeloma, acute leukemias (e.g., 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (e.g., chronic myelocytic (granulocytic) leukemia, chronic myelogenous leukemia, and chronic lymphocytic leukemia), polycythemia vera, lymphoma, Hodgkin's lymphoma, non-Hodgkin's lymphoma (indolent and high grade forms), Waldenstrom's macroglobulinemia, heavy chain disease, myelodysplastic syndrome, hairy cell leukemia and myelodysplasia.

In one aspect, the present disclosure provides combination therapy methods of treating a subject having cancer, comprising administering to the subject a) an effective amount of a pharmaceutical composition comprising a phosphatidylinositol 3-kinases (PI3K) inhibitor, and b) an effective amount of a pharmaceutical composition comprising a glucagon receptor antagonist. In various embodiments, cancer is selected from the group consisting of: a) cancers of the breast, which include, but are not limited to, invasive ductal carcinoma, invasive lobular carcinoma, ductal carcinoma, lobular carcinoma in situ and metastatic breast cancer; b) cancers of lymphocytic cells, which include, but are not limited to, various T cell and B cell lymphomas, non-Hodgkins lymphoma, cutaneous T cell lymphoma, Hodgkins disease, and lymphoma of the central nervous system; (c) multiple myeloma, chronic neutrophilic leukemia, chronic eosinophilic leukemia/hypereosinophilic syndrome, chronic idiopathic myelofibrosis, polycythemia vera, essential thrombocythemia, chronic myelomonocytic leukemia, atypical chronic myelogenous leukemia, juvenile myelomonocytic leukemia, refractory anemia with ringed sideroblasts and without ringed sideroblasts, refractory cytopenia (myelodysplastic syndrome) with multilineage dysplasia, refractory anemia (myelodysplastic syndrome) with excess blasts, 5q-syndrome, myelodysplastic syndrome with t(9;12)(q22;p12), and myelogenous leukemia (e.g., Philadelphia chromosome positive (t(9;22)(qq34;q11)); d) cancers of the skin, which include, but are not limited to, basal cell carcinoma, squamous cell carcinoma, malignant melanoma and Kaposi's sarcoma; e) leukemias, which include, but are not limited to, acute myeloid leukemia, acute lymphoblastic leukemia, chronic lymphocytic leukemia, chronic myelogenous leukemia, and hairy cell leukemia, f) cancers of the digestive tract, which include, but are not limited to, anal, colon, colorectal, esophageal, gallbladder, stomach (gastric), pancreatic cancer, pancreatic cancer-Islet cell, rectal, small-intestine and salivary gland cancers; g) cancers of the liver, which include, but are not limited to, hepatocellular carcinoma, cholangiocarcinoma, mixed hepatocellular cholangiocarcinoma, primary liver cancer and metastatic liver cancer; h) cancers of the male reproductive organs, which include, but are not limited to, prostate cancer, testicular cancer and penile cancer; i) cancers of the female reproductive organs, which include, but are not limited to, uterine cancer (endometrial), cervical, ovarian, vaginal, vulval cancers, uterine sarcoma and ovarian germ cell tumor; j) cancers of the respiratory tract, which include, but are not limited to, small cell and non-small cell lung carcinoma, bronchial adema, pleuropulmonary blastoma and malignant mesothelioma; k) cancers of the brain, which include, but are not limited to, brain stem and hyptothalamic glioma, cerebellar and cerebral astrocytoma, medullablastoma, ependymal tumors, oligodendroglial, meningiomas and neuroectodermal and pineal tumors; l) cancers of the eye, which include, but are not limited to, intraocular melanoma, retinoblastoma, and rhabdomyosarcoma; m) cancers of the head and neck, which include, but are not limited to, laryngeal, hypopharyngeal, nasopharyngeal, oropharyngeal cancers, and lip and oral cancer, squamous neck cancer, metastatic paranasal sinus cancer; n) cancers of the thyroid, which include, but are not limited to, thyroid cancer, thymoma, malignant thymoma, medullary thyroid carcinomas, papillary thyroid carcinomas, multiple endocrine neoplasia type 2A (MEN2A), pheochromocytoma, parathyroid adenomas, multiple endocrine neoplasia type 2B (MEN2B), familial medullary thyroid carcinoma (FMTC) and carcinoids; o) cancers of the urinary tract, which include, but are not limited to, bladder cancer; p) sarcomas, which include, but are not limited to, sarcoma of the soft tissue, osteosarcoma, malignant fibrous histiocytoma, lymphosarcoma, and rhabdomyosarcoma; q) cancers of the kidneys, which include, but are not limited to, renal cell carcinoma, clear cell carcinoma of the kidney; and renal cell adenocarcinoma; r) precursor B-lymphoblastic leukemia/lymphoma (precursor B-cell acute lymphoblastic leukemia), B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma and Burkitt's lymphoma/Burkitt cell leukemia; (s) precursor T-lymphoblastic lymphoma/leukemia (precursor T-cell acute lymphoblastic leukemia), T-cell prolymphocytic leukemia, T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, mycosis fungoides/Sezary syndrome, anaplastic large-cell lymphoma, T/null cell, primary cutaneous type, peripheral T-cell lymphoma, not otherwise characterized, angioimmunoblastic T-cell lymphoma, anaplastic large-cell lymphoma, T/null cell, and primary systemic type; (t) nodular lymphocyte-predominant Hodgkin's lymphoma, nodular sclerosis Hodgkin's lymphoma (grades 1 and 2), lymphocyte-rich classical Hodgkin's lymphoma, mixed cellularity Hodgkin's lymphoma, and lymphocyte depletion Hodgkin's lymphoma; and (u) AML with t(8;21)(q22;q22), AML1(CBF-alpha)/ETO, acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11.times.), and AML with 11q23 (MLL) abnormalities, AML minimally differentiated, AML without maturation, AML with maturation, acute myelomonocytic leukemia, acute monocytic leukemia, acute erythroid leukemia, acute megakaryocytic leukemia, acute basophilic leukemia, and acute panmyelosis with myelofibrosis. In various embodiments, the cancer is breast cancer. In various embodiments, the cancer is ovarian cancer.

Pharmaceutical Compositions

In another aspect, the present disclosure provides a pharmaceutical composition comprising an isolated glucagon receptor antagonist as described herein, with one or more pharmaceutically acceptable carrier(s); a pharmaceutical composition comprising a PI3K inhibitor as described herein, with one or more pharmaceutically acceptable carrier(s); or a pharmaceutical composition comprising an isolated glucagon receptor antagonist and a PI3K inhibitor as described herein, with one or more pharmaceutically acceptable carrier(s). The pharmaceutical compositions and methods of uses described herein also encompass embodiments of combinations (co-administration) with other active agents, as detailed below.

The isolated glucagon receptor antagonists and/or PI3K pathway inhibitors provided herein can be formulated by a variety of methods apparent to those of skill in the art of pharmaceutical formulation. Such methods may be found, for example, in Remington's Pharmaceutical Sciences, 19th Edition (Mack Publishing Company, 1995). The pharmaceutical compositions are generally formulated as sterile, substantially isotonic and in full compliance with all GMP regulations of the U.S. Food and Drug Administration.

Generally, isolated glucagon receptor antagonists and/or PI3K pathway inhibitors of the invention are suitable to be administered as a formulation in association with one or more pharmaceutically acceptable excipient(s), or carriers. Such pharmaceutically acceptable excipients and carriers are well known and understood by those of ordinary skill and have been extensively described (see, e.g., Remington's Pharmaceutical Sciences, 18th Edition, A. R. Gennaro, ed., Mack Publishing Company, 1990). The pharmaceutically acceptable carriers may be included for purposes of modifying, maintaining or preserving, for example, the pH, osmolarity, viscosity, clarity, color, isotonicity, odor, sterility, stability, rate of dissolution or release, adsorption or penetration of the composition. Such pharmaceutical compositions may influence the physical state, stability, rate of in vivo release, and rate of in vivo clearance of the polypeptide. Suitable pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute thereof. In one embodiment of the present disclosure, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose. The optimal pharmaceutical composition will be determined by one of ordinary skill in the art depending upon, for example, the intended route of administration, delivery format, and desired dosage.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In various embodiments, the pharmaceutical composition is formulated for parenteral administration via a route selected from, e.g., subcutaneous injection, intraperitoneal injection, intramuscular injection, intrasternal injection, intravenous injection, intraarterial injection, intrathecal injection, intraventricular injection, intraurethral injection, intracranial injection, intrasynovial injection or via infusions.

When parenteral administration is contemplated, the therapeutic pharmaceutical compositions may be in the form of a pyrogen-free, parenterally acceptable aqueous solution comprising the desired isolated glucagon receptor antagonists in a pharmaceutically acceptable vehicle. A particularly suitable vehicle for parenteral injection is sterile distilled water in which a polypeptide is formulated as a sterile, isotonic solution, properly preserved. In various embodiments, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Optionally, the suspension may also contain suitable stabilizers or agents to increase the solubility of the compounds and allow for the preparation of highly concentrated solutions. Injectable formulations may be prepared, packaged, or sold in unit dosage form, such as in ampoules or in multi-dose containers containing a preservative. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The isolated glucagon receptor antagonist and/or PI3K inhibitor of the present disclosure can be administered intranasally or by inhalation, typically in the form of a dry powder (either alone, as a mixture, or as a mixed component particle, for example, mixed with a suitable pharmaceutically acceptable carrier) from a dry powder inhaler, as an aerosol spray from a pressurized container, pump, spray, atomiser (preferably an atomiser using electrohydrodynamics to produce a fine mist), or nebulizer, with or without the use of a suitable propellant, or as nasal drops.

The pressurized container, pump, spray, atomizer, or nebulizer generally contains a solution or suspension of an isolated glucagon receptor antagonist and/or PI3K inhibitor of the disclosure comprising, for example, a suitable agent for dispersing, solubilizing, or extending release of the active, a propellant(s) as solvent.

Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the glucagon receptor antagonist and/or PI3K inhibitor of the disclosure, a suitable powder base and a performance modifier.

Suitable flavours, such as menthol and levomenthol, or sweeteners, such as saccharin or saccharin sodium, may be added to those formulations of the disclosure intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the disclosure are typically arranged to administer a metered dose or "puff" of an antibody of the disclosure. The overall daily dose will typically be administered in a single dose or, more usually, as divided doses throughout the day.

The isolated glucagon receptor antagonist and/or PI3K inhibitor of the present disclosure may also be formulated for an oral administration. Oral administration may involve swallowing, so that the compound enters the gastrointestinal tract, and/or buccal, lingual, or sublingual administration by which the compound enters the blood stream directly from the mouth. Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Pharmaceutical compositions intended for oral use may be prepared according to any method known to the art for the manufacture of pharmaceutical compositions and such compositions may contain one or more agents selected from the group consisting of sweetening agents in order to provide a pharmaceutically elegant and palatable preparation. For example, to prepare orally deliverable tablets, the isolated glucagon receptor antagonist and/or PI3K inhibitor is mixed with at least one pharmaceutical carrier, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical carrier, and the solid formulation is placed in a capsular container suitable for delivery to the gastrointestinal tract. Compositions comprising isolated glucagon receptor antagonists and/or PI3K pathway inhibitors may be prepared as described generally in Remington's Pharmaceutical Sciences, 18th Ed. 1990 (Mack Publishing Co. Easton Pa. 18042) at Chapter 89, which is herein incorporated by reference.

In various embodiments, the pharmaceutical compositions are formulated as orally deliverable tablets containing isolated glucagon receptor antagonist and/or PI3K inhibitor in admixture with non-toxic pharmaceutically acceptable carriers which are suitable for manufacture of tablets. These carriers may be inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid, or talc. The tablets may be uncoated or they may be coated with known techniques to delay disintegration and absorption in the gastrointestinal track and thereby provide a sustained action over a longer period of time. For example, a time delay material such as glyceryl monostearate or glyceryl distearate alone or with a wax may be employed.

In various embodiments, the pharmaceutical compositions are formulated as hard gelatin capsules wherein the isolated glucagon receptor antagonist and/or PI3K inhibitor is mixed with an inert solid diluent, for example, calcium carbonate, calcium phosphate, or kaolin or as soft gelatin capsules wherein the isolated glucagon receptor antagonist and/or PI3K inhibitor is mixed with an aqueous or an oil medium, for example, *arachis* oil, peanut oil, liquid paraffin or olive oil.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Any method for formulating and administering peptides, proteins, antibodies, and immunoconjugates accepted in the art may suitably be employed for administering the isolated glucagon receptor antagonists of the present invention. In various embodiments, the REMD-477 of the present invention is produced by a certified GMP manufacturer, CMC Biologics, Seattle, USA, and supplied as a sterile, clear, colorless to slightly yellow frozen liquid Drug Product (DP) for subcutaneous administration. Each sterile vial is filled with 1 mL deliverable volume of 70 mg/mL REMD-477 formulated with 10 mM sodium acetate, 5% (w/v) sorbitol, 0.004% (w/v) polysorbate 20, pH 5.2.

Methods of Treatment

In one aspect, the present disclosure is directed to combination therapy methods of treating a subject having cancer, comprising administering to the subject a) an effective amount of a pharmaceutical composition comprising a phosphatidylinositol 3-kinase (PI3K) inhibitor, and b) an effective amount of a pharmaceutical composition comprising a glucagon receptor antagonist. In various embodiments, the combination therapy methods comprise administering an effective amount of a pharmaceutical composition comprising a PI3K inhibitor, or a pharmaceutically acceptable salt thereof, and a glucagon receptor antagonist antibody. These various combination therapies may provide a "synergistic effect", i.e., the effect achieved when the active ingredients used together is greater than the sum of the effects that results from using the compounds separately. These combination therapy methods are particularly effective against a cancer that is resistant or refractory to treatment using the PI3K inhibitor alone, another anti-cancer agent alone, or the PI3K inhibitor in combination with another anti-cancer agent.

The pharmaceutical compositions of the present disclosure can be tested in clinical studies. Suitable clinical studies can be, for example, open label, dose escalation studies in patients with cancer. Such studies prove in particular the synergism of the active ingredients of the combination of the invention. The beneficial effects on cancer can be determined directly through the results of these studies which are known as such to a person skilled in the art. Such studies can be, in particular, suitable to compare the effects of a monotherapy using the active ingredients and a combination of the invention. In various embodiments, the dose of a PI3K inhibitor is escalated until the Maximum Tolerated Dosage is reached and a glucagon receptor antagonist antibody is administered with a fixed dose. In various embodiments, a PI3K inhibitor is administered in a fixed dose and the dose of a glucagon receptor antagonist antibody is escalated. Each patient can receive doses of the compounds either daily or intermittently. The efficacy of the treatment can be determined in such studies, e.g., after 12, 18 or 24 weeks of treatment, by evaluation of symptom scores every 4 to 6 weeks. It is envisioned that the administration of a combination therapy of the present disclosure will result not only in a beneficial effect, e.g. a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically active ingredients used in the combination of the invention. A further benefit can be that lower and/or less frequent doses of one or both of the active ingredients of the combination of the invention can be used, which can diminish the incidence or severity of side-effects. This is in accordance with the desires and requirements of the patients to be treated.

In various embodiments, a pharmaceutical combination of PI3K inhibitor and glucagon receptor antagonist antibody will be evaluated for its therapeutic effectiveness at treating or preventing cancer, e.g., a PIK3CA amplified, and/or PIK3CA mutated cancer.

Dosage amounts and dosing regimens for the pharmaceutical compositions can be adjusted to provide the optimum desired response (e.g., a therapeutic response). For example, a single bolus can be administered, or several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian patients to be treated; each unit containing a predetermined quantity of active compound calculated to produce the desired therapeutic effect in association with the required pharmaceutical carrier. The specification for the dosage unit forms of the present invention will be dictated primarily by the unique characteristics of the glucagon receptor antagonist and PI3K pathway inhibitor and the particular therapeutic effect to be achieved.

Thus, the skilled artisan would appreciate, based upon the invention provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while various dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the patient need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of the isolated glucagon receptor antagonist antibody of the present disclosure can be in the range of 0.5-1200 mg per subject, 0.5-1100 mg per subject, 0.5-1000 mg per subject, 0.5-900 mg per subject, 0.5-800 mg per subject, 0.5-700 mg per subject, 0.5-600 mg per subject, 0.5-500 mg per subject, 0.5-400 mg per subject, 0.5-300 mg per subject, 0.5-200 mg per subject, 0.5-100 mg per subject, 0.5-50 mg per subject, 1-1200 mg per subject, 1-1100 mg per subject, 1-1000 mg per subject, 1-900 mg per subject, 1-800 mg per subject, 1-700 mg per subject, 1-600 mg per subject, 1-500 mg per subject, 1-400 mg per subject, 1-300 mg per subject, 1-200 mg per subject, 1-100 mg per subject, or 1-50 mg per subject depending, of course, on the mode of administration. For example, an intravenous monthly dose can require about 1-1000 mg/subject. In certain embodiments, the isolated glucagon receptor antagonist antibody of the disclosure can be administered at about 1-200 mg per subject, 1-150 mg per subject or 1-100 mg per subject. The total monthly dose can be administered in single or divided doses and can, at the physician's discretion, fall outside of the typical ranges given herein.

An exemplary, non-limiting weekly dosing range for a therapeutically or prophylactically effective amount of an isolated glucagon receptor antagonist antibody or antigen-binding fragment of the disclosure can be about 0.001 to 10 mg/kg, 0.001 to 9 mg/kg, 0.001 to 8 mg/kg, 0.001 to 7 mg/kg, 0.001 to 6 mg/kg, 0.001 to 5 mg/kg, 0.001 to 4 mg/kg, 0.001 to 3 mg/kg, 0.001 to 20 mg/kg, 0.001 to 1 mg/kg, 0.010 to 10 mg/kg, 0.010 to 9 mg/kg, 0.010 to 8 mg/kg, 0.010 to 7 mg/kg, 0.010 to 6 mg/kg, 0.010 to 5 mg/kg, 0.010 to 4 mg/kg, 0.010 to 3 mg/kg, 0.010 to 2 mg/kg, 0.010 to 1 mg/kg, 0.1 to 10 mg/kg, 0.1 to 9 mg/kg, 0.1 to 8 mg/kg, 0.1 to 7 mg/kg, 0.1 to 6 mg/kg, 0.1 to 5 mg/kg, 0.1 to 4 mg/kg, 0.1 to 3 mg/kg, 0.1 to 2 mg/kg, 0.1 to 1 mg/kg, 0.5 to 10 mg/kg, 0.5 to 9 mg/kg, 0.5 to 8 mg/kg, 0.5 to 7 mg/kg, 0.5 to 6 mg/kg, 0.5 to 5 mg/kg, 0.5 to 4 mg/kg, 0.5 to 3 mg/kg, 0.5 to 2 mg/kg, 0.5 to 1 mg/kg, 1 to 10 mg/kg, 1 to 9 mg/kg, 1 to 8 mg/kg, 1 to 7 mg/kg, 1 to 6 mg/kg, 1 to 5 mg/kg, 1 to 4 mg/kg, 1 to 3 mg/kg, and 1 to 2 mg/kg body weight per week.

In various embodiments, the total dose of glucagon receptor antagonist antibody administered will achieve a plasma antibody concentration in the range of, e.g., about 1 to 1000 µg/ml, about 1 to 750 µg/ml, about 1 to 500 µg/ml, about 1 to 250 µg/ml, about 10 to 1000 µg/ml, about 10 to 750 µg/ml, about 10 to 500 µg/ml, about 10 to 250 µg/ml, about 20 to 1000 µg/ml, about 20 to 750 µg/ml, about 20 to 500 µg/ml, about 20 to 250 µg/ml, about 30 to 1000 µg/ml, about 30 to 750 µg/ml, about 30 to 500 µg/ml, about 30 to 250 µg/ml.

An exemplary, non-limiting dosing range for a therapeutically or prophylactically effective amount of a PI3K pathway inhibitor of the disclosure can be about 0.05 mg/kg to 75 mg/kg, 0.05 mg/kg to 70 mg/kg, 0.05 mg/kg to 60 mg/kg, 0.05 mg/kg to 50 mg/kg, 0.05 mg/kg to 40 mg/kg, 0.05 mg/kg to 30 mg/kg, 0.05 mg/kg to 20 mg/kg, 0.05 mg/kg to 10 mg/kg, 0.1 mg/kg to 75 mg/kg, 0.1 mg/kg to 30 mg/kg, 0.1 mg/kg to 40 mg/kg, 0.1 mg/kg to 50 mg/kg, 0.1 mg/kg to 40 mg/kg, 0.1 mg/kg to 30 mg/kg, 0.1 mg/kg to 20 mg/kg, 0.1 mg/kg to 10 mg/kg, 0.5 mg/kg to 75 mg/kg, 0.5 mg/kg to 70 mg/kg, 0.5 mg/kg to 60 mg/kg, 0.5 mg/kg to 50 mg/kg, 0.5 mg/kg to 40 mg/kg, 0.5 mg/kg to 30 mg/kg, 0.5 mg/kg to 20 mg/kg, 0.5 mg/kg to 10 mg/kg, 1 mg/kg to 75 mg/kg, 1 mg/kg to 70 mg/kg, 1 mg/kg to 60 mg/kg, 1 mg/kg to 50 mg/kg, 1 mg/kg to 40 mg/kg, 1 mg/kg to 30 mg/kg, 1 mg/kg to 20 mg/kg, 1 mg/kg to 10 mg/kg, 5 mg/kg to 75 mg/kg, 5 mg/kg to 70 mg/kg, 5 mg/kg to 60 mg/kg, 5 mg/kg to 50 mg/kg, 5 mg/kg to 40 mg/kg, 5 mg/kg to 30 mg/kg, 5 mg/kg to 20 mg/kg, and 5 mg/kg to 10 mg/kg body weight of the recipient per day. In various embodiments, the dosing range will be from about 0.1-25 mg/kg/day. In various embodiments, the dosing range will be from about 0.5 to 10 mg/kg/day. In various embodiments, the dosing range for administration to a 70 kg person will be from about 35-700 mg per day.

In various embodiments, the pharmaceutical compositions of the present disclosure will comprise a ratio of PI3K pathway inhibitor:GCGR antagonist antibody in the range of 1:100 to 1:1. In various embodiments, the ratio of PI3K inhibitor:GCGR antagonist antibody will be selected from the group consisting of: 1:100, 1:90, 1:80, 1:70, 1:60, 1:50, 1:40, 1:30, 1:20, 1:10, 1:5, 1:2, and 1:1. In various embodiments, the pharmaceutical compositions of the present disclosure will comprise a ratio of GCGR antagonist antibody:PI3K pathway inhibitor in the range of 1:100 to 1:1. In various embodiments, the ratio of GCGR antagonist antibody:PI3K inhibitor will be selected from the group consisting of: 1:100, 1:90, 1:80, 1:70, 1:60, 1:50, 1:40, 1:30, 1:20, 1:10, 1:5, 1:2, and 1:1.

In various embodiments, single or multiple administrations of the pharmaceutical compositions are administered depending on the dosage and frequency as required and tolerated by the patient. The dosage can be administered once but may be applied periodically until either a therapeutic result is achieved or until side effects warrant discontinuation of therapy.

In various embodiments, the combination therapy comprises administering the isolated glucagon receptor antagonist composition and the PI3K pathway inhibitor composition simultaneously, either in the same pharmaceutical composition or in separate pharmaceutical compositions. In various embodiments, isolated glucagon receptor antagonist composition and the PI3K pathway inhibitor composition are administered sequentially, i.e., the isolated glucagon receptor antagonist composition is administered either prior to or after the administration of the PI3K pathway inhibitor composition.

In various embodiments, the administrations of the isolated glucagon receptor antagonist composition and the PI3K pathway inhibitor composition are concurrent, i.e., the administration period of the isolated glucagon receptor antagonist composition and the PI3K pathway inhibitor composition overlap with each other.

In various embodiments, the administrations of the isolated glucagon receptor antagonist composition and the PI3K pathway inhibitor composition are non-concurrent. For example, in various embodiments, the administration of the isolated glucagon receptor antagonist composition is terminated before the PI3K pathway inhibitor composition is administered. In various embodiments, the administration PI3K pathway inhibitor composition is terminated before the isolated glucagon receptor antagonist composition is administered.

Toxicity and therapeutic index of the pharmaceutical compositions of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

Suitable pharmaceutical agents that may be used as a third agent in the methods of the present invention include anti-obesity agents (including appetite suppressants) and glucose-lowering agents, e.g., anti-diabetic agents, anti-hyperglycemic agents, lipid lowering agents, and anti-hypertensive agents.

Suitable anti-obesity agents (some of which may also act as anti-diabetic agents as well) include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, β₃ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists such as velneperit), $PYY_{3-36}$ (including analogs thereof), BRS3 modulator, mixed antagonists of opiod receptor subtypes, thyromimetic agents, dehydroepiandrosterone or an analog thereof, glucocorticoid agonists or antagonists, orexin antagonists, glucagon-like peptide-1 agonists, ciliary neurotrophic factors (such as AXOKINE™ available from Regeneron Pharmaceuticals, Inc., Tarrytown, N.Y. and Procter & Gamble Company, Cincinnati, Ohio), human agouti-related protein (AGRP) inhibitors, histamine 3 antagonists or inverse agonists, neuromedin U agonists, MTP/ApoB inhibitors (e.g., gut-selective MTP inhibitors, such as dirlotapide, JTT130, Usistapide, SLx4090), opioid antagonist, mu opioid receptor modulators, including but not limited to GSK1521498, MetAp2 inhibitors, including but not limited to ZGN-433, agents with mixed modulatory activity at 2 or more of glucagon, GIP and GLP1 receptors, such as MAR-701 or ZP2929, norepinephrine transporter inhibitors, cannabinoid-1-receptor antagonist/inverse agonists, ghrelin agonists/antagonists, oxyntomodulin and analogs, monoamine uptake inhibitors, such as but not limited to tesofensine, an orexin antagonist, combination agents (such as bupropion plus zonisamide, pramlintide plus metreleptin, bupropion plus naltrexone, phentermine plus topiramate), and the like.

In various embodiments, the anti-obesity agent is selected from gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide (described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (SYMLIN™), tesofensine (NS2330), leptin, bromocriptine, orlistat, AOD-9604 (CAS No. 221231-10-3) and sibutramine.

Suitable glucose-lowering agents include anti-diabetic agents, anti-hyperglycemic agents, lipid lowering agents, and anti-hypertensive agents. In various embodiments, the glucose-lowering agent is selected from biguanides, sulfonylureas, meglitinides, thiazolidinediones (TZDs), α-glucosidase inhibitors, DPP-4 inhibitors, bile acid sequestrants, dopamine-2 agonists, SGLT2 inhibitors, GLP-1R agonists, GLP-1 agonists (e.g., exenatide (tradename Byetta®, Amylin/Astrazeneca); liraglutide (tradename Victoza®, Novo Nordisk A/S); lixisenatide (tradename Lyxumia®, Sanofi); albiglutide (tradename Tanzeum®, GlaxoSmithKline); dulaglutide (tradename Trulicity®, Eli Lilly)), amylin mimetics, and insulins.

In various embodiments, the methods described herein may be used in combination with other conventional anti-cancer therapeutic approaches directed to treatment or prevention of proliferative disorders, such approaches including, but not limited to immunotherapy, chemotherapy, small molecule kinase inhibitor targeted therapy, surgery, radiation therapy, and stem cell transplantation. For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of the combination methods described herein.

A wide array of conventional compounds has been shown to have anti-neoplastic activities. These compounds have been used as pharmaceutical agents in chemotherapy to shrink solid tumors, prevent metastases and further growth, or decrease the number of malignant T-cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When the glucagon receptor antagonist+PI3K pathway inhibitor compositions disclosed herein are administered in combination with another conventional anti-neoplastic agent, either concomitantly or sequentially, the glucagon receptor antagonist+PI3K pathway inhibitor compositions may enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant T-cells. In various embodiments, a second anti-cancer agent, such as a chemotherapeutic agent, will be administered to the patient. The list of exemplary chemotherapeutic agent includes, but is not limited to, daunorubicin, dactinomycin, doxorubicin, bleomycin, mitomycin, nitrogen mustard, chlorambucil, melphalan, cyclophosphamide, 6-mercaptopurine, 6-thioguanine, bendamustine, cytarabine (CA), 5-fluorouracil (5-FU), floxuridine (5-FUdR), methotrexate (MTX), colchicine, vincristine, vinblastine, etoposide, teniposide, cisplatin, carboplatin, oxaliplatin, pentostatin, cladribine, cytarabine, gemcitabine, pralatrexate, mitoxantrone, diethylstilbestrol (DES), fluradabine, ifosfamide, hydroxyureataxanes (such as paclitaxel and doxetaxel) and/or anthracycline antibiotics, as well as combinations of agents such as, but not limited to, DA-EPOCH, CHOP, CVP or FOLFOX. In various embodiments, the dosages of such chemotherapeutic agents include, but is not limited to, about any of 10 mg/m$^2$, 20 mg/m$^2$, 30 mg/m$^2$, 40 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 150 mg/m$^2$, 175 mg/m$^2$, 200 mg/m$^2$, 210 mg/m$^2$, 220 mg/m$^2$, 230 mg/m$^2$, 240 mg/m$^2$, 250 mg/m$^2$, 260 mg/m$^2$, and 300 mg/m$^2$.

In various embodiments, the combination therapy methods of the present disclosure may further comprise administering to the subject a therapeutically effective amount of immunotherapy, including, but not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints) such as CTLA-4, PD-1, OX-40, CD137, GITR, LAGS, TIM-3, and VISTA; treatment using bispecific T cell engaging antibodies (BiTE®) such as blinatumomab: treatment involving administration of biological response modifiers such as IL-2, IL-12, IL-15, IL-21, GM-CSF, IFN-α, IFN-β and IFN-γ; treatment using therapeutic vaccines such as sipuleucel-T; treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic); treatment using TALL-104 cells; and treatment using immunostimulatory agents such as Toll-like receptor (TLR) agonists CpG and imiquimod; wherein the combination therapy provides increased effector cell killing of tumor cells, i.e., a synergy exists between the glucagon receptor antagonist, the PI3K inhibitor, and the immunotherapy when co-administered.

The invention having been described, the following examples are offered by way of illustration, and not limitation.

Example 1

Studies were performed to determine whether pre-treatment using a glucagon receptor antagonist antibody would reduce the PI3K/AKT pathway inhibitor-induced hyperglycemia in normal C57BL/6 mice. The immunocompetent C57BL/6 mouse strain, commonly used for T1 DM and T2DM pharmacological studies including the preclinical validation of GCGR antagonistic monoclonal antibodies (Yan et al., J Pharmacol Exp Ther, 329(1):102-111, 2009), was used in the study.

In this example, the combination therapy comprised pre-treatment with a chimeric anti-GCGR antibody which comprises the heavy chain sequence set forth in SEQ ID NO: 8 and the light chain sequence set forth in SEQ ID NO: 9 ("REMD2.59C") and administration with the PI3K pathway inhibitors listed in Table 2 (obtained from Shanghai Biochempartner ShangHai, China).

TABLE 2

PI3K/Akt Pathway Inhibitors and Formulation

| Drug | Target Selectivity (IC50) | Reference |
| --- | --- | --- |
| BYL719 (alpelisib) | 4.6 nM (PI3Kα), 1156 nM (PI3Kβ), 290 nM (PI3Kδ), 250 nM (pPI3Kγ), 9100 nM (VPS34), 581 nM (PI4Kβ), 9100 nM (mTOR), 9100 nM (DNAPK), 15000 nM (ATR) | Furet et al., Bioorganic & Medicinal Chemistry Letters, 23: 3741-48, 2013; Blake et al., J Med Chem, 55(18): 8110-27, 2012 |
| BKM120 (buparlisib) | 582 nM, (CSF1R), 52 nM (PI3Kα), 166 nM (PI3Kβ), 116 nM, (PI3Kδ), 262 nM (PI3Kγ), 2140 nM (VPS34), 2866 nM (mTOR), 8091 nM (ATR) | Koul et al., American Association for Cancer Research, 18(1): 184-95, 2012 |
| GDC-0980 (apitolisib) | 697 nM (FGR), 232 nM (MLK1), 134 nM (SYK), 5 nM (PI3Kα), 27 nM (PI3Kβ), 7 nM (PI3Kδ), 14 nM (PI3Kγ), 2000 nM (VPS34), 17 nM (mTOR), 623 nM DNAPK | Wallin et al., American Association for Cancer Research, 10(12): 2426-2436, 2011 |

TABLE 2-continued

PI3K/Akt Pathway Inhibitors and Formulation

| Drug | Target Selectivity (IC50) | Reference |
|---|---|---|
| MK2206 Allosteric Inhibitor | 8 nM (AKT1), 12 nM (AKT2), 65 nM (AKT3) | Yap et al., J Clin Oncol., 29(35): 4688-95, 2011 |
| GSK690693 | 2 nM (AKT1), 13 nM (AKT2), 9 nM (AKT3), 50 nM (AMPK), 81 nM (DAPK2), 10 nM (PAK4), 52 nM (PAK5), 6 nM (PAK6), 24 nM (PKA), 2 nM (PKCv), 2 nM (PKCθ), 19 nM (PKCβ1), 14 nM(PKCδ), 21 nM (PKCε), 5 nM (PRKX), 33 nM (PKG1β) | Rhodes et al., Cancer Research, 68(7): 2366-2374, 2008 |
| GDC-0068 (ipatasertib) | 5 nM (AKT1), 18 (AKT2), 8 nM (AKT3), 3100 nM (PKA), 862 nM (p70S6K), 98 nM (PRG1α), 69 nM (PRKG1β) | Blake et al., J Med Chem, 55(18): 8110-27, 2012 |
| OSI-906 (linsitinib) | 75 nM (INSR). 35 nM (IGF1R), 75 nM IRR | Mulvihill et al., Future Med Chem, 1(6): 1153-71, 2009 |

All the procedures related to animal handling, care, and the treatment in this study were performed according to guidelines approved by the Institutional Animal Care and Use Committee (IACUC) of Pharmaron following the guidance of the Association for Assessment and Accreditation of Laboratory Animal Care (AAALAC). C57BL/6 mice (Vital River Laboratory Animal Technology Co., LTD) (male, age 8-10 weeks) were quarantined for 7 days before the study. The general health of the animals was evaluated by a veterinarian, and complete health checks were performed. Animals with abnormalities were excluded prior the study. Animals had free access to irradiation sterilized dry granule food during the entire study period except for time periods specified by the protocol.

The test articles were formulated for administration as follows: REMD 2.59c (A10 mM Na Acetate PH 5.2, 5% sorbitol, 0.004% T-20); BYL719 (10% NMP (ALFA AESAR)/30% PEG300 (ALDRICH)/20% HS15 (SIGMA)/40% water); (BKM120 (10% NMP (ALFA AESAR)/90% PEG300 (ALDRICH)); MK-2206 (30% Captisol (CYDEX).

The experimental protocol to determine the effect of REMD2.59c on the induction of hyperglycemia by PI3K/Akt pathway inhibitors is illustrated in FIG. 1. Based on body weight, mice were randomly assigned to respective treatment groups listed in Table 3 using a computer-generated randomization procedure. On Day 1 (−24 h), the mice were administered either a single dose of REMD2.59C antibody (7.0 mg/kg, i.p.), or antibody vehicle alone (ASN).

One Day 2 (0 h), the REMD2.59c and ASN treated mice (n=3 each) mice received a single dose (p.o.) of BYL719 (50 mg/kg), BKM120 (50 mg/kg), MK2206 (150 mg/kg) as indicated in Table 3. The fed blood glucose levels of mice were measured via tail veins by using Accu-Chek Performa System (Roche Diagnostics) at time −0.5 h before dosing, and 2 h and 4 h after dosing. The dose of REMD2.59c selected is saturating based on previous observations (Yan et al., J Pharmacol Exp Ther, 329(1):102-111, 2009). The BYL-719, BKM120 and MK2206 doses were generally greater than 50% of the maximum reported in preclinical studies.

Statistical analysis of glucose levels in response to PI3K/Akt pathway inhibition in REMD2.59c treated or untreated mice was performed Graph Pad Prism 5.0. software. The group mean, standard deviation were calculated and unpaired t-test comparisons test were applied with a level of significance was set at 5% or $P<0.05$.

Figure 2:
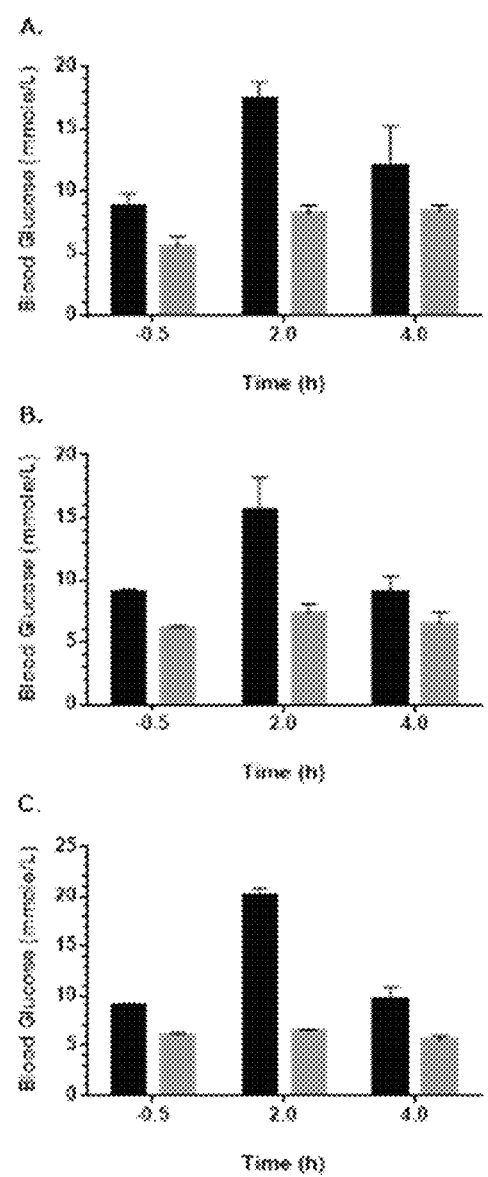
FIG. 2A is a histogram depicting blood glucose levels at −0.5 hour pre-dosing, 2 hours post-dosing and 4 hours post-dosing in mice dosed with 50 mg/kg BYL719 and pretreated with REMD2.59c or ASN vehicle for 24 hours.
FIG. 2B is a histogram depicting blood glucose levels at −0.5 hour pre-dosing, 2 hours post-dosing and 4 hours post-dosing in mice dosed with 50 mg/kg BKM120 and pretreated with REMD2.59c or ASN vehicle for 24 hours.
FIG. 2C is a histogram depicting blood glucose levels at −0.5 hour pre-dosing, 2 hours post-dosing and 4 hours post-dosing in mice dosed with 150 mg/kg MK2206 and pretreated with REMD2.59c or ASN vehicle for 24 hours. The black bars represent ASN treated mice. The gray bars represent mice pretreated with REMD2.59c.

The mean/sd of baseline and treatment glucose levels obtained in the survey of PI3K/Akt pathway inhibitors, with and without, REMD2.59c pretreatment are listed in Table 3 for each time point. The data were plotted as histograms in FIG. 2A. (BYL719), FIG. 2B (BKM120), and FIG. 2C (MK2206) in which the black bars represent ASN pretreated mice, and the gray bars represent REMD2.59c pretreated mice. As depicted in FIGS. 2A-2C, pretreatment with REMD 2.59c statistically significantly reduced baseline circulating glucose by 33 percent.

TABLE 3

Effects of PI3K/AKT pathway inhibition and REMD2.59c pretreatment in C57BL/6 mice

| −24 h Drug Treatment | 0 h Drug Treatment | −0.5 h Glucose (mM) | 2 h Glucose (mM) | 4 h Glucose mM |
|---|---|---|---|---|
| ASN (i.p.) | None | 8.8 ± 1.0, 9.1 ± 0.2 | — | — |
| ASN (i.p.) | BYL719 (50 mg/kg; p.o.) | — | 17.4 ± 1.4 | 11.9 ± 3.3 |
| ASN (i.p.) | BKM120 (50 mg/kg; p.o.) | — | 15.7 ± 2.5 | 9.1 ± 1.3 |
| ASN (i.p.) | GDC-0980 (10 mg/kg; p.o.) | — | 27.0 ± 1.8 | 20.5 ± 0.9 |
| ASN (i.p.) | MK2206 (150 mg/kg; p.o.) | — | 20.1 ± 0.8 | 9.6 ± 1.3 |
| ASN (i.p.) | GSK690693 (30 mg/kg; p.o.) | — | 27.1 ± 2.6 | 21.2 ± 1.5 |
| ASN (i.p.) | GDC-0068 (10 mg/kg; p.o.) | — | 28.4 ± 2.0 | 25.9 ± 1.2 |
| ASN (i.p.) | OSI-906 (100 mg/kg; p.o.) | — | 29.3 ± 1.7 | 23.4 ± 1.5 |
| REMD2.59c (7 mg/kg; i.p.) | None | 5.6 ± 0.8, 6.1 ± 0.2 | — | — |

TABLE 3-continued

Effects of PI3K/AKT pathway inhibition and REMD2.59c pretreatment in C57BL/6 mice

| −24 h Drug Treatment | 0 h Drug Treatment | −0.5 h Glucose (mM) | 2 h Glucose (mM) | 4 h Glucose mM |
|---|---|---|---|---|
| REMD2.59c (7 mg/kg; i.p.) | BYL719 (50 mg/kg; p.o.) | — | 8.2 ± 0.7** | 8.4 ± 0.5 |
| REMD2.59c (7 mg/kg; i.p.) | BKM120 (50 mg/kg; p.o.) | — | 7.4 ± 0.7** | 6.5 ± 0.9* |
| REMD2.59c (7 mg/kg; i.p.) | GDC-0980 (10 mg/kg; p.o.) | — | 21.3 ± 0.7** | 17.9 ± 1.2* |
| REMD2.59c (7 mg/kg; i.p.) | MK2206 (150 mg/kg; p.o.) | — | 6.5 ± 0.1** | 5.6 ± 0.4** |
| REMD2.59c (7 mg/kg; i.p.) | GSK690693 (30 mg/kg; p.o.) | — | 18.9 ± 1.6** | 19.5 ± 1.8 |
| REMD2.59c (7 mg/kg; i.p.) | GDC-0068 (100 mg/kg; p.o.) | — | 22.7 ± 2.7* | 24.5 ± 1.7 |
| REMD2.59c (7 mg/kg; i.p.) | OSI-906 (100 mg/kg; p.o.) | — | 21.5 ± 1.8** | 26.5 ± 1.1 |

Note:
*$p < 0.05$, **$p < 0.01$ compared with vehicle plus compound X respectively.
The BYL719 ASN control and treatment results were obtained in an experiment performed on a different day Hyperglycemia in the range of severe diabetes (~2-fold elevated relative to −0.5 h before dosing) was consistently observed at 2 h after administration of BYL719, BKM120 and MK-2206 pretreated with ASN antibody vehicle alone. The induction of hyperglycemia at 2 h by BYL719, BKM120 and MK-2206 was completely prevented in animals that received REMD2.59c before drug administration; glucose values were maintained below the baseline of untreated ASN control mice. The decline in glucose levels at 4 h in mice that were not pretreated with REMD 2.59c is attributed to loss of target coverage due to elimination of PI3K/AKT from circulation.

The results obtained in Example 1 are consistent with a large body of published evidence showing that activation of PI3K/AKT signaling through the insulin receptor in the liver controls glucose homeostasis in feeding mice and other animals. The observation that glucagon receptor inhibition can effectively maintain normal blood glucose levels in animals treated with certain PI3K and AKT inhibitors (BLY719, BKM120, MK2206) has not been previously reported.

Example 2

The experiment described in Example 1 was also performed with PI3K/AKT pathway inhibitors that differed for BLY719, BKM120 and AKT with respect to target selectivity and other properties. These additional inhibitors included GDC-0980, GSK690693, GDC-0068, and OSI-906 (Table 2). These test articles were formulated for as follows: GDC-0980 (0.5% methylcellulose (SIGMA), 0.2% Tween-80 (SOLARBIO); GSK6900693 (5% mannitol (SIGMA); GDC-0068 (0.5% methylcellulose (SIGMA), 0.2% Tween-80 (SOLARBIO); OSI-906 (25 mM tartaric acid (Tianjing Guangfu Technology Development Ltd.). The REMD2.59c and ASN treated mice (n=3) mice received a single, saturating or near saturating, dose (p.o.) of GDC-0980 (10 mg/kg), GSK6900693 (30 mg/kg), GDC-0068 (10 mg/kg) or OSI-906 (100 mg/kg) as indicated in Table 3.

Figure 3:
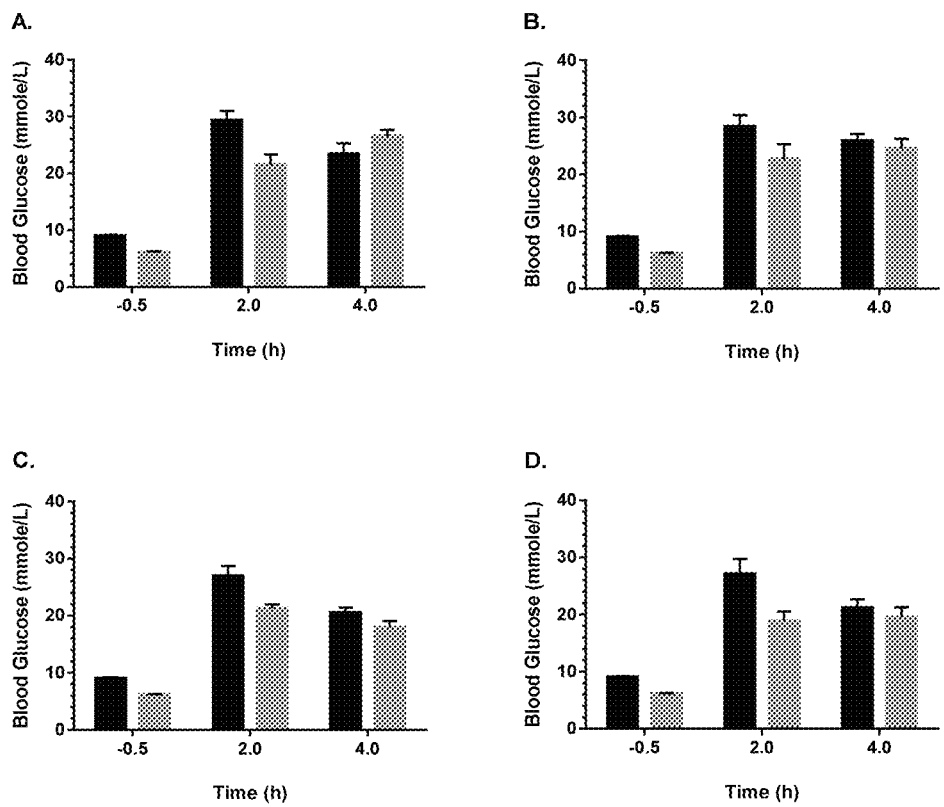
FIG. 3A is a histogram depicting blood glucose levels at −0.5 hour pre-dosing, 2 hours post-dosing and 4 hours post-dosing in mice dosed with 100 mg/kg OSI-906 and pretreated with REMD2.59c or ASN vehicle for 24 hours.
FIG. 3B is a histogram depicting blood glucose levels at −0.5 hour pre-dosing, 2 hours post-dosing and 4 hours post-dosing in mice dosed with 100 mg/kg GDC-0068 and pretreated with REMD2.59c or ASN vehicle for 24 hours.
FIG. 3C is a histogram depicting blood glucose levels at −0.5 hour pre-dosing, 2 hours post-dosing and 4 hours post-dosing in mice dosed with 10 mg/kg GDC-0980 and pretreated with REMD2.59c or ASN vehicle for 24 hours.
FIG. 3D is a histogram depicting blood glucose levels at −0.5 hour pre-dosing, 2 hours post-dosing and 4 hours post-dosing in mice dosed with 30 mg/kg GSK690693 and pretreated with REMD2.59c or ASN vehicle for 24 hours. The black bars represent ASN treated mice. The gray bars represent mice pretreated with REMD2.59c.

The results are plotted as histograms in FIG. 3. The effect of REMD 2.59c pretreatment on GDC-0980, GSK690693, GDC-0068 and OSI-906 induced hyperglycemia are represented in histogram form in FIG. 3 (A. OSI-906, B. GDC-0068, C. GDC-0980, D. GSK690693) in which the black bars indicate ASN pretreated mice, and gray bars indicate REMD2.59c pretreated mice. Circulating glucose was also increased 3.0-3.2 fold after 2 h treatment in mice that received GDC-0980, GSK690693, GDC-0068, and OSI-906 (Table 3). The drug induced hyperglycemic effect with GDC-0980, GSK690693, GDC-0068, and OSI-906 was partially reduced at 2 h by REMD2.59c pretreatment. However, hyperglycemia persisted at 4 h after dosing with these PI3K/AKT inhibitors, and REMD 2.59 was generally not protective.

The current information on the kinase selectivity the inhibitors characterized in Examples 1 and 2 are listed in Table 2. Low or absent mTOR cross-reactivity distinguishes the kinase specificity of BYL719 and BKM120 from GDC-0980. MK2206 differs from GSK690693 and GDC-0068 in two respects. MK2206 an allosteric pan AKT inhibitor, whereas GSK690693 and GDC-0068 are ATP competitive inhibitors targeting the enzyme active site directly. GSK690693 and GDC-0068 are less selective for AKT than MK2206. The off-target kinases inhibited by GSK690693 and GDC-0068, including PKA, PKC, PKG, PRKG and others, are known to regulate diverse aspects of metabolism and cellular biology.

Based on this information, it appears that the ability of GCGR inhibition to control PI3K drug induced hyperglycemia depends on high PI3K specificity and the lack of mTOR kinase cross-reactivity. Effective normalization of drug induced hyperglycemia by GCGR blockade with AKT inhibitors appears is linked to high AKT specificity, and an allosteric, rather than ATP competitive, mechanism of kinase inhibition.

REMD 2.59c pretreatment was not able to control hyperglycemia induced by OSI-906, an ATP competitive inhibitor, that is equally potent against INSR, IGF1R and IRR. In contrast, it has been recently shown that GCGR inhibition with an antibody antagonist (REGN1193) can normalize blood glucose in C57BL/6 mice made severe insulin-resistant mice using and peptide INSR antagonist (S961) (Okamoto et al., PNAS, 114(10):2753-2758, 2017). This peptide antagonist blocks insulin binding to the receptor extracellular domain. Since IGF1R and IRR are not expressed in hepatocytes, as seen with AKT inhibitors, it also appears that an ATP competitive INSR kinase inhibitor mechanism is in compatible with the correction of hyperglycemia by GCGR inhibition.

Example 3

BALB/c athymic nude mice are most often used to characterize the efficacy of PI3K/Akt pathway inhibitors because these immunodeficient mice do not reject human tumor cell line xenograft. An experiment was performed to determine if tumor bearing BALB/c athymic nude mice recapitulate the hyperglycemic and hyperinsulinemic responses to PI3K/AKT pathway inhibition observed in humans and C57BL/6 mice.

BALB/c athymic nude mice (Anikeeper, Beijing) were inoculated subcutaneously with $5\times10^6$ human MiaPaCa2 pancreatic cancer cells in DMEM: Matrigel (1:1). Twenty-nine days later, the mice were randomized according to body weight (21.8+0.7 g) and tumor volume (334±27). Nine animals were pretreated with REMD2.59c or ASN vehicle for 24 hr. The animals were then administered MK2206 (150 mg/kg; p.o.) formulated as indicated in Example 2. Fed blood glucose were determined at 0.5 h before dosing, and at 2 h and 4 h postdosing by a tail nick using an Accu-Chek Performa System (Roche Diagnostics). Fed blood samples were taken by orbital bleed, and serum samples were prepared and stored at $-80°$ C. insulin. Serum insulin levels were measured using the Ultra-Sensitive Mouse Insulin ELISA Kit (Crystal Chem, Cat #: 90080). The influence of animal stress during on glucose and insulin levels was minimized by avoiding sampling separate mouse groups (n=3) for each time point.

Statistical analysis of glucose and insulin levels in response to AKT inhibition with MK2206 inhibition was performed GraphPad Prism 5.0. software. The group mean, standard deviations were calculated and unpaired t-test comparisons test were applied with a level of significance was set at 5% or $P<0.05$.

Figure 4:
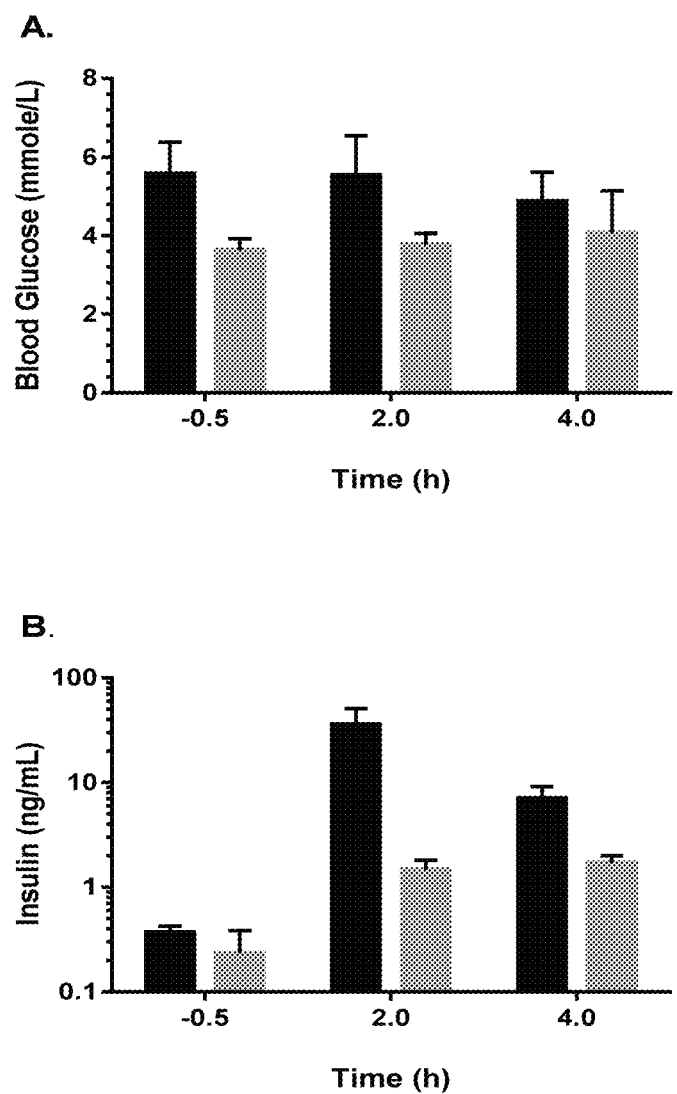
FIG. 4A is a histogram depicting blood glucose levels at −0.5 hour pre-dosing, 2 hours post-dosing and 4 hours post-dosing in Balb/c athymic nude mice orally dosed with 150 mg/kg MK2206 and pretreated with REMD2.59c or ASN vehicle for 24 hours.
FIG. 4B is a histogram depicting insulin levels at −0.5 hour pre-dosing, 2 hours post-dosing and 4 hours post-dosing in mice dosed with 150 mg/kg MK2206 and pretreated with REMD2.59c or ASN vehicle for 24 hours. The black bars represent ASN treated mice. The gray bars represent mice pretreated with REMD2.59c.

The mean/sd of baseline and treatment glucose and insulin levels obtained with BALB/c nude tumor bearing mice are treated with MK2206 with/without REMD2.59c pretreatment are listed in Tables 4 and 5. The results were plotted as histograms in FIG. 4 (A. glucose level, B insulin level) in which ASN treated mice are represent by the black bar, and gray bars represent REMD2.59c treated mice. Unlike the results obtained with C57BL/6 mice in Example 1, glucose levels were not increased in BALB/c nude mice after 2 h treatment with MK2206. However, treatment of BALB/c nude mice with MK2206 for 2 h was associated with a statistically significant 65.5-fold increase in serum insulin. The results are consistent with data previously reported in tumor bearing athymic nude mice treated with BYL719 (Fritsch et al., Mol Cancer Ther, 13(5):1117-29, 2014). These authors reported that hyperglycemia with hyperinsulinemia appeared upon extended repeated dosing and only at high BYL719 doses above a "hyperglycemic threshold" of about 20 uMole/L drug concentration.

MiaPaCa2 tumors may have suppressed glucose elevation the BALB/c nude mice in response to MK2206 treatment. To examine this possibility, the MK2206 dosing protocol was repeated in naïve BALB/c nude mice. The glucose levels listed obtained with naïve mice are indistinguishable from control and MK2206 treated tumor bearing mice. These results ruled out the possibility that drug induced hyperglycemia was masked by MiaPaCa2 tumor glucose uptake or another tumor related mechanism.

Pretreatment of the BALB/c athymic nude bearing MiaPaCa2 tumors reduced glucose levels by 1.6-fold. The reduction in fed glucose was similar to the effect obtained in C57BL/67 mice after 24 h treatment with REMD2.59c. This result suggests that the multigenic genotype that distinguishes BALB/c athymic nude and C57BL/6 mice does not affect the islet-liver endocrine axis. The genotypes of C57BL/6 and BALB/c athymic nude mice are differ at multiple genetic loci (Belizario, J E, The Open Immunology Journal, 2(1), 2009). The athymic nude immunodeficient phenotype is associated with a spontaneous mutation in Foxn1.

The induction of hyperinsulinemia by MK2206 treatment was reduced by at least 92% in BALB/c athymic nude tumor bearing mice pretreated with REMD2.59c. The 2 h insulin level in REMD2.59c pretreated mice was only 3-fold elevated compared to the −0.5 h baseline. Taken together, the results described in Example 1 and Example 3 with MK2206 indicate that the hyperglycemia and hyperinsulinemia associated with INSR pathway inhibition are both reversed by REMD2.59c pretreatment in combination with AKT blockade.

S961 is a peptide antagonist that binds the extracellular domain of INSR and inhibits receptor signaling. Okamoto et. al. (2017) have recently reported that GCGR inhibition with an antagonistic antibody (REGN1193) can largely correct hyperglycemia induced by insulin receptor blockade with S961 in C57BL/6 mice (Okamoto et al., PNAS, 114 (10):2753-2758, 2017). However, REGN1193 treatment did not correct hyperinsulinemia in this model; in fact, insulin levels were increased. Therefore, PI3K inhibition (for example with BKM719 and BKM120), or inhibition of AKT (for example with MK220K), rather than INSR inhibition, may be essential for the correction of hyperglycemia and hyperinsulinemia in cancer therapy and other indications for PI3K/AKT pathway inhibition.

TABLE 4

Effects of MK2206 and REMD2.59c on glucose in BALB/c mice

| Tumor Status* | −24 h Drug Treatment | 0 h Drug Treatment | −0.5 h Glucose (mM) | 2 h Glucose (mM) | 4 h Insulin (ng/mL) |
|---|---|---|---|---|---|
| MiaPaCa2 | ASN | MK2206 (150 mg/kg) | 5.6 ± 0.8 | 5.5 ± 1.0 | 4.9 ± 0.8 |
| MiaPaCa2 | REMD2.59c | MK2206 (150 mg/kg) | 3.6 ± 0.3 | 3.8 ± 0.3 | 4.1 ± 1.1 |
| Naïve | None | MK2206 (150 mg/kg) | 5.7 ± 0.9 | 5.8 ± 0.5 | 5.7 ± 1.0 |

Note:

*Tumor bearing BALB/c mice carried ~0.3 mm³ MiaPaCa2 tumor xenografts. Naïve mice were tumor-free.

TABLE 5

Effects of MK2206 and REMD2.59c on insulin in BALB/c mice

| Tumor Status* | −24 h Drug Treatment | 0 h Drug Treatment | −0.5 h Glucose (mM) | 2 h Glucose (mM) | 4 h Insulin (ng/mL) |
|---|---|---|---|---|---|
| MiaPaCa2 | ASN | MK2206 (150 mg/kg) | 0.4 ± 0.1 | 26.2 ± 19.4 | 7.1 ± 2.1 |
| MiaPaCa2 | REMD2.59c | MK2206 (150 mg/kg) | 0.3 ± 0.2 | 1.5 ± 0.3 | 1.7 ± 0.3 |

Example 4

The present inventors wish to determine the extent to which co-administration with REMD2.59C enables increased PI3K inhibitor target coverage in mice, and to determine how well any resultant increased PI3K inhibitor coverage is tolerated in the mice. In this Example, the combination therapy comprises administration of a chimeric anti-GCGR antibody which comprises the heavy chain sequence set forth in SEQ ID NO: 8 and the light chain sequence set forth in SEQ ID NO: 9 ("REMD2.59C") and administration with the PI3K inhibitors, BYL719 and BKM120, and AKT inhibitor MK2206.

A tolerability study is performed as follows: C57BL/6 mice (Vital River Laboratory Animal Technology Co., LTD) (male, age 8-10 weeks), or CB17 scid mice (Vital River Laboratory Animal Technology Co., LTD) (female, 8-10 weeks) are raised post-weaning on normal diets and randomization by weight (typically 20-22 gms) into six groups (n=12 animals per group). Three groups of mice (groups 1, 2 and 3) are dosed with REMD2.59C antibody (7.0 mg/kg, s.c., day 1, 4, 7 and 10) and three groups (groups 4, 5 and 6) are dosed with IgG1 control antibody 7.0 mg/kg, s.c., day 1, 4, 7 and 10). Treatment of each group with BYL719, BKM120 or MK2206 at begins on day 2: groups 1 and 4 (BYL719, BKM120 50 mg/kg, or MK2206 150 mg/kb); groups 2 and 5 (PI3K/AKT inhibitor dose increased 2-fold); groups 3 and 6 (PI3K/AKT inhibitor dose increased 3-fold). Group 7 will receive IgG1 control antibody alone. Group 8 will receive REMD2.59c alone.

Body weights are measured during the day at a consistent time before dosing. Body weights of all animals are measured daily throughout the study. Body weight change, expressed in %, is calculated using the following formula: BW change (%)=BWDayX/BWDay0 x 100, where BWDayX is BW on a given day, and BWDay0 is BW on Day 0 (initiation of BYL719 treatment). Body weight reduction of greater than 5% is assigned as the safety threshold determining maximum tolerated dose (MTD) in accordance with previous characterizations of BYL719 and BKM120 (Fritsch et al., Mol Cancer Ther, 13(5):1117-29, 2014). The weight of gastrocnemius muscle and epididymal fat mice are determined to distinguish between healthy and pathological weight loss. The necropsy includes weight measurements of metabolically active organs (liver and kidney) and any gross pathological findings.

The in life pharmacodynamic markers to further assess target cover include blood glucose, serum insulin and glucagon. A sampling protocol is employed (n=4) for each group that minimizes animal stress effects caused by repeated dosing. Fed blood glucose is measured by tail vein nick measured via tail veins using Accu-Chek Performa System (Roche Diagnostics). The blood glucose collection alternated between 2 h pre-dosing, and 2 h post dosing, over 10 days to capture the maximum and minimum PI3K or AKT target coverage. Blood samples are collected by orbital bleed (n=4 for each group on Day 1, 4 and 10 (2 h post dosing) to determine the maximum effect of PI3K or AKT inhibition on insulin and glucagon levels. Serum samples are prepared and stored at −80° C. insulin. Serum insulin is measured by the Ultra-Sensitive Mouse Insulin ELISA Kit (Crystal Chem, Cat #: 90080).

Terminal blood and liver tissue are collected from each group on Day 10 at 2, 4 and 8 h post dosing (n=4 per time point) for more extensive marker analysis. Blood samples (approximately 800 µL) are collected from each animal at the scheduled sample collection time by terminal cardiac puncture into tubes containing K2EDTA as an anticoagulant and centrifuged at 1500-2000 g to isolate plasma. Plasma is stored at −80° C. BYL719, BKM120 and MK2206 plasma concentrations are determined by standard LC/MS/MS methodology. REMD2.59c concentration are determined by ELISA. Glucose, amino acids and catabolites (Orn, Lys, Met, Thr, Gly, aminomalonic acid, Asn, His, Cys, 2-aminoadiptic acid, Gln, Ser, Pro, Citrulline, N-methyl-Ala, Ala, Tyr, Asp, Glu, Leu, homo-serine, Met Sulfoxide, b-Ala, Lie, Val, N-acetyl-Glu/Gln, creatine, Phe, Trp), and other metabolite are quantitated by LC/MS/MS profiling (Metabolon Inc. Durham, N.C.). Plasma hormones will be measure by using the Ultra-Sensitive Mouse Insulin ELISA Kit (Crystal Chem, Cat #: 90080), and Mouse Glucagon ELISA Kit (Crystal Chem Cat #81518).

Terminal liver samples (N=4 for each group at 2, 4, and 8 h post dosing are flash frozen and store at −80° C. The tissues are homogenized in RIPA (10 mM Tris-CI (pH 8.0), 1 mM EDTA, 1% Triton X-100, 0.1% sodium deoxycholate, 0.1% SDS, 140 mM NaCl, cOmplete™ Protease Inhibitor Cocktail (Cat #11697498001 Sigma-Aldrich), Phosphatase Inhibitor Cocktail Cat #P2850 SIGMA) and clarified by centrifugation at 10K RPM at 4° C. Total AKT, S473P-Akt, and gluconeogenic enzymes (ALT, AST PEPCK, pCREB) are measured by quantitative IP/westerns using standard methods.

As shown in Examples 1 and 2 the glucose values can be taken as an indication of hepatic PI3K or AKT target inhibition in the absence of REMD2.59c treatment (Group 7). The reduction in glucose observed in Group 8 with antibody alone is an indicator of the extent of GCCR blockade. The correction of hyperglycemia in the treatment group is calculated as using the formula: G %=(G2/G1)× 100, where G2 in the glucose level for combined drug treatment at a particular PI3K or AKT inhibitor dose, G1 is the glucose level obtained with PI3K or AKT inhibitor alone. The same calculation will be applied to all pharmcodynamic markers.

Target exposure is individually related to circulating pharmocodynamic markers using PK and other analysis software (GraphPad PRISM). The PK/PD relationship for each dose level is established by comparing % of inhibition of hepatic S473P-Akt levels with PI3K or AKT inhibitor concentration versus control at each time point indicated. It is anticipated that the co-administration of REMD2.59C will result in an increase target coverage ~2-3 over the dosing period without increasing body weight loss above 5% or other adverse effects. The analysis should further validate circulating biomarkers for calibrating combined and individual dosing of REMD477 and BYL791, BKM120 and MK2206 in human clinical trials. The predicted behavior of the pharmacodynamic markers is listed in Table 6.

TABLE 6

Predicted Marker Responses to GCGR and PI3K/AKT inhibition

| Circulating Marker | REMD2.59C | BYL791, BKM120, MK2206 | Combined* |
|---|---|---|---|
| Glucose | 30-40% Reduced | 2-3 fold Increase | Normoglycemia |
| Insulin | 30-40% reduced | 40-60 fold Increased | >90% Normalized |
| Glucagon | 10-100 fol Increased | 2-3 fold Increased | 10-100 fold increased |
| Amino Acids (e.g. Gln, Ala) | 5-10 fold Increased | Reduced | 5-10 fold Increased |
| Liver pAKt/tAKT | No Change | 30-80% Reduced | 30-80% Reduced |
| PEPCK, pCREB | 5-10 fold reduced | Increased | 5-10 fold Reduced |

Example 5

In this example, the present inventors wish to evaluate the extent to which co-administration with REMD2.59C leads to increased antitumor efficacy in using human tumor xenograft models. The experiments are designed determine the influence of PIK3CA mutations and PTEN mutations with loss-of-heterozygosity on the efficacy of tumor growth inhibition (TGI). It has been reported that PTEN null status confers resistance to BYL719, whereas BKM120 and AKT inhibitor can be effective in PTEN null tumor xenografts (Fritsch et al., Mol Cancer Ther, 13(5):1117-29, 2014). In this Example, the combination therapy comprises administration of a chimeric anti-GCGR antibody which comprises the heavy chain sequence set forth in SEQ ID NO: 8 and the light chain sequence set forth in SEQ ID NO: 9 ("REMD2.59C") and administration with the PI3K inhibitor, BYL719 and BKM120, and the MK2206 AKT inhibitor.

The global DNA copy number, mutation status, RNA expression level and epigenetics of at least 1000 human cancer cell lines employed for preclinical research has been completely assessed using genomic technologies (Barretina et al., Nature, 483(7391), 603-7, 2012). Human cancer cell lines that carry PIK3CA mutations, or that are PTEN null, are readily identified in this public data (COSMIC, CCLE, broadinstitute.org). The cell line genomic data includes information for mutated or altered genes that may modify the influence of PIK3CA mutation or PTEN loss on the tumorgenicity, growth and survival as mouse xenografts. A human tumor xenograft panel to characterize the influence of PIK3CA mutations and PTEN loss on PI3K or AKT inhibition combined with GCGR blockade is listed in Table 7. These human xenografts can be replaced with cancer cells lines with similar or identical genotypes identified in COSMIC or CCLE. The current preclinical evidence indicates that the efficacy of PI3Ka selective BYL719 is limited to PIK3CA mutant and wild type tumors (Fritsch et al., Mol Cancer Ther, 13(5):1117-29, 2014). BKM120, a pan-specific PI3K inhibitor, a MK2206, acting on AKT downstream of PI3K/PTEN, are predicted to be more effect against PTEN null cancer.

TP53, KRAS and ERBB2 are genetic alterations know to potentiate the effect of PIK3CA mutations and PTEN loss on tumor growth and invasion (Rodon et al, Nat Rev Clin Oncol, 10(3):143-53, 2013). The selection of TP53, KRAS and ERBB2 mutated or amplified xenograft models in this Example is designed illuminate the role of these genes as predictive markers for patient selection and impact resistance to PI3K/AKT inhibitors.

TABLE 7

Human cancer cell line mutations and gene amplification

| Cell Line Xenograft | Histology | PIK3CA | PTEN | TP53 | ERBB2 | K-Ras |
|---|---|---|---|---|---|---|
| A375 | Skin | wild type | wild type | wild type | normal | wild type |
| Mia PaCa-2 | Pancreas | wild type | wild type | p.R248W | normal | p.G12C |
| Colo 205 | colon | wild type | wild type | p.Y103R110del | normal | wild type |
| NCI-N87 | Stomach | wild type | wild type | p.R248Q | normal | wild type |
| MCF7 | Breast | p.E545K het | wild type | wild-type | normal | wild type |
| BT-474 | Breast | p.K111N het | Wild type | p.E285K | amplified | wild type |
| NCI-H1770 | Lung | wild type | p.Y177* | p.R248W | normal | wild type |
| NCI-H196 | Lung | wild type | p.Y138C | p.R175H | normal | wild type |

Note:
The PI3KCA mutations are heterozygous. All other Mutations are homozygous

CB17 scid mice (Charles River Labs) are inoculated subcutaneously ($0.5-1.5 \times 10^7$ cells) on the right flank with tumor cells in 0.2 ml of growth medium with matrigel. The optimal number of cells, growth medium and matrigel ratio for each cell line has been previously determined. Tumor development is allowed undisrupted until the mean volume reached approximately 200 mm³. Mice are assigned to 7 groups (n=12 mice per group) using a computer-generated randomization procedure.

REMD2.59c, BYL719, BKM120 and MK2206 are formulated and administered as described in Example 1. The treatment and control groups are listed in Table 8 for a combination study evaluating REMD477 combined with BYL719 in CB-17 scid mice with Mia PaCa-2 tumors. The same dosing scheme would apply to other xenograft models. REMD2.59c is administered at a saturating dose (7.0 mg/kg) that maximally inhibits GCGR signaling and effectively reduce drug induced hyperglycemia and hyperinsulinemia (Example 1 and Example 2). The PI3K and AKT inhibitors are tested at three doses. The highest dose exceeds the previously reported maximum dose for mouse xenograft models by 50 to 100 percent. The dose range for a BKM120 combination study would be 50, 100, 150 mg/kg (p.o.) daily. MK2206 doses would be 150, 300, 450 mg/kg (p.o.) daily.

The measurements of tumor size are conducted twice weekly with a caliper and the tumor volume (mm³) are estimated using the formula: TV=a×b²/2, where "a" and "b" are long and short diameters of a tumor, respectively. Tumor growth inhibition (TGI) is determined using the formula: TGI=(1−T/C)×100%, where "T" and "C" are the mean relative volumes (% tumor growth) of the tumors in the treated and the vehicle control group, respectively.

induced by repeated sampling. As shown in Examples 1 and 2 the glucose values can be taken an indication of hepatic PI3K or AKT target inhibition in the absence of REMD2.59c treatment (Group 1). The reduction in glucose observed in Group 8 with antibody alone is an indicator of the extent of GCCR blockade. The correction of hyperglycemia in the treatment group is calculated as using the formula: G %=(G2/G1)×100, where G2 in the glucose level for combined drug treatment at a particular PI3K or AKT inhibitor dose, G1 is the glucose level obtained with PI3K or AKT inhibitor alone.

Upon receiving the final dose PI3K or AKT inhibitor 4 mice from each group will be sacrificed for collection of blood, liver and tumor tissue at 2, 4 and 8 h post dosing. Serum is prepared from blood and stored at −80° C. for later analysis of circulating PI3K or AKt inhibitor, glucose, insulin, glucagon, amino acids derivative metabolites using ELISA assays for REMD2.59c and hormones, and LC/MS/MS methods for metabolites and drugs as described in Example 4. Each liver or tumor tissue is flash frozen, then pulverized and analyzed by RPPA lysis buffer to determine S473P-Akt levels and, in parallel, the concentration of PI3K or AKT is quantified by a standard LC/MS/MS method.

A PK/PD relationship for each dose level is established by comparing % of inhibition of S473P-Akt levels versus control with NPI3K or AKT concentration at each time point

TABLE 8

Dosing scheme for CD17 scid Mia PaCa-2 tumor bearing mice

| Group (n = 12) | Antibody treatment | | BYL719 Treatment |
|---|---|---|---|
| 1 | Control IgG1 | 7 mg/kg, i.p., 2x/wk | Vehicle | NA |
| 2 | Control IgG1 | 7 mg/kg, i.p., 2x/wk | BYL719 | 50 mg/kg, p.o., daily |
| 3 | Control IgG1 | 7 mg/kg, i.p., 2x/wk | BYL719 | 100 mg/kg, p.o., daily |
| 4 | Control IgG1 | 7 mg/kg, i.p., 2x/wk | BYL719 | 150 mg/kg, p.o., daily |
| 5 | REMD2.59c | 7 mg/kg, i.p., 2x/wk | BYL719 | 50 mg/kg, p.o., daily |
| 6 | REMD2.59c | 7 mg/kg, i.p., 2x/wk | BYL719 | 100 mg/kg, p.o., daily |
| 7 | REMD2.59c | 7 mg/kg, i.p., 2x/wk | BYL719 | 150 mg/kg, p.o., daily |
| 8 | REMD2.59c | 7 mg/kg, i.p., 2x/wk | Vehicle | NA |

For routine monitoring, all study animals are monitored not only tumor growth but also behavior such as mobility, food and water consumption (by cage side checking only), body), eye/hair matting and any other abnormal effect. Any mortality and/or abnormal clinical signs is recorded. Body weight change is measured twice weekly as described in Example 4. Body weight reduction of greater than 5% is assigned as the safety threshold determining maximum tolerated dose (MTD) in accordance with previous characterizations of the BYL719 and BKM120 (Fritsch et al., Mol Cancer Ther, 13(5):1117-29, 2014).

The mean±SEM for tumor volume and relative BW change, and glucose level for control and treated groups is calculated using GraphPad PRIZM software and plotted against day of treatment to identify trends. The TGI (%) and BW (%) change for each group at the end of the treatment period is tabulated. Repeated measures ANOVA followed by post hoc Scheffe is used to compare reduction in tumor volume and body weight in mice treated with BYL719, BKM120 or MK2206 alone or in combination REMD2.59C.

Fed blood glucose monitored twice weekly at 2 h post-dosing, and 2 hr predosing, with PI3K or AKT inhibitor to capture the glucose effect at peak and trough inhibitor levels. Three mice are selected from each group for each glucose measurement in using a protocol that avoids animal stress indicated. Target coverage and tumor exposure is individually related to circulating pharmacodynamic markers using PK and other analysis software (GraphPad PRISM). It is expected that the co-administration of REMD2.59C will result in an increase target coverage 2-3 fold (from 30% to >80% in the case of BYL719) for the full duration of the dosing interval, and a corresponding increase antitumor efficacy in PI3KA mutant, amplified and, and wildtype tumors (Fritsch et al., Mol Cancer Ther, 13(5):1117-29, 2014). An $ED_{50}$ for PI3K and AKT inhibitors is derived from the analysis of PK (Cmax/AUC) and TGI. The analysis should further validate circulating biomarkers that will enable an understanding of PI3K or AKT inhibitor drug dose versus effect in human.

Example 6

In this example, the present inventors wish to further explore the relationship between liver and tumor AKT inhibition (with and without REMD2.59 administration) and blood and tissue biomarker behavior in tumor xenograft models (wild type PIK3A mutant, and PTEN null). In this Example, the combination therapy comprises administration of a single dose of a chimeric anti-GCGR antibody which comprises the heavy chain sequence set forth in SEQ ID NO: 8 and the light chain sequence set forth in SEQ ID NO: 9

("REMD2.59C") and administration with the PI3K inhibitors BYL719, BKM 120 and MK2206. Biomarker measurements are obtained over a period approximating the PI3K and AKT inhibitor dosing interval. Biomarker associations in a single dose in vivo pharmacodynamics (PK/PD) of this type is not influenced by physiological and cellular alterations associated by repeated long-term dosing as described in Example 4 and Example 5.

An in vivo pharmacodynamics (PK/PD) study is performed with A375 (PIK3CA and PTEN wild type), MCF7 (PIK3CA mutant) and NCI-1196 (PTEN null) tumor xenograft in CB-17 scid mice. Tumors are initiated as described in Example 5. When the average tumor size reached approximately 300 mm$^3$, mice are randomly assigned into eight groups and dosed as described in Table 9 using A375 tumors and BYL719 as example. REMD2.59c, BYL719, BKM120 and MK2206 are formulated and administered as described in Example 1. Mice are pretreated with control IgG1 or REMD2.59c for 24 h before administration of BYL719. REMD2.59c is administered at a saturating dose (7.0 mg/kg) that maximally inhibits GCGR signaling and effectively reduce drug induced hyperglycemia and hyperinsulinemia (Example 1 and Example 2). BYL719 is tested at three doses. The highest dose exceeds the previously reported maximum dose for mouse xenograft models by 50 to 100 percent. The same dosing scheme would apply to other xenograft models. The dose range for a BKM120 combination study is 50, 100, 150 mg/kg (p.o.) daily. MK2206 doses are 150, 300, 450 mg/kg (p.o.) daily.

Three animals from each group are sacrificed at 1 h, 2 h, 4 h, and 8 h post dosing for blood, liver and tumor tissue collection. Blood samples (approximately 800 µL) are collected from each animal at the scheduled sample time by cardiac puncture into tubes containing K2EDTA as an anticoagulant and centrifuged at 1500-2000 g to isolate plasma. Plasma is stored at −80° C. BYL719, BKM120 and MK2206 plasma concentrations are determined by standard LC/MS/MS methodology. REMD2.59c concentration is determined by ELSIA with anti-diotypic antibodies. Glucose level is determined by tail nick before sacrifice using Accu-Chek Performa System (Roche Diagnostics). Plasma hormones are measured by using the Ultra-Sensitive Mouse Insulin ELISA Kit (Crystal Chem, Cat #: 90080), and Mouse Glucagon ELISA Kit (Crystal Chem Cat #81518).

Terminal liver samples (N=4 for each group at 2, 4, and 8 h post dosing are flash frozen and store at −80° C. The tissues are homogenized in RIPA (10 mM Tris-CI (pH 8.0), 1 mM EDTA, 1% Triton X-100, 0.1% sodium deoxycholate, 0.1% SDS, 140 mM NaCl, cOmplete™ Protease Inhibitor Cocktail (Cat #11697498001 Sigma-Aldrich), Phosphatase Inhibitor Cocktail Cat #P2850 SIGMA) and clarified by centrifugation at 10K RPM at 4° C. Total AKT, S473P-Akt, (liver and tumor) and liver enzymes (ALT, AST PEPCK, pCREB) are measured by quantitative IP/westerns using standard methods.

The mean±SEM for liver and tumor AKT status (pAKT, tAKT, pAKT/tAKT) is calculated for each group and plotted as a histogram. The same dat processing is applied to liver AKT, ALT, AST PEPCK and pCREB, blood glucose, blood insulin and glucagon, REMD2.59c, BYL719, BKM120 and MK2206 plasma concentrations. The statistical significance of differences between control, drug treated and untreated groups are evaluated with a student t-test. Graph Pad PRIZM software is used to identify correlations between GCGR and AKT inhibition and blood/tissue biomarkers. The anticipated results are the same as listed in Table 5 of the tolerability study. The analysis should further validate the immediate responses of circulating biomarkers for calibrating combined and individual dosing of REMD477 and BYL791, BKM120 and MK2206 in human clinical trials.

TABLE 9

Dosing groups for a PKPD analysis of BYL719 in CB17 scid A375 tumor bearing mice

| Group (n = 12) | Antibody pretreatment (T-24 hr) | | BYL719 Treatment T = 0 h | |
|---|---|---|---|---|
| 1 | Control IgG1 | 7 mg/kg, i.p. | Vehicle | NA |
| 2 | Control IgG1 | 7 mg/kg, i.p. | BYL719 | 50 mg/kg, p.o. |
| 3 | Control IgG1 | 7 mg/kg, i.p. | BYL719 | 100 mg/kg, p.o. |
| 4 | Control IgG1 | 7 mg/kg, i.p. | BYL719 | 150 mg/kg, p.o. |
| 5 | REMD2.59c | 7 mg/kg, i.p. | BYL719 | 50 mg/kg, p.o. |
| 6 | REMD2.59c | 7 mg/kg, i.p. | BYL719 | 100 mg/kg, p.o |
| 7 | REMD2.59c | 7 mg/kg, i.p. | BYL719 | 150 mg/kg, p.o. |
| 8 | REMD2.59c | 7 mg/kg, i.p. | Vehicle | NA |

Example 7

REMD477 is a fully human monoclonal antibody having the heavy chain sequence set forth in SEQ ID NO: 49 and the light chain sequence set forth in SEQ ID NO: 50 that binds the human GCGR and inhibits the metabolic action of glucagon mediated by receptor signaling (Yan et al., J Pharmco Exp Ther, 329(1): 102-111, 2009). A single dose of REMD-477 ((70 milligram (mg) subcutaneous)) has been shown to substantially reduce the amount of insulin needed and improve glucose levels without increasing hypoglycemia (low blood glucose levels) in patients with type 1 diabetes.

The safety and efficacy of BLY719, BKM120 and MK2206 have been extensively characterized in Phase I/II clinical trials with cancer patient of diverse malignancies (Nitulesca et al., International Journal of Oncology, 48(3): 869-885, 2016. Efficacy has been minimal and hyperglycemia and hyperinsulinemia have been consistently observed (Borthakur et al., 56th Annual Meeting of the American Society of Hematology (ASH) 2014).

A clinical study to establish the potential utility of combining REMD477 with BYL719, BKM120 or MK2206 would occur in two phases. Phase 1 would evaluate the safety of combined administration and validate predictive markers identified in preclinical studies described in Examples 4-6. Phase 2 would efficacy combined GCGR and PI3K or AKT pathway inhibition in cancers with and without PIK3CA and PTEN null mutations.

Phase 1: A single dose level of REMD477 (70 mg/once weekly) will be evaluated in Phase I since it appears to be saturating with respect to glucose normalization in humans. Dosing with BYL719, BKM120 and MK2206 will start at one-half the MTD reported clinical and increased 2-fold up to twice the MTD. The Phase I dosing would follow the standard 3+3 design [7]. REMD477 PK will utilize previously validated ELISA with anti-idotypic antibodies. Plasma BYL719, BKM120, and MK220K PK will be determined over a 1 day period (2, 4, 8, 16 h) by using previous described LC/MS/MS methods. Plasma glucose, and candidate amino acid and metabolite pharmacodynamic markers will be monitored in each PK sample using LC/MS/MS (Metabolon Inc, Druham, N.C.). Plasma insulin and glucagon level will be determined with certified clinical assays. The appropriate statistical analysis will determine the validity of the PKPD predictions listed in Table 5 of Example 4, and the ability of REMD477 to correct drug induced hyperglycemia and hyperinsulinemia in human cancer patients.

Phase 2: The Phase 2 the trial would compare two groups: Arm 1 would receive the oncologic BYL719, BKM120 or MK2206 treatment (at the standard dose); Arm 2 would receive REMD477 (70 mg subcutaneously/once weekly) and BYL719, BKM120, and MK2206 at a higher dose depending on the outcome of Phase 1. The clinical hypothesis is that REMD477 can better control dose limiting hyperglycemia, and as a result, higher and potentially more efficacious PI3K/AKT pathway inhibition can be tolerated. Proof of concept would be that response rate, progression free survival and overall survival would be greater in patients receiving REMD477. The Phase 2 study would include weekly measurement of plasma glucose, insulin, drug levels and other circulating markers validate in Phase 1.

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes.

The disclosure illustratively described herein suitably may be practiced in the absence of any element(s) not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

Sequence Listings

The amino acid sequences listed in the accompanying sequence listing are shown using standard three letter code for amino acids, as defined in 37 C.F.R. 1.822.

SEQ ID NO: 1 is the amino acid sequence of a human glucagon receptor (GCGR) molecule (Accession Number AA104855).

SEQ ID NO: 2 is the amino acid sequence encoding the heavy chain variable region of a fully human anti-GCGR antibody. SEQ ID NO: 3 is the amino acid sequence encoding the light chain variable region of a fully human anti-GCGR antibody.

SEQ ID NO: 4 is the amino acid sequence encoding the heavy chain variable region of a fully human anti-GCGR antibody. SEQ ID NO: 5 is the amino acid sequence encoding the light chain variable region of a fully human anti-GCGR antibody.

SEQ ID NO: 6 is the amino acid sequence encoding the heavy chain variable region of a fully human anti-GCGR antibody. SEQ ID NO: 7 is the amino acid sequence encoding the light chain variable region of a fully human anti-GCGR antibody.

SEQ ID NO: 8 is the amino acid sequence encoding the heavy chain of a chimeric anti-GCGR antibody. SEQ ID NO: 9 is the amino acid sequence encoding the light chain of a chimeric anti-GCGR antibody.

SEQ ID NOS: 10-27 are amino acid sequences encoding the heavy chain variable regions of various fully human anti-GCGR antibodies.

SEQ ID NOS: 28-45 are amino acid sequences encoding the light chain variable regions of various fully human anti-GCGR antibodies.

SEQ ID NO: 46 is the amino sequence encoding the kappa light chain constant region. SEQ ID NO: 47 is the amino sequence encoding the lambda light chain constant region.

SEQ ID NO: 48 is the amino sequence encoding the IgG2 heavy chain constant region.

SEQ ID NO: 49 is the amino acid sequence encoding the heavy chain of a fully human anti-GCGR antibody. SEQ ID NO: 50 is the amino acid sequence encoding the light chain of a fully human anti-GCGR antibody.

---

SEQUENCE LISTINGS

SEQ ID NO: 1 - Amino acid sequence of a human glucagon receptor (GCGR) molecule
MPPCQPQRPLLLLLLLLACQPQVPSAQVMDFLFEKWKLYGDQCHHNLSLLPPPTELVCNRTFD
KYSCWPDTPANTTANISCPWYLPWHHKVQHRFVFKRCGPDGQWVRGPRGQPWRDASQCQ
MDGEEIEVQKEVAKMYSSFQVMYTVGYSLSLGALLLALAILGGLSKLHCTRNAIHANLFASFVLK
ASSVLVIDGLLRTRYSQKIGDDLSVSTWLSDGAVAGCRVAAVFMQYGIVANYCWLLVEGLYLH
NLLGLATLPERSFFSLYLGIGWGAPMLFVVPWAVVKCLFENVQCWTSNDNMGFWWILRFPVFL
AILINFFIFVRIVQLLVAKLRARQMHHTDYKFRLAKSTLTLIPLLGVHEVVFAFVTDEHAQGTLRSA
KLFFDLFLSSFQGLLVAVLYCFLNKEVQSELRRRWHRWRLGKVLWEERNTSNHRASSSPGHG
PPSKELQFGRGGGSQDSSAETPLAGGLPRLAESPF SEQ ID NO: 2 - Amino acid sequence of a HCVR of a human antibody that binds GCGR
QVQLVESGGGVVQPGRSLRLSCAASGFTFSSYGMHWVRQAPGKGLEWVAVMWYD
GSNKDYVDSVKGRFTISRDNSKNTLYLQMNRLRAEDTAVYYCAREKDHYDILTGYN
YYYGLDVWGQGTTVTVSS SEQ ID NO: 3 - Amino acid sequence of a LCVR of a human antibody that binds GCGR
DIQMTQSPSSLSASVGDRVTITCRASQGIRNDLGWYQQKPGKAPKRLIYAASSLQSGV
PSRFSGSGSGTEFTLTISSVQPEDFVTYYCLQHNSNPLTFGGGTKVEIK

SEQUENCE LISTINGS

SEQ ID NO: 4 - Amino acid sequence of a HCVR of a human antibody that binds GCGR
QVQLVESGGGVVQPGRSLRLSCAASGFTFSSYGMHWVRQAPGKGLEWV
AVMWYDGSNKDYVDSVKGRFTISRDNSKNTLYLQMNSLRAEDTAVYYCAREKDHYDI
LTGYNYYYGLDVWGQGTTVTVSS SEQ ID NO: 5 - Amino acid sequence of a LCVR of a human antibody that binds GCGR
DIQMTQSPSSLSASVGDRVTITCRASQGIRNDLGWYQQKPGKAPKRLIYAASSLQSGV
PSRFSGSGSGTEFTLTISSLQPEDFVTYYCLQHNSNPLTFGGGTKVEIK SEQ ID NO: 6 - Amino acid sequence of a HCVR of a human antibody that binds GCGR
QVQLVESGGGVVQPGRSLRLSCAASGFTFSSYGMHWVRQAPGKGLEWVAVMWYD
GSNKDYVDSVKGRFTISRDNSKNTLYLQMNRLRAEDTAVYYCAREKDHYDILTGYNY
YYGLDVWGQGTTVTVSS SEQ ID NO: 7 - Amino acid sequence of a LCVR of a human antibody that binds GCGR
DIQMTQSPSSLSASVGDRVTITCRASQGIRNDLGWYQQKPGKAPKRLIYAASSLESGV
PSRFSGSGSGTEFTLTISSVQPEDFVTYYCLQHNSNPLTFGGGTKVEIK SEQ ID NO: 8 - Amino acid sequence of a heavy chain of a chimeric antibody that binds GCGR
MEFGLSWVFLVALLRGVQCQVQLVESGGGVVQPGRSLRLSCAASGFTFSSYGMHWVRQAPG
KGLEWVAVMWYDGSNKDYVDSVKGRFTISRDNSKNTLYLQMNRLRAEDTAVYYCAREKDHY
DILTGYNYYYGLDVWGQGTTVTVSSAKTTPPSVYPLAPGSAAQTNSMVTLGCLVKGYFPEPVT
VTWNSGSLSSGVHTFPAVLQSDLYTLSSSVTVPSSTWPSETVTCNVAHPASSTKVDKKIVPRD
CGCKPCICTVPEVSSVFIFPPKPKDVLTITLTPKVTCVVVDISKDDPEVQFSWFVDDVEVHTAQT
QPREEQFNSTFRSVSELPIMHQDWLNGKEFKCRVNSAAFPAPIEKTISKTKGRPKAPQVYTIPP
PKEQMAKDKVSLTCMITDFFPEDITVEWQWNGQPAENYKNTQPIMDTDGSYFVYSKLNVQKS
NWEAGNTFTCSVLHEGLHNHHTEKSLSHSPGK SEQ ID NO: 9 - Amino acid sequence of a light chain of a chimeric antibody that binds GCGR
MDMRVPAQLLGLLLLWFPGARCDIQMTQSPSSLSASVGDRVTITCRASQGIRNDLGWYQQKP
GKAPKRLIYAASSLESGVPSRFSGSGSGTEFTLTISSVQPEDFVTYYCLQHNSNPLTFGGGTKV
EIKRADAAPTVSIFPPSSEQLTSGGASVVCFLNNFYPKDINVKWKIDGSERQNGVLNSWTDQDS
KDSTYSMSSTLTLTKDEYERHNSYTCEATHKTSTSPIVKSFNRNEC SEQ ID NO: 10 - Amino acid sequence of a HCVR of a human antibody that binds GCGR
QVQLVESGGGVVQPGRSLRLSCAASGFTFSNYGMHWVRQAPGKGLEWVAVILSDGRNKYYA
DSVKGRFTISRDNSKNTLYLQMNSLRAEDTAVYYCARDDYEILTGYGYYGMDVWGQGTTVTV
SS SEQ ID NO: 11 - Amino acid sequence of a HCVR of a human antibody that binds GCGR
QVQLVESGGGVVQPGRSLRLSCAASGFTFSSYGMHWVRQAPGKGLEWVAVILNDGRNKYYA
DSVKGRFTISRDNSKNTLYLQMNSLRAEDTAVYYCARDDYEILTGYGYYGMDVWGQGTTVTV
SS SEQ ID NO: 12 - Amino acid sequence of a HCVR of a human antibody that binds GCGR
QVQLQQSGPGLVKPSQTLSLTCAISGDSVSSNGAAWNWIRQSPSRGLEWLGRTYYRSKWYY
DYAGSVKSRININPDTSKNQFSLQVNSVTPEDTAVYYCTRDRSSGWNEGYYYYGMDVWGQG
TTVTVSS SEQ ID NO: 13 - Amino acid sequence of a HCVR of a human antibody that binds GCGR
QVQLVESGGGVVQPGRSLRLSCAASGFTFSSYDIHWVRQAPGKGLEWVAVLSSDGNNKYCA
DSVKGRFTISRDNSKNTLYLQMNSLRTEDTAVYYCAREEVYYDILTGYYDYYGMDVWGQGTTV
TVSS SEQ ID NO: 14 - Amino acid sequence of a HCVR of a human antibody that binds GCGR
QVQLQESGPGLVKPSETLSLTCTVSGGSISTYFWTWIRQFPGKGLEWIGYIFYSGSTNYNPSLK
SRVTISVDTSKNQFSLKLSSVTAADTAVYYCAREGYYDILTGEDYSYGMDVWGQGTTVTVSS SEQ ID NO: 15 - Amino acid sequence of a HCVR of a human antibody that binds GCGR
QVQLQQSGPGLVKPSQILSLICAISGDRVSSNGAAWNWIRQSPSRGLEWLGRTYYRSKWYYD
YAGSVKSRININPDTSKNQFSLQVNSVTPEDTAVYYCARDRSSGWNEGYYYYGMDVWGQGT
TVTVSS SEQ ID NO: 16 - Amino acid sequence of a HCVR of a human antibody that binds GCGR
QVQLQESGPGLVKPSETLSLTCTVSGGSISTYFWTWIRQFPGEGLEWIGYIFYSGNTNYNPSLT
SRVTISVDTSKNQFSLKLSSVTAADTAVYYCAREGYYDILTGEDYSYGIDVWGQGTTVTVSS SEQ ID NO: 17 - Amino acid sequence of a HCVR of a human antibody that binds GCGR
QVQLVESGGGVVQPGRSLRLSCAASGFIFSSYGMHWVRQAPGKGLEWVAVISNDGSNKYYA
DPVKGRFTISRDNSKNTLYLQMNSLRAEDTAVYYCAREDYDILTGNGVYGMDVWGQGTTVTV
SS SEQ ID NO: 18 - Amino acid sequence of a HCVR of a human antibody that binds GCGR
EVQLVESGGGLVQPGGSLRLSCAASGFTFSSYTMNWVRQAPGKGLEWVSYISGSSSLIYYAD
SVKGRFTISRDNAKNSLYLHMNSLRDEDTAVYYCARARYNWNDYYGMDVWGQGTTVTVSS -continued

SEQUENCE LISTINGS

SEQ ID NO: 19 - Amino acid sequence of a HCVR of a human antibody that binds GCGR
QVQLVESGGGVVQPGRSLRLSCAASGFAFSSYGIHWVRQAPGKGLEWVAGIWYDGSNKYYA
DSVKGRFTVSRDNSKNTLYLQMNSLRAEDTAVYYCARLFDAFDIWGQGTMVTVSS SEQ ID NO: 20 - Amino acid sequence of a HCVR of a human antibody that binds GCGR
EVQLVESGGGLVQPGGSLRLSCAASGFIFSSYTMNWVRQAPGKGLEWVSYISSSSSLIYYADS
VKGRFTISRDNAKNSLYLQMNSLRDEDTAVYYCARSDYYGSGSYYKGNYYGMDVWGQGTTV
TVSS SEQ ID NO: 21 - Amino acid sequence of a HCVR of a human antibody that binds GCGR
QVQLVESGGGVVQPGRSLRLSCAASGFTFSSYGMHWVRQAPGKGLEWVTIIWSDGINKYYAD
SVKGRFTISRDNSKNTLNLQMNSLRAEDTAVYYCARERGLYDILTGYYDYYGIDVWGQGTTVT
VSS SEQ ID NO: 22 - Amino acid sequence of a HCVR of a human antibody that binds GCGR
QVQLVESGGGVVQPGRSLRLSCAASGFTFSSYGMHWVRQAPGKGLEWVTIIWSDGINKYYAD
SVKGRFTISRDNSKNTLNLQMNSLRAEDTAVYYCARERGLYDILTGYYDYYGIDVWGQGTTVT
VSS SEQ ID NO: 23 - Amino acid sequence of a HCVR of a human antibody that binds GCGR
EVQLVESGGGLVKPGGSLRLSCAASGITFRSYSMNWVRQAPGKGLEWVSAISSSSSYIYYADS
VKGRFTISRDNAKNSVYLQMNSLRAEDTAVYYCARGRYGMDVWGQGTTVTVSS SEQ ID NO: 24 - Amino acid sequence of a HCVR of a human antibody that binds GCGR
QVQLVESGGGVVQPGRSLRLSCAASGSTFRSYDMHWVRQAPGKGLEWVAVISYDGSNKYYG
DSVKGRLTISRDNSKNTLYLQMNSLRAEDTAVYYCARDQYDILTGYSSDAFDIWGQGTMVTV
SS SEQ ID NO: 25 - Amino acid sequence of a HCVR of a human antibody that binds GCGR
QVQLVESGGGVVQPGRSLRLSCAASGFTFSRYGMHWVRQAPGKGLEWVAVIWYDGSHKYY
EDSVKGRFTISRDNSKNTLYLQMNSLRADDTGVYYCARVGYGSGWYEYYYHYGMDVWGQGT
TVTVSS SEQ ID NO: 26 - Amino acid sequence of a HCVR of a human antibody that binds GCGR
QVQLVESGGGVVQPGRSLRLSCAASGFTFSSYGMHWVRQAPGKGLEWVAVMWYDGSNKDY
VDSVKGRFTISRDNSKNTLYLQMNRLRAEDTAVYYCAREKDHYDILTGYNYYYGLDVWGQGTT
VTVSS SEQ ID NO: 27 - Amino acid sequence of a HCVR of a human antibody that binds GCGR
QVQLVESGGGVVQPGRSLRLSCAASGFTFSSYGMHWVRQAPGKGLEWVAVMWYDGSNKDY
VDSVKGRFTISRDNSKNTLYLQMNRLRAEDTAVYYCAREKDHYDILTGYNYYYGLDVWGQGTT
VTVSS SEQ ID NO: 28 - Amino acid sequence of a LCVR of a human antibody that binds GCGR
DIQMTQSPSSLSASVGDRVTITCRASQDISNYLAWFQKKPGKAPKSLIYVVSSLQSGVPSRFSG
SGSGTDFTLTINNLQPEDFATYYCQQYNHYPLTFGGGTRVEIKR SEQ ID NO: 29 - Amino acid sequence of a LCVR of a human antibody that binds GCGR
DIQMTQSPSSLSASVGDRVTITCRASQDISNYLAWFQQRPGKAPKSLIYVVSSLQSGVPSRFSG
SGSGTDFTLTISNLQPEDFATYFCQQYNHYPLTFGGGTKVEIKR SEQ ID NO: 30 - Amino acid sequence of a LCVR of a human antibody that binds GCGR
DIQMTQFPSSLSASIGDRVTITCQASQDISNFLNWFQQKPGKAPKLLIYDASDLETGVPSRFSGS
GAGTDFTFTISSLQPEDIATYFCQQYDDLPLTFGGGTRVDIKR SEQ ID NO: 31 - Amino acid sequence of a LCVR of a human antibody that binds GCGR
DIQMTQSPSSLSASVGDRVTITCRASQGIRNDLGWYQQKPGKAPKRLIYAASSLQSGVPSRFS
GSGSGTEFTLTISSLQPEDFATYYCLQHNSNPLTFGGGTKVEIKR SEQ ID NO: 32 - Amino acid sequence of a LCVR of a human antibody that binds GCGR
QNVLTQSPGTLSLSPGERVTLSCRASQSVSSSYLAWYQQKPGQAPRLLIFGVSSRATGIPDRF
SGSGSGTDFSLTISRLEPEDFAVYYCQQYGNSPFTFGPGTKVDIKR SEQ ID NO: 33 - Amino acid sequence of a LCVR of a human antibody that binds GCGR
DIQMTQFPSSLSASIGDRVTITCQASQDISNFLNWFQQKPGKAPKLLIYDASDLETGVPSRFSGS
GAGTDFTFTISSLQPEDVATYFCQQYDNLPLTFGGGTKVDIKR SEQ ID NO: 34 - Amino acid sequence of a LCVR of a human antibody that binds GCGR
ENVLTQSPGTLSLSPGERATLSCRASQSVTSSYLAWYQQKPGQAPRLLIFGVSSRATGIPDRF
SGSGSGTDFSLTISRLEPEDFAVYYCQQYGNSPFTFGPGTKVDIKR SEQ ID NO: 35 - Amino acid sequence of a LCVR of a human antibody that binds GCGR
DIQMTQSPSSLSASVGDRVTITCRASQGIDMYLAWFQQKPGKAPKSLIYAASSLQSGVPSKFS
GSGFGTDFTLTISSLQPEDFATYYCQQYNIFPFTFGPGTKVDVKR -continued

SEQUENCE LISTINGS

SEQ ID NO: 36 - Amino acid sequence of a LCVR of a human antibody that binds GCGR
DIQMTQSPSSLSASVGDRVTITCRASQGIRNDLGWYQQKPGKAPKRLIYAASSLESGVPSRFS
GSGSGTEFTLTISSLQPEDFATYYCLQHNSYPWTFGQGTKVEIKR SEQ ID NO: 37 - Amino acid sequence of a LCVR of a human antibody that binds GCGR
KIVMTQTPLALPVIPGEPASISCRSSQSLVDSDDGDTYLDWYLQKPGQSPQVLIHRLSYRASGV
PDRFSGSGSGTDFTLKISRVEAEDVGIYYCMHRIEFPFTFGGGTKVEIKR SEQ ID NO: 38 - Amino acid sequence of a LCVR of a human antibody that binds GCGR
DIQMTQSPSSLSASVGDRVTITCRASQGIRNDLGWYQQRPGKAPKRLIYAASSLQTGVPSRFS
GSGSGTEFTLTISSLQPEDFATYYCLQHNSYPWTFGQGTKVEIKR SEQ ID NO: 39 - Amino acid sequence of a LCVR of a human antibody that binds GCGR
GIVLTQSPLSLPVTPGEPASISCRSSQSLLHSNGYNYLDWYLQKPGQSPQLLIYLGSNRASGVP
DRFSGSGSGTDFTLKISRVEAEDVGVYYCMEALQTMCSFGQGTKLEIKR SEQ ID NO: 40 - Amino acid sequence of a LCVR of a human antibody that binds GCGR
GIVLTQSPLSLPVTPGEPASISCRSSQSLLHSNGYNYLDWYLQKPGQSPQLLIYLGSNRASGVP
DRFSGSGSGTDFTLKISRVEAEDVGVYYCMEALQTMSSFGQGTKLEIKR SEQ ID NO: 41 - Amino acid sequence of a LCVR of a human antibody that binds GCGR
DIVMTQTPLFLPVTPGEPASISCRSSQTLLDSDDGNTYLDWYLQKPGQSPQRLIYTLSYRASGV
PDRFSGSGSGTDFTLKISRVEAEDVGIYYCMQHIEFPSTFGQGTRLEIKR SEQ ID NO: 42 - Amino acid sequence of a LCVR of a human antibody that binds GCGR
SYELTQPPSVSVSPGQTASITCSGDKLGDKYASWYQQKPGQSPVLVIYQSTKRPSGIPERFSG
SNSGNTATLTISGTQAMDEADYYCQAWDSSTVVFGGGTKLTVLG SEQ ID NO: 43 - Amino acid sequence of a LCVR of a human antibody that binds GCGR
NIVMTQTPLSLSVTPGQPASISCKSSQSLLHSDGKNYLFWYLQKPGQSPQLLIYEVSYRFSGVP
DRFSGSGSGTDFSLKISRVEAEDVGVYYCMQNIQPPLIFGQGTRLEIKR SEQ ID NO: 44 - Amino acid sequence of a LCVR of a human antibody that binds GCGR
DIQMTQSPSSLSASVGDRVTITCRASQGIRNDLGWYQQKPGKAPKRLIYAASSLQSGVPSRFS
GSGSGTEFTLTISSVQPEDFVTYYCLQHNSNPLTFGGGTKVEIKR SEQ ID NO: 45 - Amino acid sequence of a LCVR of a human antibody that binds GCGR
DIQMTQSPSSLSASVGDRVTITCRASQGIRNDLGWYQQKPGKAPKRLIYAASSLESGVPSRFS
GSGSGTEFTLTISSVQPEDFVTYYCLQHNSNPLTFGGGTKVEIKR SEQ ID NO: 46 - Amino acid sequence of the constant light chain kappa region
RTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC SEQ ID NO: 47 - Amino acid sequence of the constant light chain lambda region
GQPKAAPSVTLFPPSSEELQANKATLVCLISDFYPGAVTVAWKADSSPVKAGVETTTPSKQSN
NKYAASSYLSLTPEQWKSHRSYSCQVTHEGSTVEKTVAPTECS SEQ ID NO: 48 - Amino sequence of the IgG2 heavy chain constant region
ASTKGPSVFPLAPCSRSTSESTAALGCLVKDYFPEPVTVSWNSGALTSGVHTFPAVLQSSGLY
SLSSVVTVPSSNFGTQTYTCNVDHKPSNTKVDKTVERKCCVECPPCPAPPVAGPSVFLFPPKP
KDTLMISRTPEVTCVVVDVSHEDPEVQFNWYVDGVEVHNAKTKPREEQFNSTFRVVSVLTVVH
QDWLNGKEYKCKVSNKGLPAPIEKTISKTKGQPREPQVYTLPPSREEMTKNQVSLTCLVKGFY
PSDIAVEWESNGQPENNYKTTPPMLDSDGSFFLYSKLTVDKSRWQQGNVFSCSVMHEALHNH
YTQKSLSLSPGK SEQ ID NO: 49 - Amino acid sequence of a HC of a human antibody that binds GCGR
QVQLVESGGGVVQPGRSLRLSCAASGFTFSSYGMHWVRQAPGKGLEWVAVMWYD
GSNKDYVDSVKGRFTISRDNSKNTLYLQMNRLRAEDTAVYYCAREKDHYDILTGYN
YYYGLDVWGQGTTVTVSSASTKGPSVFPLAPCSRSTSESTAALGCLVKDYFPEPVTVSWN
SGALTSGVHTFPAVLQSSGLYSLSSVVTVPSSNFGTQTYTCNVDHKPSNTKVDKTVERKCCVE
CPPCPAPPVAGPSVFLFPPKPKDTLMISRTPEVTCVVVDVSHEDPEVQFNWYVDGVEVHNAKT
KPREEQFNSTFRVVSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDGSFFLYSKLTVDKS
RWQQGNVFSCSVMHEALHNHYTQKSLSLSPGK SEQ ID NO: 50 - Amino acid sequence of a LC of a human antibody that binds GCGR
DIQMTQSPSSLSASVGDRVTITCRASQGIRNDLGWYQQKPGKAPKRLIYAASSLQSGV
PSRFSGSGSGTEFTLTISSVQPEDFVTYYCLQHNSNPLTFGGGTKVEIKRTVAAPSVFIF
PPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC

What is claimed is:

1. A method for treating cancer in a subject in need thereof, comprising administering to the subject a therapeutically effective amount of a phosphatidylinositol 3-kinase (PI3K) pathway inhibitor, and a therapeutically effective amount of an isolated glucagon receptor (GCGR) antagonist, wherein PI3K pathway inhibitor-induced hyperglycemia and hyperinsulinemia is reduced while sustaining tumor PI3K inhibition as compared to a subject treated with only a PI3K pathway inhibitor; wherein the isolated GCGR antagonist is selected from the group consisting of a fully human GCGR antagonist antibody, a humanized GCGR antagonist antibody, and a chimeric GCGR antagonist antibody; and wherein the PI3K pathway inhibitor is not an inhibitor of mTOR.

2. A method according to claim 1, wherein the isolated GCGR antagonistic antibody specifically binds to a human glucagon receptor with a dissociation constant ($K_D$) of at least about $1\times10^{-7}$ M, at least about $1\times10^{-8}$ M, at least about $1\times10^{-9}$ M, at least about $1\times10^{-10}$ M, at least about $1\times10^{-11}$ M, or at least about $1\times10^{-12}$ M.

3. A method according to claim 2, wherein the isolated GCGR antagonistic antibody is a fully human antibody.

4. A method according to claim 3, wherein the fully human antibody comprises a human anti-GCGR antibody which comprises the amino acid sequence encoding the heavy chain of SEQ ID NO: 49 and the amino acid sequence encoding the light chain of SEQ ID NO: 50.

5. A method according to claim 2, wherein the therapeutically effective amount of the isolated GCGR antagonist antibody is selected from the group consisting of: 0.001 to 10 mg/kg, 0.001 to 9 mg/kg, 0.001 to 8 mg/kg, 0.001 to 7 mg/kg, 0.001 to 6 mg/kg, 0.001 to 5 mg/kg, 0.001 to 4 mg/kg, 0.001 to 3 mg/kg, 0.001 to 20 mg/kg, 0.001 to 1 mg/kg, 0.010 to 10 mg/kg, 0.010 to 9 mg/kg, 0.010 to 8 mg/kg, 0.010 to 7 mg/kg, 0.010 to 6 mg/kg, 0.010 to 5 mg/kg, 0.010 to 4 mg/kg, 0.010 to 3 mg/kg, 0.010 to 2 mg/kg, 0.010 to 1 mg/kg, 0.1 to 10 mg/kg, 0.1 to 9 mg/kg, 0.1 to 8 mg/kg, 0.1 to 7 mg/kg, 0.1 to 6 mg/kg, 0.1 to 5 mg/kg, 0.1 to 4 mg/kg, 0.1 to 3 mg/kg, 0.1 to 2 mg/kg, 0.1 to 1 mg/kg, 0.5 to 10 mg/kg, 0.5 to 9 mg/kg, 0.5 to 8 mg/kg, 0.5 to 7 mg/kg, 0.5 to 6 mg/kg, 0.5 to 5 mg/kg, 0.5 to 4 mg/kg, 0.5 to 3 mg/kg, 0.5 to 2 mg/kg, 0.5 to 1 mg/kg, 1 to 10 mg/kg, 1 to 9 mg/kg, 1 to 8 mg/kg, 1 to 7 mg/kg, 1 to 6 mg/kg, 1 to 5 mg/kg, 1 to 4 mg/kg, 1 to 3 mg/kg, and 1 to 2 mg/kg body weight per week.

6. A method according to claim 1, wherein the PI3K pathway inhibitor is an AKT inhibitor.

7. A method according to claim 6, wherein the AKT inhibitor is selected from the group consisting of: miltefosine, perifosine, PF-04691502, CCT128930, A-674563, MK-2206, RX-0201, PBI-05204, AZD5363, GDC-0068 (Ipatasertib), TIC10, Akti-$1/2$, AT7867, AT13148, SC79, GSK690693, GSK2110183 and GSK2141795.

8. A method according to claim 1, wherein the therapeutically effective amount of the PI3K pathway inhibitor is selected from the group consisting of 0.05 mg/kg to 75 mg/kg, 0.05 mg/kg to 70 mg/kg, 0.05 mg/kg to 60 mg/kg, 0.05 mg/kg to 50 mg/kg, 0.05 mg/kg to 40 mg/kg, 0.05 mg/kg to 30 mg/kg, 0.05 mg/kg to 20 mg/kg, 0.05 mg/kg to 10 mg/kg, 0.1 mg/kg to 75 mg/kg, 0.1 mg/kg to 30 mg/kg, 0.1 mg/kg to 40 mg/kg, 0.1 mg/kg to 50 mg/kg, 0.1 mg/kg to 40 mg/kg, 0.1 mg/kg to 30 mg/kg, 0.1 mg/kg to 20 mg/kg, 0.1 mg/kg to 10 mg/kg, 0.5 mg/kg to 75 mg/kg, 0.5 mg/kg to 70 mg/kg, 0.5 mg/kg to 60 mg/kg, 0.5 mg/kg to 50 mg/kg, 0.5 mg/kg to 40 mg/kg, 0.5 mg/kg to 30 mg/kg, 0.5 mg/kg to 20 mg/kg, 0.5 mg/kg to 10 mg/kg, 1 mg/kg to 75 mg/kg, 1 mg/kg to 70 mg/kg, 1 mg/kg to 60 mg/kg, 1 mg/kg to 50 mg/kg, 1 mg/kg to 40 mg/kg, 1 mg/kg to 30 mg/kg, 1 mg/kg to 20 mg/kg, 1 mg/kg to 10 mg/kg, 5 mg/kg to 75 mg/kg, 5 mg/kg to 70 mg/kg, 5 mg/kg to 60 mg/kg, 5 mg/kg to 50 mg/kg, 5 mg/kg to 40 mg/kg, 5 mg/kg to 30 mg/kg, 5 mg/kg to 20 mg/kg, and 5 mg/kg to 10 mg/kg body weight of the recipient per day.

9. A method according to claim 1, wherein the PI3K pathway inhibitor and GCGR antagonist are administered at the same time.

10. A method according to claim 1, wherein the PI3K pathway inhibitor and GCGR antagonist are administered at different times.

11. A method according to claim 1, wherein the cancer is selected from the group consisting of: B cell lymphoma; a lung cancer (small cell lung cancer and non-small cell lung cancer); a bronchus cancer; a colorectal cancer; a prostate cancer; a breast cancer; a pancreas cancer; a stomach cancer; an ovarian cancer; a urinary bladder cancer; a brain or central nervous system cancer; a peripheral nervous system cancer; an esophageal cancer; a cervical cancer; a melanoma; a uterine or endometrial cancer; a cancer of the oral cavity or pharynx; a liver cancer; a kidney cancer; a biliary tract cancer; a small bowel or appendix cancer; a salivary gland cancer; a thyroid gland cancer; a adrenal gland cancer; an osteosarcoma; a chondrosarcoma; a liposarcoma; a testes cancer; and a malignant fibrous histiocytoma; a skin cancer; a head and neck cancer; lymphomas; sarcomas; multiple myeloma; and leukemias.

12. A method according to claim 11, wherein the cancer is a recurrent cancer.

13. A method according to claim 11, wherein the cancer is resistant to or refractory to treatment with a PI3K pathway inhibitor.

* * * * *

SEQUENCE LISTING

<160> NUMBER OF SEQ ID NOS: 50

<210> SEQ ID NO 1
<211> LENGTH: 477
<212> TYPE: PRT
<213> ORGANISM: Homo sapiens

<400> SEQUENCE: 1

Met Pro Pro Cys Gln Pro Gln Arg Pro Leu Leu Leu Leu Leu Leu Leu
1               5                   10                  15

Leu Ala Cys Gln Pro Gln Val Pro Ser Ala Gln Val Met Asp Phe Leu
            20                  25                  30

Phe Glu Lys Trp Lys Leu Tyr Gly Asp Gln Cys His His Asn Leu Ser
        35                  40                  45

Leu Leu Pro Pro Pro Thr Glu Leu Val Cys Asn Arg Thr Phe Asp Lys
    50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
        115                 120                 125

Glu Val Gln Lys Glu Val Ala Lys Met Tyr Ser Ser Phe Gln Val Met
    130                 135                 140

Tyr Thr Val Gly Tyr Ser Leu Ser Leu Gly Ala Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
        275                 280                 285

Phe Glu Asn Val Gln Cys Trp Thr Ser Asn Asp Asn Met Gly Phe Trp
    290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
        355                 360                 365

```
Thr Asp Glu His Ala Gln Gly Thr Leu Arg Ser Ala Lys Leu Phe Phe
    370                 375                 380
Asp Leu Phe Leu Ser Ser Phe Gln Gly Leu Leu Val Ala Val Leu Tyr
385                 390                 395                 400
Cys Phe Leu Asn Lys Glu Val Gln Ser Glu Leu Arg Arg Arg Trp His
                405                 410                 415
Arg Trp Arg Leu Gly Lys Val Leu Trp Glu Arg Asn Thr Ser Asn
                420                 425                 430
His Arg Ala Ser Ser Pro Gly His Gly Pro Pro Ser Lys Glu Leu
                435                 440                 445
Gln Phe Gly Arg Gly Gly Ser Gln Asp Ser Ser Ala Glu Thr Pro
450                 455                 460
Leu Ala Gly Gly Leu Pro Arg Leu Ala Glu Ser Pro Phe
465                 470                 475
```

<210> SEQ ID NO 2
<211> LENGTH: 128
<212> TYPE: PRT
<213> ORGANISM: Homo sapiens

<400> SEQUENCE: 2

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
                20                  25                  30
Gly Met His Trp Val Arg Gln Ala Pro Gly Lys Gly Leu Glu Trp Val
            35                  40                  45
Ala Val Met Trp Tyr Asp Gly Ser Asn Lys Asp Tyr Val Asp Ser Val
50                  55                  60
Lys Gly Arg Phe Thr Ile Ser Arg Asp Asn Ser Lys Asn Thr Leu Tyr
65                  70                  75                  80
Leu Gln Met Asn Arg Leu Arg Ala Glu Asp Thr Ala Val Tyr Tyr Cys
                85                  90                  95
Ala Arg Glu Lys Asp His Tyr Asp Ile Leu Thr Gly Tyr Asn Tyr Tyr
                100                 105                 110
Tyr Gly Leu Asp Val Trp Gly Gln Gly Thr Thr Val Thr Val Ser Ser
            115                 120                 125
```

<210> SEQ ID NO 3
<211> LENGTH: 107
<212> TYPE: PRT
<213> ORGANISM: Homo sapiens

<400> SEQUENCE: 3

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
                20                  25                  30
Leu Gly Trp Tyr Gln Gln Lys Pro Gly Lys Ala Pro Lys Arg Leu Ile
            35                  40                  45
Tyr Ala Ala Ser Ser Leu Gln Ser Gly Val Pro Ser Arg Phe Ser Gly
50                  55                  60
Ser Gly Ser Gly Thr Glu Phe Thr Leu Thr Ile Ser Ser Val Gln Pro
65                  70                  75                  80
Glu Asp Phe Val Thr Tyr Tyr Cys Leu Gln His Asn Ser Asn Pro Leu
                85                  90                  95
```

Thr Phe Gly Gly Gly Thr Lys Val Glu Ile Lys
            100                 105

<210> SEQ ID NO 4
<211> LENGTH: 128
<212> TYPE: PRT
<213> ORGANISM: Homo sapiens

<400> SEQUENCE: 4

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125

<210> SEQ ID NO 5
<211> LENGTH: 107
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys
            100                 105

<210> SEQ ID NO 6
<211> LENGTH: 128
<212> TYPE: PRT
<213> ORGANISM: Homo sapiens

<400> SEQUENCE: 6

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val

```
                35                  40                  45
Ala Val Met Trp Tyr Asp Gly Ser Asn Lys Asp Tyr Val Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Arg Leu Arg Ala Glu Asp Thr Ala Val Tyr Tyr Cys
                 85                  90                  95
Ala Arg Glu Lys Asp His Tyr Asp Ile Leu Thr Gly Tyr Asn Tyr Tyr
                100                 105                 110
Tyr Gly Leu Asp Val Trp Gly Gln Gly Thr Thr Val Thr Val Ser Ser
            115                 120                 125

<210> SEQ ID NO 7
<211> LENGTH: 107
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Asp
             20                  25                  30
Leu Gly Trp Tyr Gln Gln Lys Pro Gly Lys Ala Pro Lys Arg Leu Ile
         35                  40                  45
Tyr Ala Ala Ser Ser Leu Glu Ser Gly Val Pro Ser Arg Phe Ser Gly
     50                  55                  60
Ser Gly Ser Gly Thr Glu Phe Thr Leu Thr Ile Ser Ser Val Gln Pro
 65                  70                  75                  80
Glu Asp Phe Val Thr Tyr Tyr Cys Leu Gln His Asn Ser Asn Pro Leu
                 85                  90                  95
Thr Phe Gly Gly Gly Thr Lys Val Glu Ile Lys
            100                 105

<210> SEQ ID NO 8
<211> LENGTH: 471
<212> TYPE: PRT
<213> ORGANISM: Artificial Sequence
<220> FEATURE:
<223> OTHER INFORMATION: heavy chain of a chimeric antibody that binds
      GCGR

<400> SEQUENCE: 8

Met Glu Phe Gly Leu Ser Trp Val Phe Leu Val Ala Leu Leu Arg Gly
 1               5                  10                  15
Val Gln Cys Gln Val Gln Leu Val Glu Ser Gly Gly Gly Val Val Gln
             20                  25                  30
Pro Gly Arg Ser Leu Arg Leu Ser Cys Ala Ala Ser Gly Phe Thr Phe
         35                  40                  45
Ser Ser Tyr Gly Met His Trp Val Arg Gln Ala Pro Gly Lys Gly Leu
     50                  55                  60
Glu Trp Val Ala Val Met Trp Tyr Asp Gly Ser Asn Lys Asp Tyr Val
 65                  70                  75                  80
Asp Ser Val Lys Gly Arg Phe Thr Ile Ser Arg Asp Asn Ser Lys Asn
                 85                  90                  95
Thr Leu Tyr Leu Gln Met Asn Arg Leu Arg Ala Glu Asp Thr Ala Val
                100                 105                 110
Tyr Tyr Cys Ala Arg Glu Lys Asp His Tyr Asp Ile Leu Thr Gly Tyr
```

```
            115                 120                 125
Asn Tyr Tyr Tyr Gly Leu Asp Val Trp Gly Gln Gly Thr Thr Val Thr
            130                 135                 140

Val Ser Ser Ala Lys Thr Thr Pro Pro Ser Val Tyr Pro Leu Ala Pro
145                 150                 155                 160

Gly Ser Ala Ala Gln Thr Asn Ser Met Val Thr Leu Gly Cys Leu Val
                165                 170                 175

Lys Gly Tyr Phe Pro Glu Pro Val Thr Val Thr Trp Asn Ser Gly Ser
                180                 185                 190

Leu Ser Ser Gly Val His Thr Phe Pro Ala Val Leu Gln Ser Asp Leu
            195                 200                 205

Tyr Thr Leu Ser Ser Ser Val Thr Val Pro Ser Ser Thr Trp Pro Ser
        210                 215                 220

Glu Thr Val Thr Cys Asn Val Ala His Pro Ala Ser Ser Thr Lys Val
225                 230                 235                 240

Asp Lys Lys Ile Val Pro Arg Asp Cys Gly Cys Lys Pro Cys Ile Cys
                245                 250                 255

Thr Val Pro Glu Val Ser Ser Val Phe Ile Phe Pro Pro Lys Pro Lys
            260                 265                 270

Asp Val Leu Thr Ile Thr Leu Thr Pro Lys Val Thr Cys Val Val Val
            275                 280                 285

Asp Ile Ser Lys Asp Asp Pro Glu Val Gln Phe Ser Trp Phe Val Asp
290                 295                 300

Asp Val Glu Val His Thr Ala Gln Thr Gln Pro Arg Glu Glu Gln Phe
305                 310                 315                 320

Asn Ser Thr Phe Arg Ser Val Ser Glu Leu Pro Ile Met His Gln Asp
                325                 330                 335

Trp Leu Asn Gly Lys Glu Phe Lys Cys Arg Val Asn Ser Ala Ala Phe
            340                 345                 350

Pro Ala Pro Ile Glu Lys Thr Ile Ser Lys Thr Lys Gly Arg Pro Lys
        355                 360                 365

Ala Pro Gln Val Tyr Thr Ile Pro Pro Pro Lys Glu Gln Met Ala Lys
    370                 375                 380

Asp Lys Val Ser Leu Thr Cys Met Ile Thr Asp Phe Phe Pro Glu Asp
385                 390                 395                 400

Ile Thr Val Glu Trp Gln Trp Asn Gly Gln Pro Ala Glu Asn Tyr Lys
                405                 410                 415

Asn Thr Gln Pro Ile Met Asp Thr Asp Gly Ser Tyr Phe Val Tyr Ser
                420                 425                 430

Lys Leu Asn Val Gln Lys Ser Asn Trp Glu Ala Gly Asn Thr Phe Thr
            435                 440                 445

Cys Ser Val Leu His Glu Gly Leu His Asn His Thr Glu Lys Ser
        450                 455                 460

Leu Ser His Ser Pro Gly Lys
465                 470

<210> SEQ ID NO 9
<211> LENGTH: 236
<212> TYPE: PRT
<213> ORGANISM: Artificial Sequence
<220> FEATURE:
<223> OTHER INFORMATION: light chain of a chimeric antibody that binds
      GCGR

<400> SEQUENCE: 9
```

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Glu Ser Gly Val
65                  70                  75                  80

Pro Ser Arg Phe Ser Gly Ser Gly Ser Gly Thr Glu Phe Thr Leu Thr
                85                  90                  95

Ile Ser Ser Val Gln Pro Glu Asp Phe Val Thr Tyr Tyr Cys Leu Gln
            100                 105                 110

His Asn Ser Asn Pro Leu Thr Phe Gly Gly Gly Thr Lys Val Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235

<210> SEQ ID NO 10
<211> LENGTH: 125
<212> TYPE: PRT
<213> ORGANISM: Homo sapiens

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Leu Ser Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Glu Ile Leu Thr Gly Tyr Gly Tyr Tyr Gly Met
            100                 105                 110

Asp Val Trp Gly Gln Gly Thr Thr Val Thr Val Ser Ser
        115                 120                 125

<210> SEQ ID NO 11
```

<211> LENGTH: 125
<212> TYPE: PRT
<213> ORGANISM: Homo sapiens

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Leu Asn Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Glu Ile Leu Thr Gly Tyr Gly Tyr Tyr Gly Met
            100                 105                 110

Asp Val Trp Gly Gln Gly Thr Thr Val Thr Val Ser Ser
        115                 120                 125

<210> SEQ ID NO 12
<211> LENGTH: 129
<212> TYPE: PRT
<213> ORGANISM: Homo sapiens

<400> SEQUENCE: 12

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Gly Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Tyr Asp Tyr Ala
    50                  55                  60

Gly Ser Val Lys Ser Arg Ile Asn Ile Asn Pro Asp Thr Ser Lys Asn
65                  70                  75                  80

Gln Phe Ser Leu Gln Val Asn Ser Val Thr Pro Glu Asp Thr Ala Val
                85                  90                  95

Tyr Tyr Cys Thr Arg Asp Arg Ser Ser Gly Trp Asn Glu Gly Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 13
<211> LENGTH: 128
<212> TYPE: PRT
<213> ORGANISM: Homo sapiens

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Pro Gly Lys Gly Leu Glu Trp Val

```
                35                  40                  45
Ala Val Leu Ser Ser Asp Gly Asn Asn Lys Tyr Cys Ala Asp Ser Val
            50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Thr Glu Asp Thr Ala Val Tyr Tyr Cys
                85                  90                  95
Ala Arg Glu Glu Val Tyr Tyr Asp Ile Leu Thr Gly Tyr Tyr Asp Tyr
            100                 105                 110
Tyr Gly Met Asp Val Trp Gly Gln Gly Thr Thr Val Thr Val Ser Ser
        115                 120                 125

<210> SEQ ID NO 14
<211> LENGTH: 126
<212> TYPE: PRT
<213> ORGANISM: Homo sapiens

<400> SEQUENCE: 14

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Thr Tyr
            20                  25                  30
Phe Trp Thr Trp Ile Arg Gln Phe Pro Gly Lys Gly Leu Glu Trp Ile
        35                  40                  45
Gly Tyr Ile Phe Tyr Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Glu Gly Tyr Tyr Asp Ile Leu Thr Gly Glu Asp Tyr Ser Tyr Gly
            100                 105                 110
Met Asp Val Trp Gly Gln Gly Thr Val Thr Val Ser Ser
        115                 120                 125

<210> SEQ ID NO 15
<211> LENGTH: 129
<212> TYPE: PRT
<213> ORGANISM: Homo sapiens

<400> SEQUENCE: 15

Gln Val Gln Leu Gln Gln Ser Gly Pro Gly Leu Val Lys Pro Ser Gln
1               5                   10                  15
Ile Leu Ser Leu Thr Cys Ala Ile Ser Gly Asp Arg Val Ser Ser Asn
            20                  25                  30
Gly Ala Ala Trp Asn Trp Ile Arg Gln Ser Pro Ser Arg Gly Leu Glu
        35                  40                  45
Trp Leu Gly Arg Thr Tyr Tyr Arg Ser Lys Trp Tyr Tyr Asp Tyr Ala
    50                  55                  60
Gly Ser Val Lys Ser Arg Ile Asn Ile Asn Pro Asp Thr Ser Lys Asn
65                  70                  75                  80
Gln Phe Ser Leu Gln Val Asn Ser Val Thr Pro Glu Asp Thr Ala Val
                85                  90                  95
Tyr Tyr Cys Ala Arg Asp Arg Ser Ser Gly Trp Asn Glu Gly Tyr Tyr
            100                 105                 110
Tyr Tyr Gly Met Asp Val Trp Gly Gln Gly Thr Thr Val Thr Val Ser
```

-continued

```
            115                 120                 125
Ser

<210> SEQ ID NO 16
<211> LENGTH: 126
<212> TYPE: PRT
<213> ORGANISM: Homo sapiens

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Phe Trp Thr Trp Ile Arg Gln Phe Pro Gly Glu Gly Leu Glu Trp Ile
        35                  40                  45

Gly Tyr Ile Phe Tyr Ser Gly Asn Thr Asn Tyr Asn Pro Ser Leu Thr
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Tyr Asp Ile Leu Thr Gly Glu Asp Tyr Ser Tyr Gly
            100                 105                 110

Ile Asp Val Trp Gly Gln Gly Thr Thr Val Thr Val Ser Ser
        115                 120                 125

<210> SEQ ID NO 17
<211> LENGTH: 125
<212> TYPE: PRT
<213> ORGANISM: Homo sapiens

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Gly Met His Trp Val Arg Gln Ala Pro Gly Lys Gly Leu Glu Trp Val
        35                  40                  45

Ala Val Ile Ser Asn Asp Gly Ser Asn Lys Tyr Tyr Ala Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Tyr Asp Ile Leu Thr Gly Asn Gly Val Tyr Gly Met
            100                 105                 110

Asp Val Trp Gly Gln Gly Thr Thr Val Thr Val Ser Ser
        115                 120                 125

<210> SEQ ID NO 18
<211> LENGTH: 122
<212> TYPE: PRT
<213> ORGANISM: Homo sapiens

<400> SEQUENCE: 18

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Tyr Ile Ser Gly Ser Ser Leu Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu His Met Asn Ser Leu Arg Asp Glu Asp Thr Ala Val Tyr Tyr Cys
                85                  90                  95

Ala Arg Ala Arg Tyr Asn Trp Asn Asp Tyr Tyr Gly Met Asp Val Trp
            100                 105                 110

Gly Gln Gly Thr Thr Val Thr Val Ser Ser
            115                 120

<210> SEQ ID NO 19
<211> LENGTH: 116
<212> TYPE: PRT
<213> ORGANISM: Homo sapiens

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Ile His Trp Val Arg Gln Ala Pro Gly Lys Gly Leu Glu Trp Val
        35                  40                  45

Ala Gly Ile Trp Tyr Asp Gly Ser Asn Lys Tyr Tyr Ala Asp Ser Val
50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Phe Asp Ala Phe Asp Ile Trp Gly Gln Gly Thr Met Val
            100                 105                 110

Thr Val Ser Ser
115

<210> SEQ ID NO 20
<211> LENGTH: 128
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Thr Met Asn Trp Val Arg Gln Ala Pro Gly Lys Gly Leu Glu Trp Val
        35                  40                  45

Ser Tyr Ile Ser Ser Ser Ser Leu Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Ser Asp Tyr Tyr Gly Ser Gly Ser Tyr Lys Gly Asn Tyr
            100                 105                 110

Tyr Gly Met Asp Val Trp Gly Gln Gly Thr Thr Val Thr Val Ser Ser
        115                 120                 125

<210> SEQ ID NO 21
<211> LENGTH: 128
<212> TYPE: PRT
<213> ORGANISM: Homo sapiens

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Thr Ile Ile Trp Ser Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Glu Arg Gly Leu Tyr Asp Ile Leu Thr Gly Tyr Tyr Asp Tyr
            100                 105                 110

Tyr Gly Ile Asp Val Trp Gly Gln Gly Thr Thr Val Thr Val Ser Ser
        115                 120                 125

<210> SEQ ID NO 22
<211> LENGTH: 128
<212> TYPE: PRT
<213> ORGANISM: Homo sapiens

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Thr Ile Ile Trp Ser Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Glu Arg Gly Leu Tyr Asp Ile Leu Thr Gly Tyr Tyr Asp Tyr
            100                 105                 110

Tyr Gly Ile Asp Val Trp Gly Gln Gly Thr Thr Val Thr Val Ser Ser
        115                 120                 125

<210> SEQ ID NO 23
<211> LENGTH: 116
<212> TYPE: PRT
<213> ORGANISM: Homo sapiens

<400> SEQUENCE: 23

Glu Val Gln Leu Val Glu Ser Gly Gly Gly Leu Val Lys Pro Gly Gly

```
   1               5                  10                 15
Ser Leu Arg Leu Ser Cys Ala Ala Ser Gly Ile Thr Phe Arg Ser Tyr
                20                  25                 30

Ser Met Asn Trp Val Arg Gln Ala Pro Gly Lys Gly Leu Glu Trp Val
                35                  40                 45

Ser Ala Ile Ser Ser Ser Ser Tyr Ile Tyr Tyr Ala Asp Ser Val
                50                  55                 60

Lys Gly Arg Phe Thr Ile Ser Arg Asp Asn Ala Lys Asn Ser Val Tyr
 65                  70                 75                 80

Leu Gln Met Asn Ser Leu Arg Ala Glu Asp Thr Ala Val Tyr Tyr Cys
                85                  90                 95

Ala Arg Gly Arg Tyr Gly Met Asp Val Trp Gly Gln Gly Thr Thr Val
                100                 105                110

Thr Val Ser Ser
         115
```

<210> SEQ ID NO 24
<211> LENGTH: 125
<212> TYPE: PRT
<213> ORGANISM: Homo sapiens

<400> SEQUENCE: 24

```
Gln Val Gln Leu Val Glu Ser Gly Gly Gly Val Val Gln Pro Gly Arg
 1               5                  10                 15

Ser Leu Arg Leu Ser Cys Ala Ala Ser Gly Ser Thr Phe Arg Ser Tyr
                20                  25                 30

Asp Met His Trp Val Arg Gln Ala Pro Gly Lys Gly Leu Glu Trp Val
                35                  40                 45

Ala Val Ile Ser Tyr Asp Gly Ser Asn Lys Tyr Tyr Gly Asp Ser Val
                50                  55                 60

Lys Gly Arg Leu Thr Ile Ser Arg Asp Asn Ser Lys Asn Thr Leu Tyr
 65                  70                 75                 80

Leu Gln Met Asn Ser Leu Arg Ala Glu Asp Thr Ala Val Tyr Tyr Cys
                85                  90                 95

Ala Arg Asp Gln Tyr Asp Ile Leu Thr Gly Tyr Ser Ser Asp Ala Phe
                100                 105                110

Asp Ile Trp Gly Gln Gly Thr Met Val Thr Val Ser Ser
                115                 120                125
```

<210> SEQ ID NO 25
<211> LENGTH: 127
<212> TYPE: PRT
<213> ORGANISM: Homo sapiens

<400> SEQUENCE: 25

```
Gln Val Gln Leu Val Glu Ser Gly Gly Gly Val Val Gln Pro Gly Arg
 1               5                  10                 15

Ser Leu Arg Leu Ser Cys Ala Ala Ser Gly Phe Thr Phe Ser Arg Tyr
                20                  25                 30

Gly Met His Trp Val Arg Gln Ala Pro Gly Lys Gly Leu Glu Trp Val
                35                  40                 45

Ala Val Ile Trp Tyr Asp Gly Ser His Lys Tyr Tyr Glu Asp Ser Val
                50                  55                 60

Lys Gly Arg Phe Thr Ile Ser Arg Asp Asn Ser Lys Asn Thr Leu Tyr
 65                  70                 75                 80

Leu Gln Met Asn Ser Leu Arg Ala Asp Asp Thr Gly Val Tyr Tyr Cys
```

Ala Arg Val Gly Tyr Gly Ser Gly Trp Tyr Glu Tyr Tyr His Tyr
                100                 105                 110

Gly Met Asp Val Trp Gly Gln Gly Thr Thr Val Thr Val Ser Ser
            115                 120                 125

<210> SEQ ID NO 26
<211> LENGTH: 128
<212> TYPE: PRT
<213> ORGANISM: Homo sapiens

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125

<210> SEQ ID NO 27
<211> LENGTH: 128
<212> TYPE: PRT
<213> ORGANISM: Homo sapiens

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125

<210> SEQ ID NO 28
<211> LENGTH: 108
<212> TYPE: PRT
<213> ORGANISM: Homo sapiens

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Lys Lys Pro Gly Lys Ala Pro Lys Ser Leu Ile
        35                  40                  45

Tyr Val Val Ser Ser Leu Gln Ser Gly Val Pro Ser Arg Phe Ser Gly
    50                  55                  60

Ser Gly Ser Gly Thr Asp Phe Thr Leu Thr Ile Asn Asn Leu Gln Pro
65                  70                  75                  80

Glu Asp Phe Ala Thr Tyr Tyr Cys Gln Gln Tyr Asn His Tyr Pro Leu
                85                  90                  95

Thr Phe Gly Gly Gly Thr Arg Val Glu Ile Lys Arg
            100                 105

<210> SEQ ID NO 29
<211> LENGTH: 108
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Arg Pro Gly Lys Ala Pro Lys Ser Leu Ile
        35                  40                  45

Tyr Val Val Ser Ser Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Phe Cys Gln Gln Tyr Asn His Tyr Pro Leu
                85                  90                  95

Thr Phe Gly Gly Gly Thr Lys Val Glu Ile Lys Arg
            100                 105

<210> SEQ ID NO 30
<211> LENGTH: 108
<212> TYPE: PRT
<213> ORGANISM: Homo sapiens

<400> SEQUENCE: 30

Asp Ile Gln Met Thr Gln Phe Pro Ser Ser Leu Ser Ala Ser Ile Gly
1               5                   10                  15

Asp Arg Val Thr Ile Thr Cys Gln Ala Ser Gln Asp Ile Ser Asn Phe
            20                  25                  30

Leu Asn Trp Phe Gln Gln Lys Pro Gly Lys Ala Pro Lys Leu Leu Ile
        35                  40                  45

Tyr Asp Ala Ser Asp Leu Glu Thr Gly Val Pro Ser Arg Phe Ser Gly
    50                  55                  60

Ser Gly Ala Gly Thr Asp Phe Thr Phe Thr Ile Ser Ser Leu Gln Pro
65                  70                  75                  80

Glu Asp Ile Ala Thr Tyr Phe Cys Gln Gln Tyr Asp Asp Leu Pro Leu
                85                  90                  95

Thr Phe Gly Gly Gly Thr Arg Val Asp Ile Lys Arg
            100                 105
```

<210> SEQ ID NO 31
<211> LENGTH: 108
<212> TYPE: PRT
<213> ORGANISM: Homo sapiens

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Asn Pro Leu
                85                  90                  95

Thr Phe Gly Gly Gly Thr Lys Val Glu Ile Lys Arg
            100                 105

<210> SEQ ID NO 32
<211> LENGTH: 109
<212> TYPE: PRT
<213> ORGANISM: Homo sapiens

<400> SEQUENCE: 32

Gln Asn Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Val Ser Ser Arg Ala Thr Gly Ile Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Phe Thr Phe Gly Pro Gly Thr Lys Val Asp Ile Lys Arg
            100                 105

<210> SEQ ID NO 33
<211> LENGTH: 108
<212> TYPE: PRT
<213> ORGANISM: Homo sapiens

<400> SEQUENCE: 33

Asp Ile Gln Met Thr Gln Phe Pro Ser Ser Leu Ser Ala Ser Ile Gly
1               5                   10                  15

Asp Arg Val Thr Ile Thr Cys Gln Ala Ser Gln Asp Ile Ser Asn Phe
            20                  25                  30

Leu Asn Trp Phe Gln Gln Lys Pro Gly Lys Ala Pro Lys Leu Leu Ile
        35                  40                  45

Tyr Asp Ala Ser Asp Leu Glu Thr Gly Val Pro Ser Arg Phe Ser Gly
    50                  55                  60

Ser Gly Ala Gly Thr Asp Phe Thr Phe Thr Ile Ser Ser Leu Gln Pro
65                  70                  75                  80

Glu Asp Val Ala Thr Tyr Phe Cys Gln Gln Tyr Asp Asn Leu Pro Leu
                85                  90                  95

Thr Phe Gly Gly Gly Thr Lys Val Asp Ile Lys Arg
            100                 105

<210> SEQ ID NO 34
<211> LENGTH: 109
<212> TYPE: PRT
<213> ORGANISM: Homo sapiens

<400> SEQUENCE: 34

Glu Asn Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Phe Gly Val Ser Ser Arg Ala Thr Gly Ile Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Phe Thr Phe Gly Pro Gly Thr Lys Val Asp Ile Lys Arg
            100                 105

<210> SEQ ID NO 35
<211> LENGTH: 108
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asp Met Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Phe Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Phe Pro Phe
                85                  90                  95

Thr Phe Gly Pro Gly Thr Lys Val Asp Val Lys Arg
            100                 105

<210> SEQ ID NO 36
<211> LENGTH: 108
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp

```
                20                  25                  30
Leu Gly Trp Tyr Gln Gln Lys Pro Gly Lys Ala Pro Lys Arg Leu Ile
            35                  40                  45
Tyr Ala Ala Ser Ser Leu Glu Ser Gly Val Pro Ser Arg Phe Ser Gly
        50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Trp
                85                  90                  95
Thr Phe Gly Gln Gly Thr Lys Val Glu Ile Lys Arg
            100                 105
```

<210> SEQ ID NO 37
<211> LENGTH: 114
<212> TYPE: PRT
<213> ORGANISM: Homo sapiens

<400> SEQUENCE: 37

```
Lys Ile Val Met Thr Gln Thr Pro Leu Ala Leu Pro Val Ile Pro Gly
1               5                   10                  15
Glu Pro Ala Ser Ile Ser Cys Arg Ser Ser Gln Ser Leu Val Asp Ser
                20                  25                  30
Asp Asp Gly Asp Thr Tyr Leu Asp Trp Tyr Leu Gln Lys Pro Gly Gln
            35                  40                  45
Ser Pro Gln Val Leu Ile His Arg Leu Ser Tyr Arg Ala Ser Gly Val
        50                  55                  60
Pro Asp Arg Phe Ser Gly Ser Gly Ser Gly Thr Asp Phe Thr Leu Lys
65                  70                  75                  80
Ile Ser Arg Val Glu Ala Glu Asp Val Gly Ile Tyr Tyr Cys Met His
                85                  90                  95
Arg Ile Glu Phe Pro Phe Thr Phe Gly Gly Gly Thr Lys Val Glu Ile
            100                 105                 110
Lys Arg
```

<210> SEQ ID NO 38
<211> LENGTH: 108
<212> TYPE: PRT
<213> ORGANISM: Homo sapiens

<400> SEQUENCE: 38

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
                20                  25                  30
Leu Gly Trp Tyr Gln Gln Arg Pro Gly Lys Ala Pro Lys Arg Leu Ile
            35                  40                  45
Tyr Ala Ala Ser Ser Leu Gln Thr Gly Val Pro Ser Arg Phe Ser Gly
        50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Trp
                85                  90                  95
Thr Phe Gly Gln Gly Thr Lys Val Glu Ile Lys Arg
            100                 105
```

<210> SEQ ID NO 39

```
<211> LENGTH: 113
<212> TYPE: PRT
<213> ORGANISM: Homo sapiens

<400> SEQUENCE: 39

Gly Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Glu Ala
                85                  90                  95

Leu Gln Thr Met Cys Ser Phe Gly Gln Gly Thr Lys Leu Glu Ile Lys
            100                 105                 110

Arg

<210> SEQ ID NO 40
<211> LENGTH: 113
<212> TYPE: PRT
<213> ORGANISM: Homo sapiens

<400> SEQUENCE: 40

Gly Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Glu Ala
                85                  90                  95

Leu Gln Thr Met Ser Ser Phe Gly Gln Gly Thr Lys Leu Glu Ile Lys
            100                 105                 110

Arg

<210> SEQ ID NO 41
<211> LENGTH: 114
<212> TYPE: PRT
<213> ORGANISM: Homo sapiens

<400> SEQUENCE: 41

Asp Ile Val Met Thr Gln Thr Pro Leu Phe Leu Pro Val Thr Pro Gly
1               5                   10                  15

Glu Pro Ala Ser Ile Ser Cys Arg Ser Ser Gln Thr Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Arg Leu Ile Tyr Thr Leu Ser Tyr Arg Ala Ser Gly Val
    50                  55                  60
```

-continued

```
Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Ile Tyr Tyr Cys Met Gln
                 85                  90                  95

His Ile Glu Phe Pro Ser Thr Phe Gly Gln Gly Thr Arg Leu Glu Ile
            100                 105                 110

Lys Arg

<210> SEQ ID NO 42
<211> LENGTH: 107
<212> TYPE: PRT
<213> ORGANISM: Homo sapiens

<400> SEQUENCE: 42

Ser Tyr Glu Leu Thr Gln Pro Pro Ser Val Ser Val Ser Pro Gly Gln
  1               5                  10                  15

Thr Ala Ser Ile Thr Cys Ser Gly Asp Lys Leu Gly Asp Lys Tyr Ala
                 20                  25                  30

Ser Trp Tyr Gln Gln Lys Pro Gly Gln Ser Pro Val Leu Val Ile Tyr
             35                  40                  45

Gln Ser Thr Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Val Val
                 85                  90                  95

Phe Gly Gly Gly Thr Lys Leu Thr Val Leu Gly
            100                 105

<210> SEQ ID NO 43
<211> LENGTH: 113
<212> TYPE: PRT
<213> ORGANISM: Homo sapiens

<400> SEQUENCE: 43

Asn Ile Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu His Ser
                 20                  25                  30

Asp Gly Lys Asn Tyr Leu Phe Trp Tyr Leu Gln Lys Pro Gly Gln Ser
             35                  40                  45

Pro Gln Leu Leu Ile Tyr Glu Val Ser Tyr Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Asn
                 85                  90                  95

Ile Gln Pro Pro Leu Thr Phe Gly Gln Gly Thr Arg Leu Glu Ile Lys
            100                 105                 110

Arg

<210> SEQ ID NO 44
<211> LENGTH: 108
<212> TYPE: PRT
<213> ORGANISM: Homo sapiens

<400> SEQUENCE: 44
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Val Gln Pro
65              70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys Arg
            100                 105
```

<210> SEQ ID NO 45
<211> LENGTH: 108
<212> TYPE: PRT
<213> ORGANISM: Homo sapiens

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Val Gln Pro
65              70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys Arg
            100                 105
```

<210> SEQ ID NO 46
<211> LENGTH: 107
<212> TYPE: PRT
<213> ORGANISM: Homo sapiens

<400> SEQUENCE: 46

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 47
<211> LENGTH: 106
<212> TYPE: PRT
<213> ORGANISM: Homo sapiens

<400> SEQUENCE: 47

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 48
<211> LENGTH: 326
<212> TYPE: PRT
<213> ORGANISM: Homo sapiens

<400> SEQUENCE: 48

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 49
<211> LENGTH: 454
<212> TYPE: PRT
<213> ORGANISM: Homo sapiens

<400> SEQUENCE: 49

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Asn Phe Gly Thr Gln Thr
        195                 200                 205

Tyr Thr Cys Asn Val Asp His Lys Pro Ser Asn Thr Lys Val Asp Lys
    210                 215                 220

Thr Val Glu Arg Lys Cys Cys Val Glu Cys Pro Pro Cys Pro Ala Pro
225                 230                 235                 240

Pro Val Ala Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
```

```
                    260                 265                 270
Val Ser His Glu Asp Pro Glu Val Gln Phe Asn Trp Tyr Val Asp Gly
            275                 280                 285
Val Glu Val His Asn Ala Lys Thr Lys Pro Arg Glu Glu Gln Phe Asn
        290                 295                 300
Ser Thr Phe Arg Val Val Ser Val Leu Thr Val Val His Gln Asp Trp
305                 310                 315                 320
Leu Asn Gly Lys Glu Tyr Lys Cys Lys Val Ser Asn Lys Gly Leu Pro
                325                 330                 335
Ala Pro Ile Glu Lys Thr Ile Ser Lys Thr Lys Gly Gln Pro Arg Glu
            340                 345                 350
Pro Gln Val Tyr Thr Leu Pro Pro Ser Arg Glu Glu Met Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Met Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450

<210> SEQ ID NO 50
<211> LENGTH: 214
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Val Gln Pro
65                  70                  75                  80
Glu Asp Phe Val Thr Tyr Tyr Cys Leu Gln His Asn Ser Asn Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
```

-continued

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```